(12) United States Patent
Spence et al.

(10) Patent No.: US 6,884,251 B2
(45) Date of Patent: Apr. 26, 2005

(54) APPARATUS AND METHOD FOR PERFORMING AN ANASTOMOSIS

(75) Inventors: Paul A. Spence, Louisville, KY (US); Warren P. Williamson, IV, Loveland, OH (US); George Christakis, Toronto (CA); Mark Ortiz, Milford, OH (US); Craig B. Berky, Milford, OH (US); Douglas P. Allen, Lyons, CO (US); Matthew J. Huddleston, Blacklick, OH (US); Delbert Ted Leimbach, Goose Creek, SC (US); Cecil R. Robinson, Hilliard, OH (US); E. Dale VanHoose, Columbus, OH (US); Thomas J. Ward, Grandview Heights, OH (US); Marty J. Warnecke, Grandview Heights, OH (US)

(73) Assignee: Origin Medsystems, Inc., Santa Clara, CA (US)

( * ) Notice: Subject to any disclaimer, the term of this patent is extended or adjusted under 35 U.S.C. 154(b) by 0 days.

(21) Appl. No.: 10/384,250

(22) Filed: Mar. 6, 2003

(65) Prior Publication Data

US 2003/0153932 A1 Aug. 14, 2003

Related U.S. Application Data

(62) Division of application No. 09/641,284, filed on Aug. 17, 2000, now Pat. No. 6,565,581, which is a continuation-in-part of application No. 09/200,796, filed on Nov. 27, 1998, now Pat. No. 6,254,617, which is a division of application No. 08/714,615, filed on Sep. 16, 1996, now Pat. No. 5,868,763.
(60) Provisional application No. 60/150,033, filed on Aug. 20, 1999.

(51) Int. Cl.⁷ .............................................. A61B 17/08
(52) U.S. Cl. ........................ 606/153; 606/213; 128/898
(58) Field of Search ................................. 606/153, 213, 606/215, 219, 220; 128/898

(56) References Cited

U.S. PATENT DOCUMENTS 3,155,095 A   11/1964   Brown ........................ 128/334

(Continued)

FOREIGN PATENT DOCUMENTS

DE   E28 22 603 A1   11/1979

(Continued)

OTHER PUBLICATIONS

C.A.F. Tulleken et al., "End–to–end anastomosis of small (Continued)

Primary Examiner—Anhtuan T. Nguyen
Assistant Examiner—Bradford C Pantuck
(74) Attorney, Agent, or Firm—Law Office of Alan W. Cannon

(57) ABSTRACT

An anastomosis is performed using a flexible mounting structure mounted on the outside of at least one vessel. Fasteners extend through the vessel and are bent towards the incision to attach the flexible mounting structure to the vessel in a manner that controls the edge of the vessel adjacent to the incision. The mounting structures are oriented on each vessel so fasteners on one mounting structure interdigitate with fasteners on the other mounting structure at the location of contact between the vessels when the two vessels are brought together. This creates two complementary sinusoidal-shaped vessel edges with peaks of one edge being accommodated in the valleys of the other edge. The peak-to-valley orientation forms a sinusoidal-shaped joint which is leak free. The fasteners are spaced so proper pressure is applied to the tissue to promote healing without leaking. Furthermore, the fasteners are sized and shaped to properly engage the tissue and bend in a desired manner. Methods and tools for carrying out the anastomosis according to the invention are also disclosed. Methods for forming the fastener and the tines having the proper characteristics are disclosed. An absorbable ring-shaped stent is also disclosed.

4 Claims, 59 Drawing Sheets

U.S. PATENT DOCUMENTS

| | | |
|---|---|---|
| 3,166,072 A | 1/1965 | Sullivan, Jr. |
| 3,254,650 A | 6/1966 | Collito |
| 3,258,012 A | 6/1966 | Nakayama et al. |
| 3,606,888 A | 9/1971 | Wilkinson |
| 3,657,744 A | 4/1972 | Ersek ................................ 3/1 |
| 3,683,926 A | 8/1972 | Suzuki ........................ 606/153 |
| 3,774,615 A | 11/1973 | Lim et al. |
| 3,908,662 A | 9/1975 | Razgulov et al. |
| 3,938,528 A | 2/1976 | Bucalo ........................ 128/334 |
| 3,973,570 A | 8/1976 | Razgulov et al. ........... 128/337 |
| 3,974,835 A | 8/1976 | Hardy, Jr. |
| 3,993,078 A | 11/1976 | Bergentz et al. ............ 128/334 |
| 4,055,186 A | 10/1977 | Leveen ........................ 128/334 |
| 4,214,586 A | 7/1980 | Mericle |
| 4,214,587 A | 7/1980 | Sakura |
| 4,233,981 A | 11/1980 | Schomacher |
| 4,345,600 A | 8/1982 | Rothfuss ..................... 128/334 |
| 4,368,736 A | 1/1983 | Kaster ........................ 128/334 |
| 4,474,181 A | 10/1984 | Schenck |
| 4,523,592 A | 6/1985 | Daniel |
| 4,587,202 A | 5/1986 | Borysko ...................... 430/320 |
| 4,657,019 A | 4/1987 | Walsh et al. |
| 4,676,245 A | 6/1987 | Fukuda |
| 4,681,110 A | 7/1987 | Wiktor ........................ 128/343 |
| 4,747,407 A | 5/1988 | Liu et al. |
| 4,777,096 A | 10/1988 | Borysko ...................... 428/571 |
| 4,787,386 A | 11/1988 | Walsh et al. ................. 128/334 |
| 4,872,874 A | 10/1989 | Taheri ............................ 623/1 |
| 4,873,975 A | 10/1989 | Walsh et al. |
| 4,899,744 A | 2/1990 | Fujitsuka et al. |
| 4,930,502 A | 6/1990 | Chen |
| 4,930,674 A | 6/1990 | Barak ......................... 128/179 |
| 4,950,283 A | 8/1990 | Dzubow et al. ............. 606/216 |
| 4,957,499 A | 9/1990 | Lipatov et al. ............. 606/153 |
| 4,979,954 A | 12/1990 | Gwathmey et al. ......... 606/219 |
| 4,997,439 A | 3/1991 | Chen |
| 5,035,702 A | 7/1991 | Taheri ........................ 606/153 |
| 5,037,428 A | 8/1991 | Picha et al. |
| 5,057,401 A | 10/1991 | Borysko et al. ............ 430/320 |
| 5,078,735 A | 1/1992 | Mobin-Uddin ................ 623/1 |
| 5,089,008 A | 2/1992 | Chen |
| 5,123,908 A | 6/1992 | Chen |
| 5,188,638 A | 2/1993 | Tzakis |
| 5,234,447 A | 8/1993 | Kaster et al. |
| 5,250,057 A | 10/1993 | Chen |
| 5,263,973 A | 11/1993 | Cook |
| 5,336,233 A | 8/1994 | Chen |
| 5,366,462 A | 11/1994 | Kaster et al. ............... 606/153 |
| 5,403,333 A | 4/1995 | Kaster et al. ............... 606/153 |
| 5,486,187 A | 1/1996 | Schenck |
| 5,501,689 A | 3/1996 | Green et al. |
| 5,562,690 A | 10/1996 | Green et al. |
| 5,653,743 A | 8/1997 | Martin ....................... 606/153 |
| 5,683,453 A | 11/1997 | Palmaz ....................... 606/153 |
| 5,693,454 A | 12/1997 | Munoz |
| 5,695,504 A | 12/1997 | Gifford, III et al. ........ 606/153 |
| 5,702,048 A | 12/1997 | Eberlin |
| 5,707,380 A | 1/1998 | Hinchliffe et al. |
| 5,720,755 A * | 2/1998 | Dakov ........................ 606/139 |
| 5,741,274 A | 4/1998 | Lenker et al. .............. 606/142 |
| 5,752,966 A | 5/1998 | Chang ........................ 606/151 |
| 5,762,811 A | 6/1998 | Munoz ........................ 216/11 |
| 5,792,180 A | 8/1998 | Munoz ....................... 606/223 |
| 5,868,763 A | 2/1999 | Spence et al. ............. 606/153 |
| 5,879,371 A | 3/1999 | Gardiner et al. ........... 606/224 |
| 5,904,697 A | 5/1999 | Gifford et al. ............. 606/155 |
| 5,938,696 A | 8/1999 | Goicoechea et al. ........... 623/1 |
| 5,957,973 A | 9/1999 | Quiachon et al. .............. 623/1 |
| 5,976,159 A | 11/1999 | Bolduc et al. .............. 606/142 |
| 5,976,178 A | 11/1999 | Goldsteen et al. ............. 623/1 |
| 6,030,392 A * | 2/2000 | Dakov ........................ 606/139 |
| 6,068,637 A | 5/2000 | Popov et al. ............... 606/159 |
| 6,176,413 B1 * | 1/2001 | Heck et al. ............... 227/176.1 |
| 6,241,742 B1 | 6/2001 | Spence et al. ............. 606/153 |

FOREIGN PATENT DOCUMENTS

| | | |
|---|---|---|
| DE | 2822603 A1 | 11/1979 |
| DE | 297 13 335 U1 | 11/1997 |
| EP | 0539237 A1 | 10/1992 |
| GB | 1181563 | 2/1967 |
| WO | WO 95/17127 | 6/1995 |
| WO | WO 95/17128 | 6/1995 |
| WO | WO 95/35065 | 12/1995 |
| WO | WO 98/02099 | 1/1998 |
| WO | WO 98/19630 | 5/1998 |
| WO | WO 99/21491 | 5/1999 |

OTHER PUBLICATIONS vessels using an ND:YAG laser with a hemispherical contact probe", Technical Note, J. Neurosurg., vol. 76, Mar. 1992, pp. 546–549.

Robin H. Heijmen, M.D., et al. "A Novel One–Shot Anastomotic Stapler Prototype for Coronary Bypass Grafting on the Beating Heart: Feasibility in the Pig", Journal of Thoracic and Cardiovascular Surgery, Jan. 1999, pp 117–125.

* cited by examiner

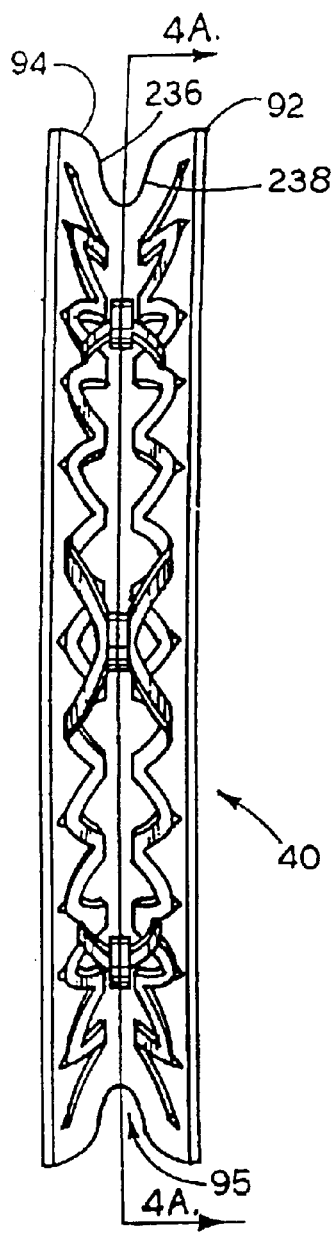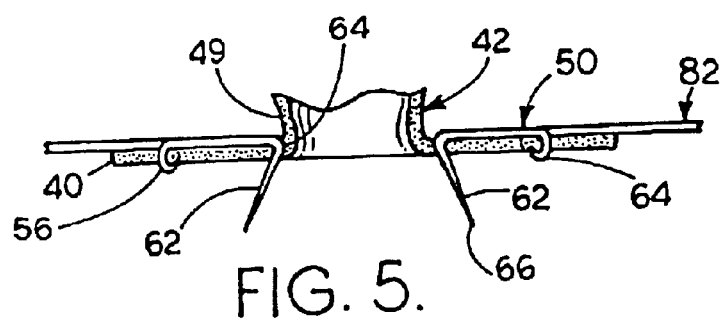
FIG. 4.
FIG. 5.

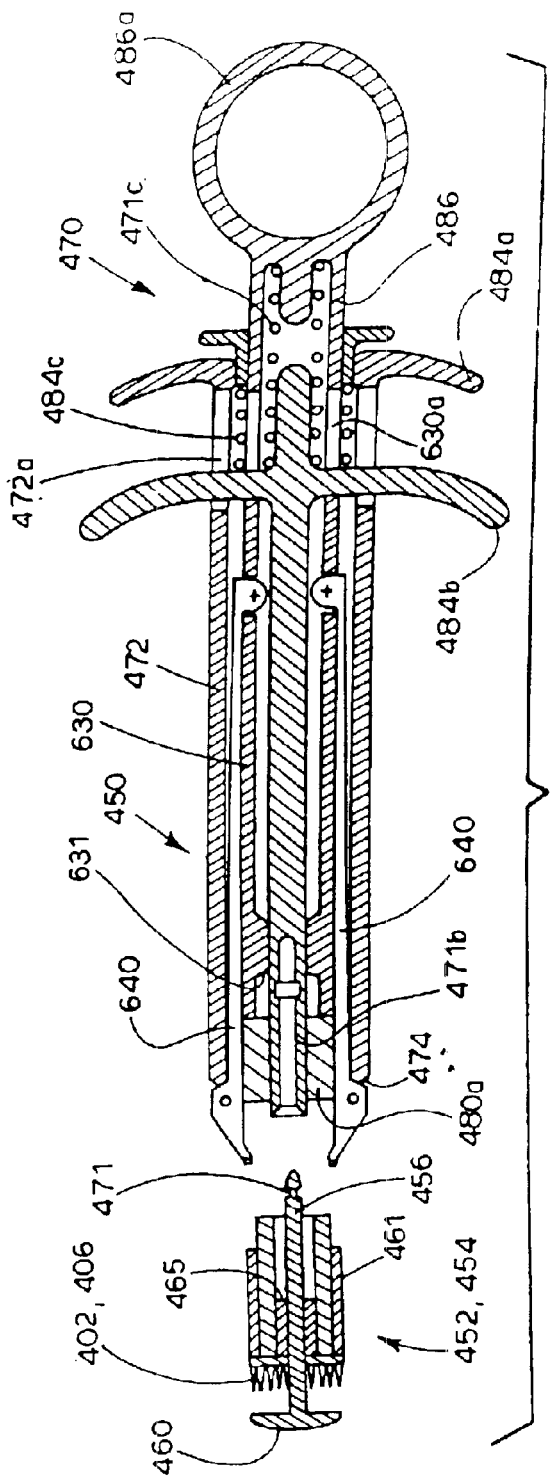
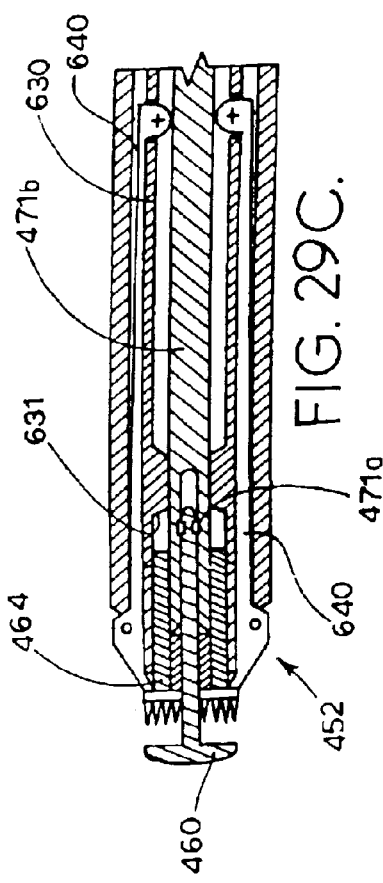
FIG. 29B.
FIG. 29C.

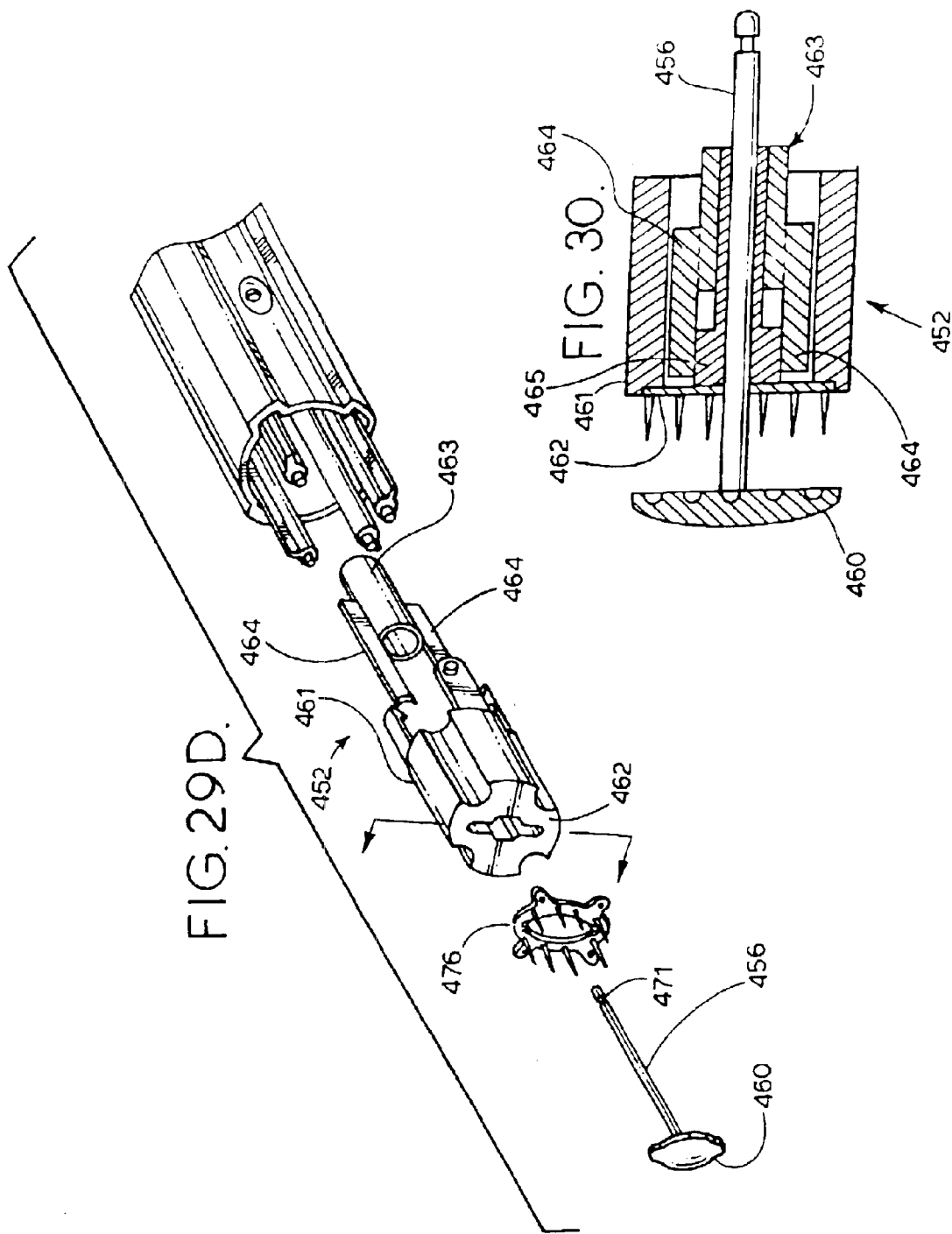

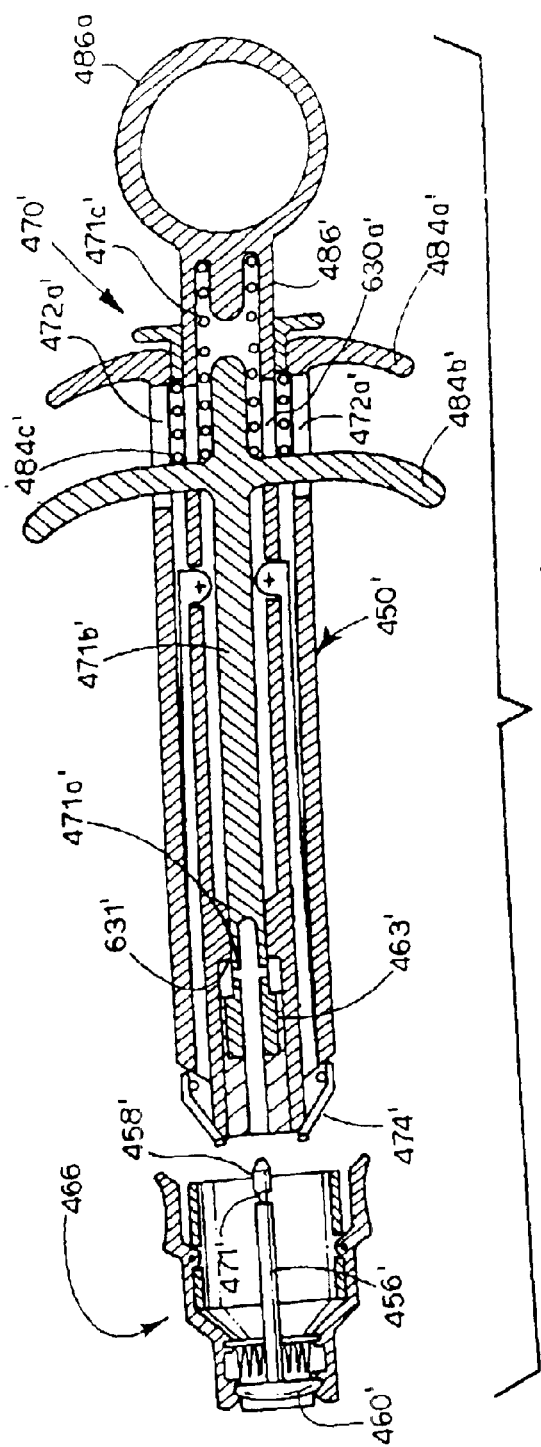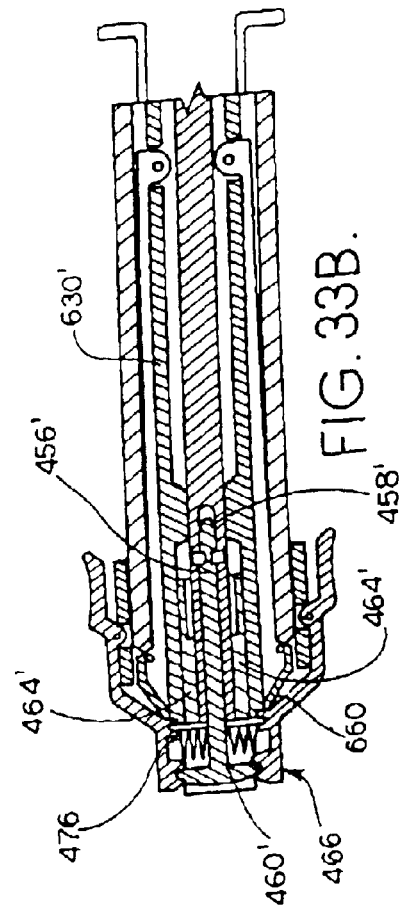
FIG. 33A.
FIG. 33B.

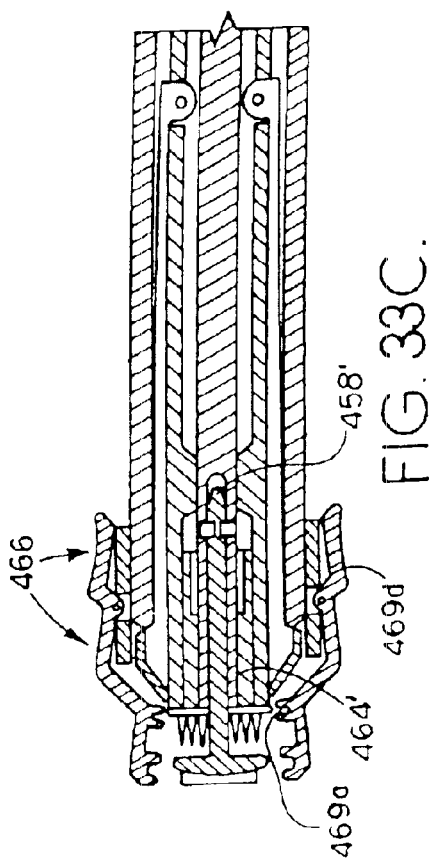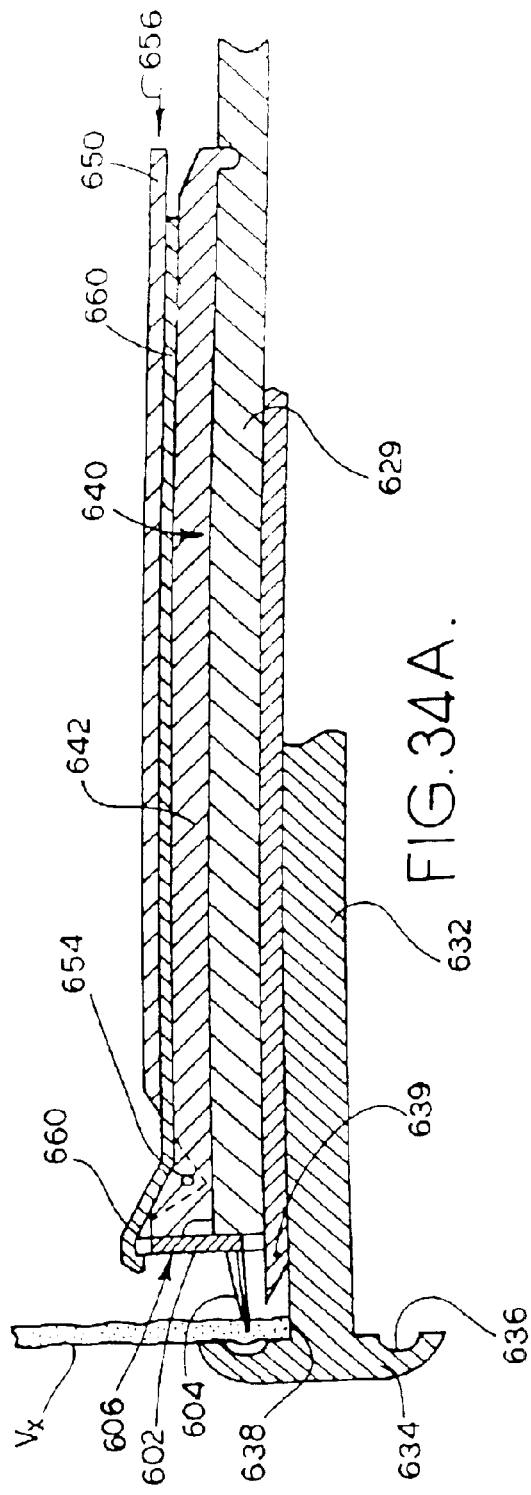

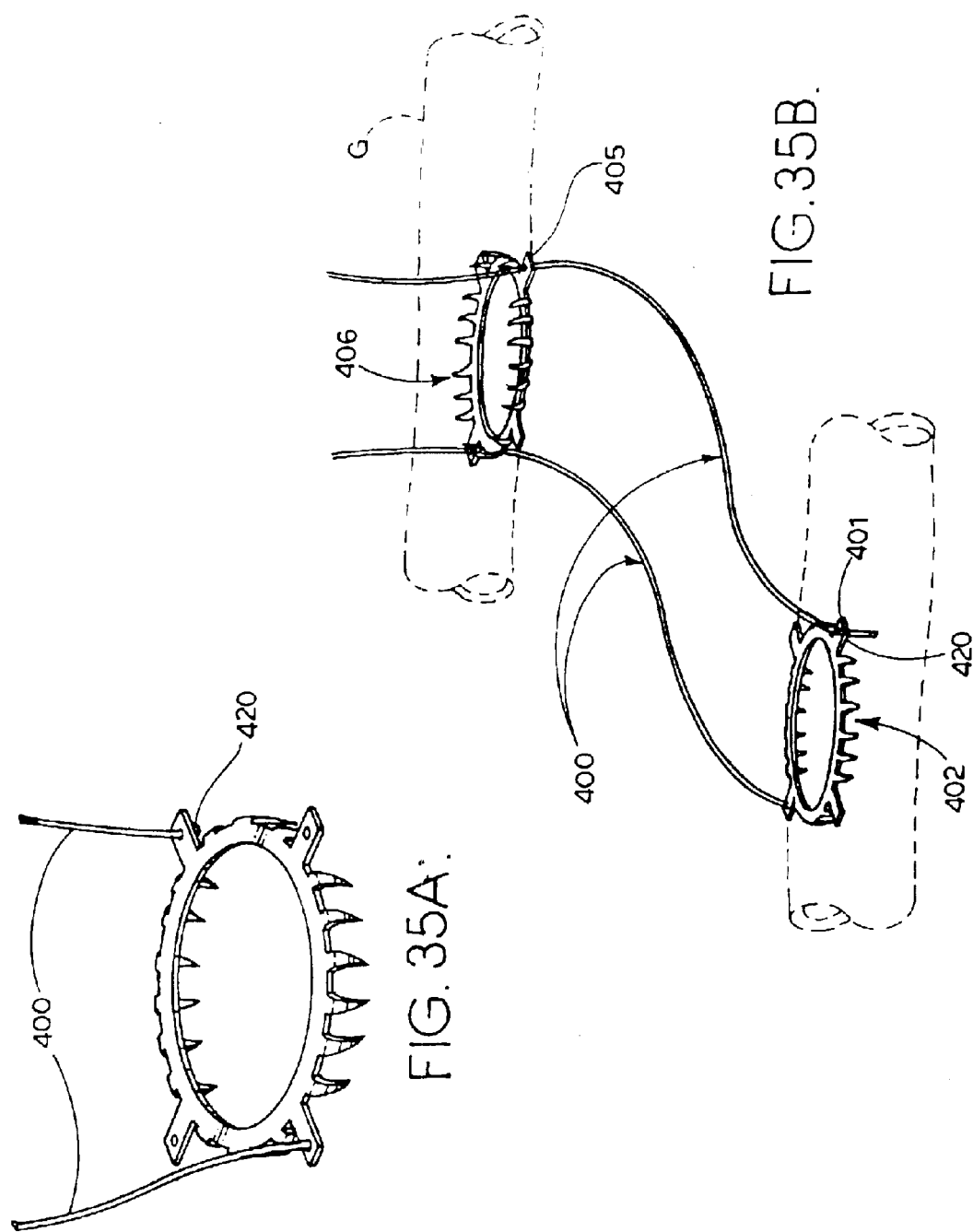

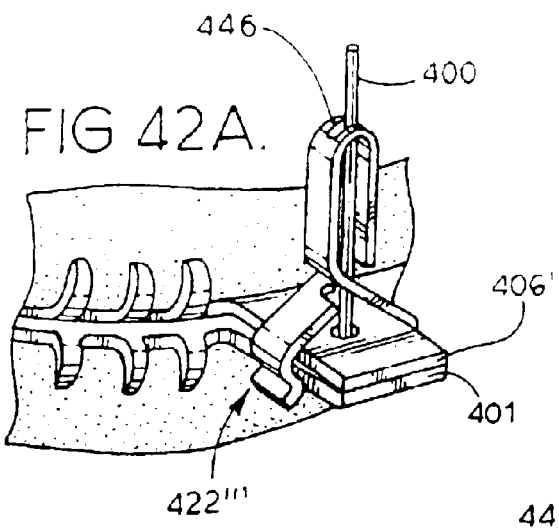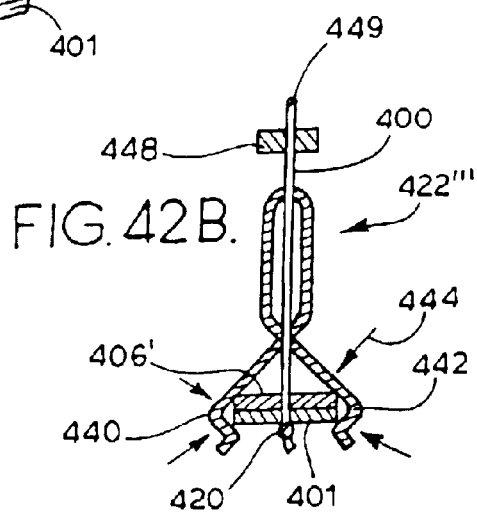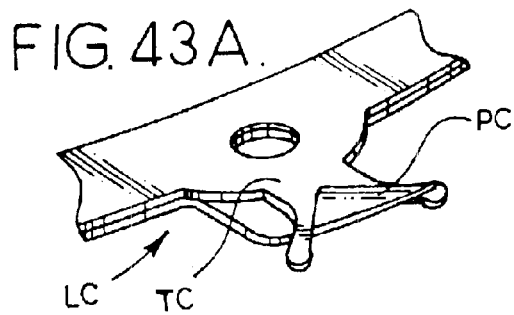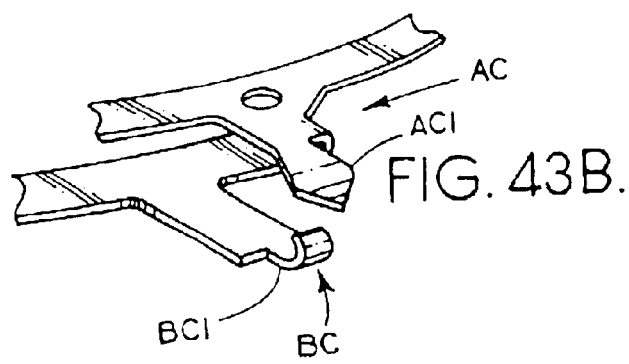

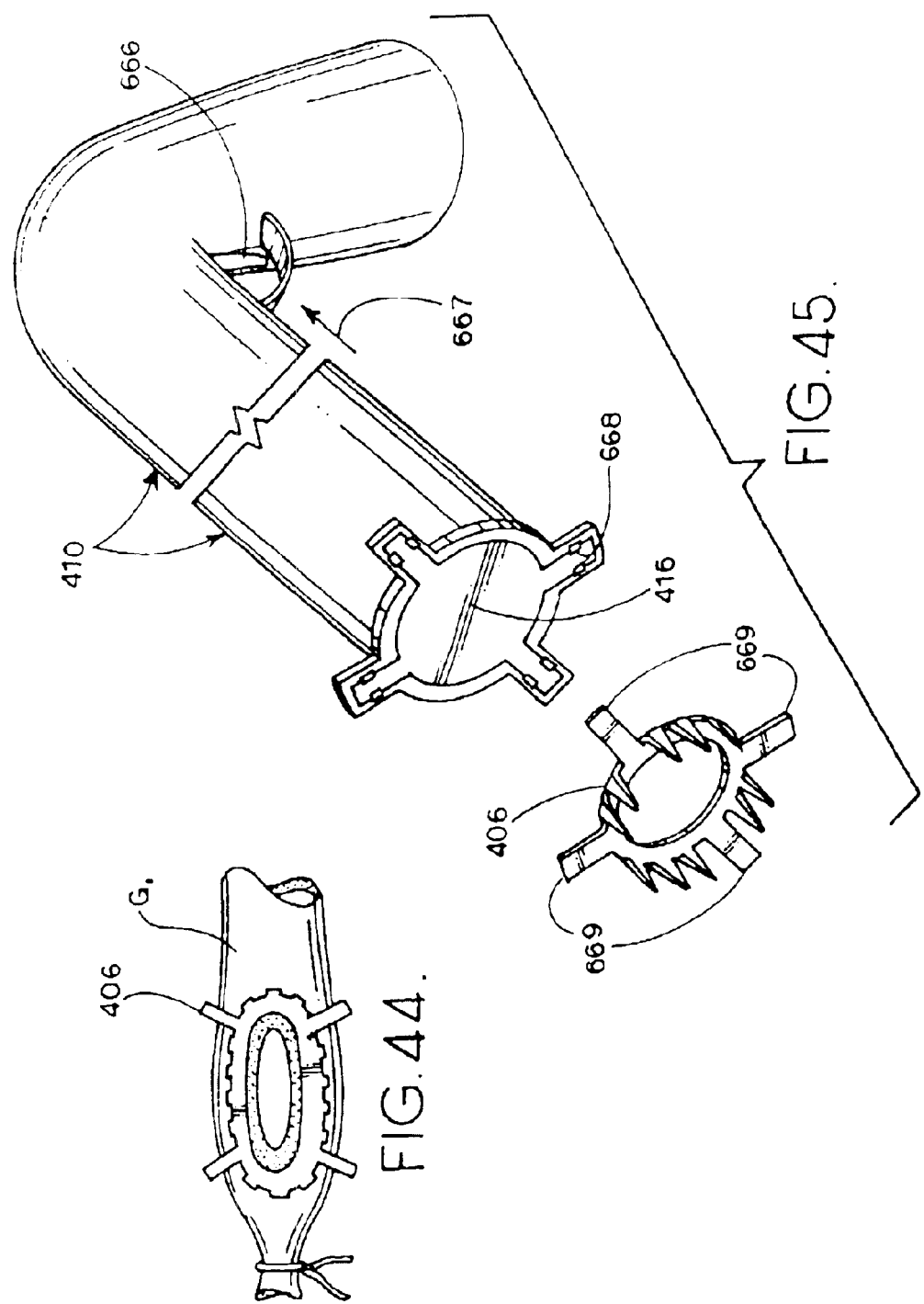

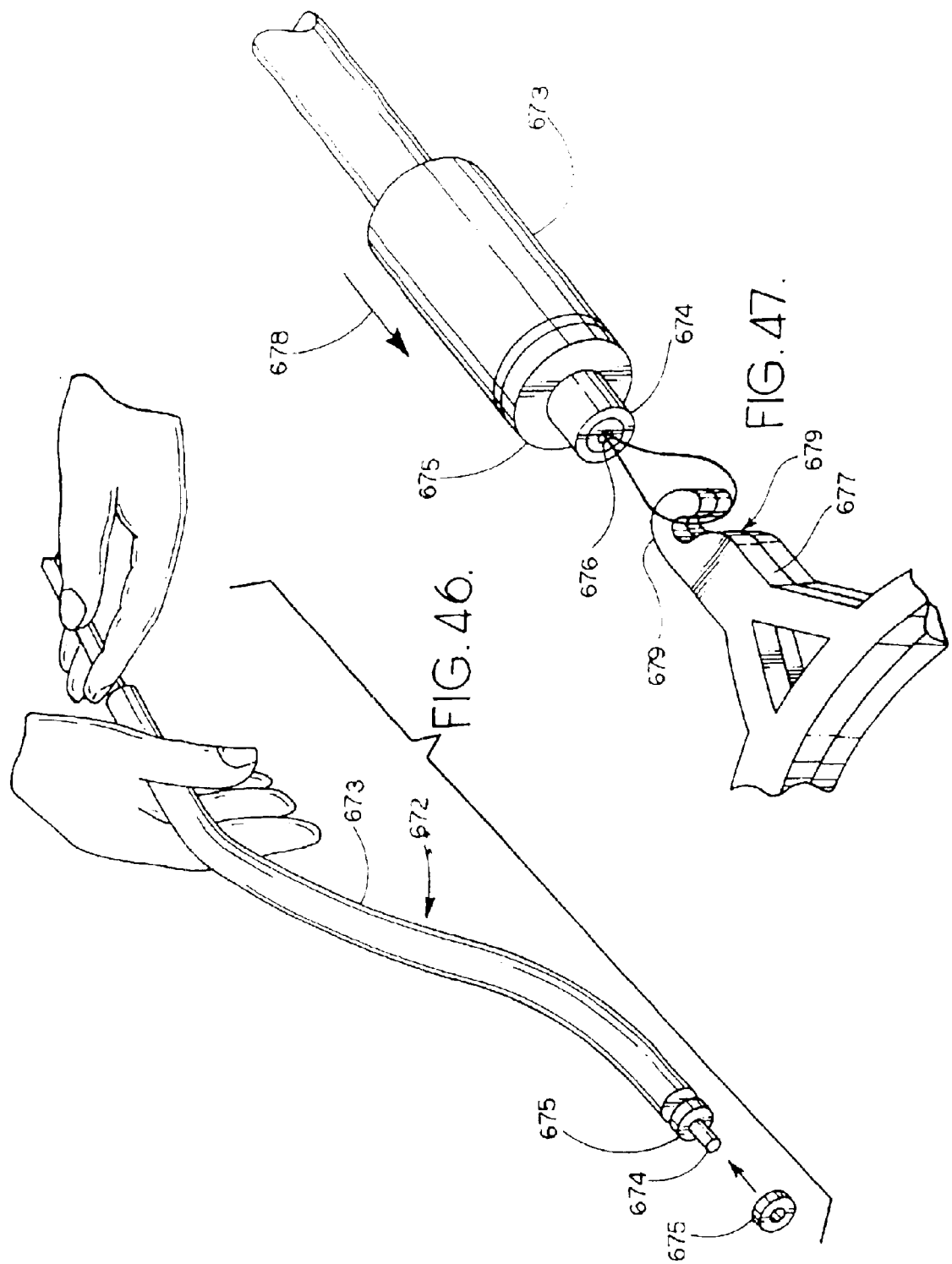

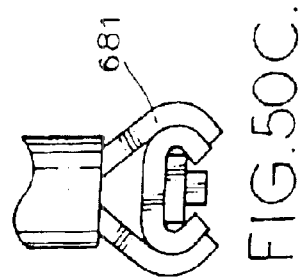
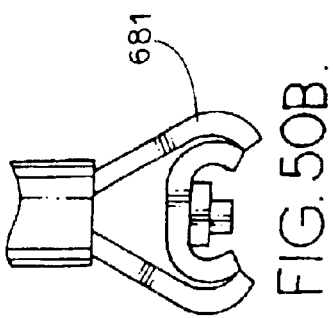
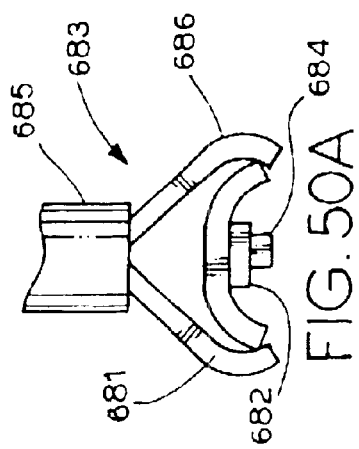
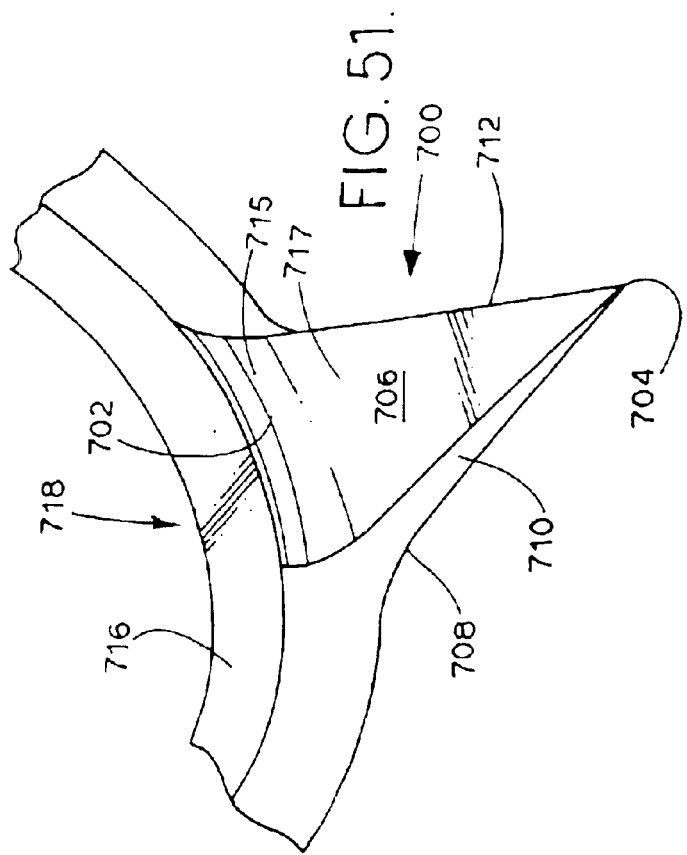

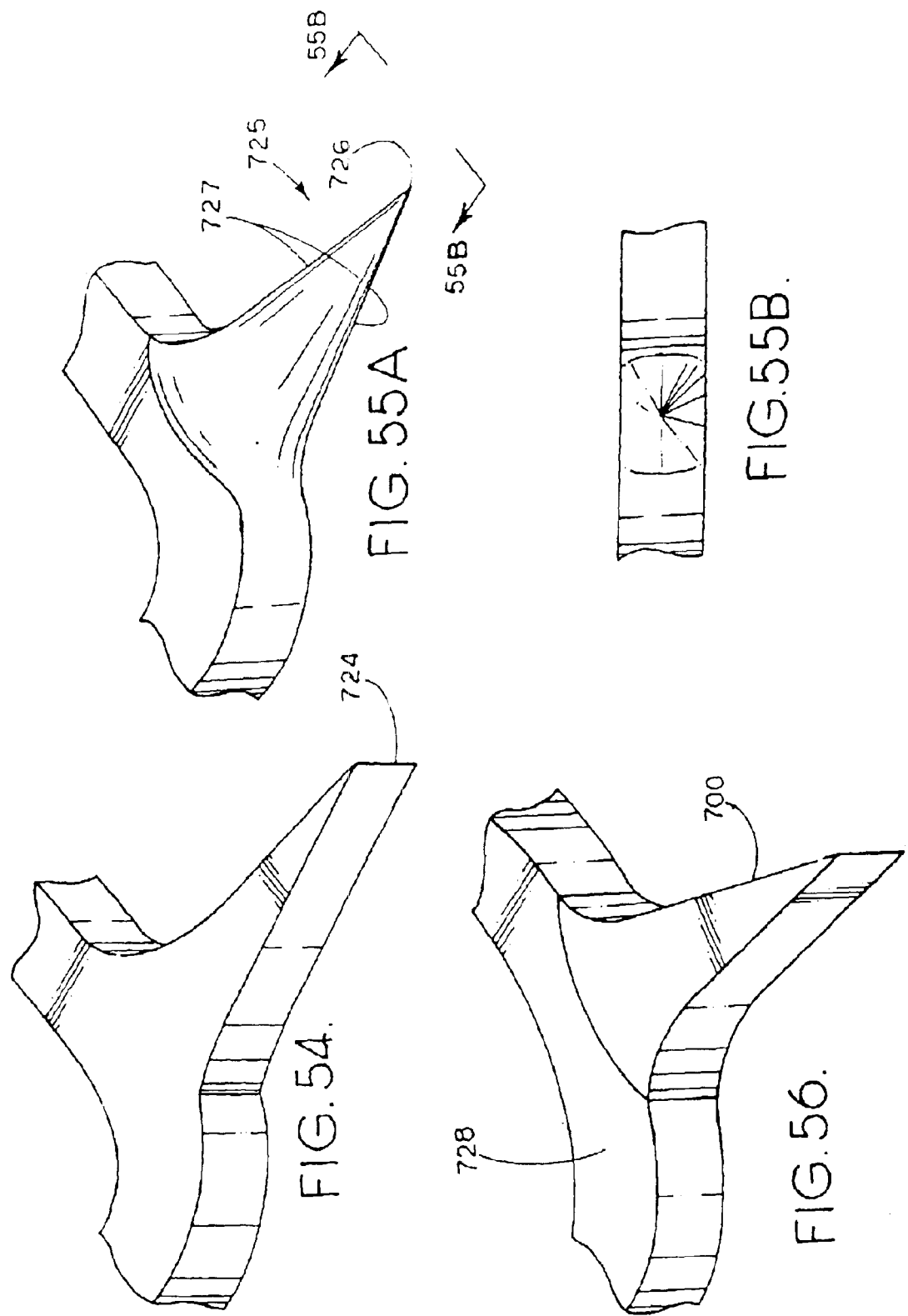

APPARATUS AND METHOD FOR PERFORMING AN ANASTOMOSIS

CROSS REFERENCE TO RELATED APPLICATIONS

This application is a division of application Ser. No. 09/641,284, filed Aug. 17, 2000, now U.S. Pat. No. 6,565,581, which in turn claims the benefit of provisional application Ser. No. 60/150,033 filed Aug. 20, 1999 and which is a continuation-in-part of application Ser. No. 09/200,796, filed Nov. 27, 1998, now U.S. Pat. No. 6,254,617, which is a division of application Ser. No. 08/714,615, filed Sep. 16, 1996, now U.S. Pat. No. 5,868,763.

TECHNICAL FIELD OF THE INVENTION

The present invention relates to the general art of surgery, and to the particular field of anastomosis.

BACKGROUND OF THE INVENTION

In the United States, there are currently as many as 300,000 coronary artery bypass graft (CABG) procedures performed on patients annually. Each of these procedures may include one or more graft vessels which are hand sutured. Until recently, coronary artery bypass procedures have been performed with the patient on cardiopulmonary bypass whereby the heart is stopped with cardioplegia and the surgery is performed on an exposed, stationary heart.

The vast majority of CABG procedures currently performed are accomplished by opening the chest wall to gain access to the coronary vessels. Through the use of heart lung bypass machines and a drug to protect the heart muscle, the heart is stopped and remains still during the procedure. In this setting, the surgeon has ample time and access to the vessels to manipulate hand suturing instruments such as forceps, needle holders and retractors.

However, with increasing costs of hospital stays and increased awareness by patients of other minimally invasive surgical procedures, interest in developing a minimally invasive CABG procedure is increasing. Hospitals need to reduce costs of procedures and patients would like less post-operative pain and speedier recovery times.

In the past, two significant developments in technology played a major role in advancing the whole area of cardiac surgery. The heart-lung machine was invented in the 1950's and underwent significant improvement in design to become a reliable clinical device in the 1960's. The heart-lung machine allows the surgeon to take the heart out of the blood circulation system to work on it in isolation.

The second major development was in myocardial protection. When the heart is isolated from the circulation, it is no longer perfused. After twenty to thirty minutes of ischemia, irreparable damage may occur and no matter how good the repair, the heart function may be inadequate to allow the patient to survive. The development of cardioplegia, a solution which is generally cold and high in potassium, changed everything. This development occurred in the 1970's. Cardioplegia allows very satisfactory protection of the heart so the surgeon can perform an unhurried repair and still expect the heart to work afterward.

An unforeseen consequence of these technology developments was the decline in interest in technology to facilitate and expedite heart surgery. When speed of the surgery was of utmost importance, many developments were proposed to speed surgery. Therefore, while the art in the 1960's and 1970's contained numerous examples of devices intended to expedite heart-related surgery, the incidence of such devices declined after about 1970.

With an increased incentive to reduce costs, there is a renewed interest in expediting cardiothoracic procedures. A few pioneering surgeons are now performing minimally invasive procedures in which the coronary artery bypass is performed through a small incision in the chest wall. There are some surgeons that believe that the best way to perform a minimally invasive coronary artery bypass procedure is to perform the procedure on a beating heart, i.e., without heart-lung bypass and cardioplegia. This minimizes the time it takes to perform the procedure, reduces the cost of the operation by eliminating the heart lung bypass machine and reduces recovery time.

In the case of minimally invasive procedures on a beating heart, the surgeon starts by making a mini-thoracotomy between the fourth and fifth ribs and, sometimes, removing the sternal cartilage between the fourth or fifth rib and the sternum. The space between the fourth and fifth ribs is then spread to gain access to the internal mammary artery (IMA) which is dissected from the wall of the chest. After dissection, it is used as the blood supply graft to the left anterior descending artery of the heart (LAD). The pericardium and the heart are located below the IMA. The pericardium is opened exposing the heart. At this point, the LAD may be dissected from the fissure of the heart and suspended with soft ligatures to isolate the artery from the beating heart. A small arteriotomy is performed in the LAD and the graft IMA is sutured to the LAD.

Heretofore, access to the cardiac vessels is gained for this procedure by sawing the sternum in half and separating the chest wall. Although this procedure is currently well perfected, the patient suffers intense pain and generally requires a long recovery period.

Until recently all bypass graft procedures have been performed by hand suturing tiny vessels together with extremely fine sutures under magnification. The skills and instruments required to sew extremely thin fragile vessel walls together have been perfected over the last twenty years and are well known to the surgical community that performs these procedures.

In the "open chest" surgical setting, the surgeon has adequate access and vision of the surgical site to manipulate the anatomy and instruments. However, in minimally invasive procedures, this access is often severely restricted thereby inhibiting such procedures.

Furthermore, the interest in less invasive surgical approaches is promoting concomitant interest in many areas that were abandoned long ago, including coronary fastening and valve replacement. In view of the above-discussed developments, the inventors have thus identified a need for a device and a method to perform CABG surgery on a beating heart.

Some surgeons are attempting minimally invasive CABG procedures using femoral artery bypass access rather than opening the chest for bypass via the aorta. However, since use of cardioplegia requires additional support and expense during the anastomosis procedure, the inventors believe that it is best to attempt to fasten the anastomosis while the heart is beating. However, this procedure when performed with a hand suturing technique is very imprecise due to the translation of movement from the beating heart to the suspended artery. This may cause imprecise placement of the suture needles. Imprecise placement of the sutures may cause a distortion of the anastomosis which may cause stenosis at the junction.

The sutures used for this procedure are extremely fine (0.001" in diameter) and are placed less than 1 mm apart. As one can imagine it is difficult enough to place suture needles the size of a small eyelash into a vessel wall with placement accuracy of better than 1 mm; yet to accomplish this feat of precision on a moving target is even more difficult. To make matters worse the site is often obscured by blood because the heart has not been stopped.

Therefore, there is a need for a means and method which permits the forming of a precise anastomosis without requiring the stopping of a beating heart. Still further, there is a need for performing such an anastomosis in a minimally invasive manner.

The current method of hand suturing has the several drawbacks, including the following.

On a beating heart it may be difficult to place the sutures with the position precision required. In a beating heart procedure the surgeon can attempt to minimize the deleterious effects of the movement by using suspension or retraction techniques. However, it is impossible to isolate all movement of the vessel during an anastomosis procedure.

Methods that attempt to stabilize and isolate an artery from the movement of the beating heart may damage the vessel or cause myocardial injury (MI).

In addition to the problem of accurately placing sutures, an incision through the artery wall to open the artery must be made. This, too, is a delicate procedure even on a still heart because the incision must be of a precise length. It is also critical to not penetrate the back wall or side wall of the vessel which will lead to complications. The placement of the initial incision is of paramount importance. The surgeon must pick a suitable location free from calcium deposits, fat and side branches.

Without cardioplegia, blood flow to the heart muscle must also be provided while the heart is beating; therefore, after the initial arteriotomy the surgical field is very bloody and obscured.

Access to the heart vessels other than the LAD will be extremely difficult with minimally invasive hand suturing due to the anatomical location of the posterior wall of the heart.

Although minimally invasive CABG procedures are taking place now with sutured anastomosis they require superlative skills and are therefore not widely practiced.

One of the most vexing problems is that of adequate access. The procedure takes place through an access site created between two ribs. The ribs cannot be spread too far without risk of breaking and the heart lies deep within the chest. The access is through a small, long, dark tunnel. The surgeon must then manipulate tools down this tunnel without obscuring his or her vision.

If special tools are constructed to allow the surgeon to hold suture needles on the end of a long instrument, the added length of the tool only amplifies any inaccurate manipulation. The same is true for any special suturing devices.

If the sutures are not correctly placed in the vessel walls, bunching or leaks may occur. In the minimally invasive procedure this is disastrous usually resulting in the conversion to an open chest procedure to correct the mistake. Any rough handling of the vessel walls is detrimental as inflammation can cause further postoperative complications.

An anastomosis must be leak tight to prevent exsanguination. Therefore, any improvement over sutures must provide a leak free seal in a very confined space, yet should provide proper flow areas in the vessel after healing is complete.

As can be understood from the above discussion, it is necessary to find a way to control the beating heart-induced movement of the vessel while performing the anastomosis in such a way that still allows for exact placement of a fastening means during a beating heart anastomosis procedure.

While the art contains disclosures of several devices that are used to join blood vessels, these devices are primarily directed to an end-to-end anastomosis, and thus are inadequate for CABG procedures. Furthermore, the techniques taught in the prior art often require the vessels to be severely deformed during the procedure. The deformation may be required to fit the vessels together or to fit a vessel to an anchoring device. One cannot just slit the tissue and pull it through a ring to anchor it on a flange. Pulling or stretching the vessel walls produces a very unpleasant and unexpected result. Vessel walls are made of tissue fibers that run in the radial direction in one layer and the longitudinal direction in another layer. In addition, the elasticity of the tissue fibers in the longitudinal direction is greater than those that run radially. Therefore, the tissue will not stretch as easily in the radial or circumferential direction and results in a narrowing or restriction when pulled or stretched in the prior art devices. Vessel walls also have a layer of smooth muscle cells that can spasm if treated harshly. Such manhandling will result in restrictions and stenotic junctions because the vessel walls will react poorly to being treated in such a rough manner and the stretching of the vessel wall will telegraph up the vessel wall due to the high radial stiffness of the vessel structure causing restrictions and spasms in the vessel wall. The prior art fails to teach that the vessels are living tissue and must not be made to conform to rigid fitting-like shapes. Therefore, there is a need for an anastomotic technique that permits handling of blood vessels in a manner that is not likely to cause those blood vessels to react in an undesirable manner Additionally, the prior art fails to teach methods of ensuring hemostasis so there is no leakage under pressure. It is noted that mechanical devices used to join blood vessels are extremely difficult to seal. Prior art devices are generally directed to accomplishing hemostasis through excessive clamping forces between clamping surfaces or stretching over over-sized fittings.

In order to effect good healing, healthy vessel walls must be brought into intimate approximation. This intimate approximation is now accomplished using sutures. A vascular surgeon is taught how to suture by bringing the vessel edges together with just the right knot tightness. A knot that is too loose may cause the wound to leak and have trouble healing causing excessive scar tissue to form. A knot that is too tight may tear through the delicate tissue at the suture hole causing leaks. The key is to bring the edges together with just the right amount of intimate approximation without excessive compression.

It is further noted that the junctions taught in the prior art are not anatomically correct both for blood flow and for healing. A well made anastomotic junction is not made in a single plane and should accurately follow blood vessel geometry. The junction is more of a saddle shape and the cross section is not necessarily a circle. The junction where the vessel units join is not a constant cross section angle but an angle that varies continuously throughout with respect to any linear reference. In addition, the length of the junction should be many times the width of the opening in order to ensure a low blood flow pressure gradient in the junction and to establish a proper flow area. In fact the best results are obtained if the confluence area is actually oversized. The prior art junctions do not account for such flow characteristics and parameters and are thus deficient. Therefore, there is a need for an anastomotic technique which can establish proper flow characteristics and parameters and that accurately preserves blood vessel geometry, specifically the plural planar nature in which the junction occurs. Furthermore, most anastomoses are made between vessels that are not similar in size. It is therefore necessary to provide a means and method which allow for the accommodation and joining of dissimilarly sized vessels.

In addition, the inventors have found through post surgical follow-up that the supply vessels grow in diameter to accommodate their new role in providing oxygenated blood to the heart; therefore, there is a need to provide an oversized junction to accommodate any increase in the dimension of the graft vessel size. With a rigid ring that has a singular circular cross section of the graft, the fitting does not allow the vessel to provide this increase in flow as the vessels expand to meet the needs of the heart muscle. Still further, the inside lining of the vessel walls (intima) should make contact with each other to have proper healing. The walls of the vessels must come together with just the right amount of approximation to promote good healing. If the incised edges are too far apart scarring will occur causing restrictions. The walls cannot be compressed between two hard surfaces which will damage the vessels. The prior art teaches plumbing-like fittings clamped onto vascular structures. However, clamping and compressing the vessel walls too tightly may cause necrosis of the vessel between the clamps. If necrosis occurs the dead tissue will become weak and most likely cause a failure of the joint. Still further such rings and tubes used to clamp vessels together do not follow the correct anatomical contours to create an unrestricted anastomosis. Failing to account for the way healing of this type of junction occurs and not accounting for the actual situation may cause a poor result. A suture technique has the advantage of having the surgeon making on-the-fly decisions to add an extra suture if needed to stop a leak in the anastomosis. In a mechanical minimally invasive system it will not be possible to put an "extra suture throw" in so the system must provide a way to assure complete hemostasis. Being a mechanical system the approximation will not be 100% perfect. And since the design errs on the side of not over-compressing the tissue there may be very small areas that may present a leak between the edges of the vessel walls. Accordingly healing with prior art techniques using mechanical joining means is not as efficient as it could be. Therefore, there is a need for an anastomotic technique that accounts for the way healing actually occurs and provides proper structural support during the healing process.

When vascular integrity is interrupted, the body quickly reacts to reestablish hemostasis. Circulating blood platelets are quickly mobilized to the injury site and initiate and support the coagulation sequence that leads to the formation of a fibrin plug at the site of injury. Large breaks in vessel walls which are under pressure cannot be effectively sealed by platelets and fibrin without a substrate to collect on. It is critical that the junction of an anastomosis bring two healthy vessel surfaces in close approximation to provide an optimal region for vessel repair and healing, minimizing the distance between healthy endothelial cells on either side of the junction. This allows for the natural control processes which prevent platelet aggregation from extending beyond the area of injury. A more detailed description of the clot limiting process and the healing process can be found in various reference texts, such as "Coagulation: The Essentials", by Fischbach, David P and Fogdall, Richard P, published by Williams and Wilkins of Baltimore in 1981, the disclosure of Chapter 1 thereof being incorporated herein by reference.

Still further, some vessels are located or sized in a manner that makes placing elements thereon difficult. In such a case, the fewer elements used to perform an anastomosis the better. Therefore, there is a need for a means and a method for performing an anastomosis that can be effected without the need of a hemostatic medium.

Many times, when a CABG operation is undertaken, the patient has multiple clogged arteries. At the present time, the average number of grafts is 3.5 per operation. When multiple grafts are performed, there is sometimes the opportunity to use an existing or newly added supply vessel or conduit for more than one bypass graft. This is known as a jump graft whereby the conduit at the distal end thereof is terminated in a side-to-side anastomosis first, with an additional length of conduit left beyond the first junction. Then, an end of the conduit is terminated in an end-to-end junction. This saves time and resources and may be necessary if only short sections or a limited amount of host graft material is available.

At the present time, existing means and methods of performing an anastomosis do not permit the formation of multiple anastomotic sites on a single graft vessel at both proximal and distal ends. Thus a surgeon will have to use multiple tools to perform multiple anastomoses. This will be either impossible or very expensive.

Therefore, there is a need for a means and a method for performing an anastomosis which will lend itself to efficient and cost-effective multiple by-pass techniques. There is also a need for a means and a method for performing an anastomosis which will lend itself to efficient and cost-effective jump graft techniques.

As discussed above, performing a sutured anastomosis in a minimally invasive manner while the patient's heart is beating requires an extremely high degree of skill and dexterity. Any instrument used in such a procedure must therefore be as easy and efficient to use as possible whereby a surgeon can focus most of his attention on the anastomosis site. The instrument should thus reflect the above-discussed needs as well. Still further, any instrument used in such a procedure must be amenable to efficient manufacture.

The parent applications, incorporated herein by reference and which will be referred to as the parent disclosures, disclose an apparatus and method for forming a precise and anatomically accurate anastomosis on a patient without requiring the patient's heart to be stopped. The means of the parent disclosures includes an instrument that precisely places fasteners on the outside surface of a blood vessel in a position to cause the anastomosis to have the proper flow area and to accurately reflect the geometry of the junction. The means of the parent disclosures further position the inside edges of the two incised blood vessels forming the anastomosis in abutting contact with each other whereby proper healing is promoted.

The present invention amplifies the edge-positioning feature of the parent disclosures so the joint formed is leak free and is anatomically accurate whereby proper healing is promoted. This is still achieved in a minimally invasive surgery situation where proper control of the incised vessels can be difficult to achieve, especially when the patient's heart is beating during the procedure, and does not require a hemostatic medium.

Still further, the accurate and precise control of the vessel walls should be carried out in the most efficient manner in order to most efficiently complete the procedure.

Therefore, there is a need for a means and a method for performing an anastomosis in a minimally invasive manner that fulfills the objectives set forth in the parent disclosures and does so in an efficient manner that forms an accurate and precise joint that is as leak free as possible, even without a hemostatic medium.

As can be understood from the above disclosures, the targets and elements used in performing an anastomosis are often very small. Still further, the procedure will be performed in a very difficult sight area. These two situations combine to make proper alignment of the vessels extremely difficult. However, proper alignment is a necessity.

Therefore, there is a need for a means and a method for properly aligning two vessels during a minimally invasive surgical procedure.

As discussed above and in the parent disclosures, the joint of an anastomosis is formed when the two malleable ring-shaped stents are brought together and attached. An important factor for success for a mechanical anastomotic device is how the tissue is approximated to prevent leaks and to allow the tissue to heal without inflammation or thrombosis, which can lead to a thickening or stenosis at the joint. Thus, the inventors have found that tissue compression at the joint site is important but has not been considered in the prior art. As noted above, it is important not to "over compress" the joint, yet at the same time, the joint must not leak more than a couple of milliliters per minute under physiological blood pressures to allow the natural clotting process to seal any small leaks quickly, after the joint has been formed.

These conflicting considerations present a significant problem. While it might appear to be best to clamp the joint tightly together to prevent leaks, too much force clamping the tissue is not desirable because the tissue healing response is altered by crushing forces. As tissue is crushed or "over compressed", certain chemical activators are released which can cause blood platelets to aggregate. In addition, injured tissue cells expose a phospholipid surface upon which the clotting cascade coagulation factors interact to form a clot. An otherwise patent anastomosis can be occluded due to an excessive release of clotting factors resulting from a compression injury. There are natural inhibitors to platelet aggregation (prostacyclin) and clot formation, produced when an activated platelet comes in contact with normal vessel wall. Therefore it is important to design a joint that in addition to being virtually leak free, will provide an atraumatic-sealing configuration and present normal tissue and minimal foreign material to the interior of the blood vessel.

The parent disclosures disclose malleable mounting structures having fastening elements thereon for attaching the mounting structures to a vessel. These fastening elements include a body having one end attached to a ring and a tip on the other end. The fasteners are formed by forcing them against arcuate grooves in a manner that is intended to turn the fastener on itself in the manner of a staple. However, the inventors have found that it is important to control the fastener such that when it is engaged with the arcuate groove, it will deform in the desired manner rather than simply fold or crumple.

Therefore, there is a need for a means for controlling the formation of the fastening means disclosed in the parent disclosures to ensure that they will bend in the desired manner.

In the parent disclosures a joint was established using the concepts of fasteners or tines, mounted on a malleable ring-shaped stents. These tines are used to bring the internal layers of the vessel wall to the surface of the malleable ring-shaped stents. In addition, several of the embodiments have employed a hemostatic media externally to promote sealing of any blood at the joint. The inventors have discovered that by staggering the tines on one ring relative to another ring, the tines form the tissue between each other. This interdigitation of the tines reduces leakage to an absolute minimum. An acceptable leak rate is less than 2 ml/min at 200 mm/Hg. However, staggering the tines is not the only factor that contributes to stopping joint leakage, the shape and surface quality of the tines itself also contributes to reducing the leak rate at the joint. The inventors have also discovered the known manufacturing processes produce 90° sharp edges. 90° sharp edges tend to cut through tissue allowing relatively large pathways in which blood leaks through the tine holes. This is mainly due to EDM (electrode discharge machine) or chemical etching methods, which produce a dead sharp edge. Both processes orientate themselves perpendicular to the material that will be machined leaving the sharp edges as a byproduct. Traditional secondary operations used to remove the sharpness from the elements include electropolishing and mechanical deburring. Electropolishing removes extremely small amounts of material from the entire part at the same time. The object to be electropolished is submersed into a chemical bath that is electrically charged thereby uniformly removing small amounts of material on the outer surface of the part. If applied to the malleable stents of interest, it would round the fasteners in an acceptable manner but the tips of the tines would become dull and, unable to pierce the vessel wall and the malleable stent would become too weak from the amount of material which has been removed. Also, the malleable stent would not be perfectly planar due to the inconsistent nature of electropolishing. The deburring process also removes a small amount of material from a part. There are different ways to deburr. One way is a batch process in which many parts are loaded into a rotating container similar to a clothes dryer. A granular abrasive media is added with the parts and the container begins to spin. The media slowly removes any burrs and rounds the edges of the parts. The problem with this process is the parts must be stiff enough to withstand the tumbling effect, and not be bent or deformed by the process. Also parts such as those of interest may tangle with each other when removed making it difficult to separate the parts without damage thereto. Furthermore this type of deburring is not a precision operation. Thus, for the product of interest, some tines may be sharper or thinner than others thereby adversely affecting not only the ability of the joint to be leak-free but also compromising the deployment of the malleable stent on the vessel. Another method of deburring is a manual operation with each malleable stent being individually blasted with a precision instrument. However, the parts may be inconsistent.

Thus, there is a need for a process that can be used to form malleable stents useful in the anastomosis process of interest and which can uniformly remove sharp edges on tines without dulling the tine tip and without removing any material from the malleable body and yet still be cost effective to manufacture in volume production.

Still further, it is often helpful if any artificial elements placed in a patient during a procedure such as the anastomosis of interest in this disclosure be absorbed after the healing process is complete. The anastomotic joint that has been disclosed in parent disclosures has a continuous malleable ring-shaped stent that will remain intact inside the body for the life of the patient while maintaining a predetermined opening. The inventors have observed that sometimes under high demand conditions, graft vessels will grow to make up for an increase in flow demand. While the anastomotic joint is usually created oversized to accommodate this demand it is difficult to predict the exact size that will be needed years ahead. Therefore, there is a need for an anastomosis system that uses elements that can be absorbed by the patient's body after the healing process is complete.

OBJECTS OF THE INVENTION

It is a main object of the present invention to provide an apparatus and method of performing an anastomosis without stopping the patient's heart.

It is also an object of the present invention to provide an anastomosis joint that is leak free and accurate.

It is another object of the present invention to provide an apparatus and method of performing an anastomosis without stopping the patient's heart in a minimally invasive manner.

It is another object of the present invention to provide an apparatus and method of performing an anastomosis without stopping the patient's heart in a minimally invasive manner in which the blood vessels are joined together in such a way as to most efficiently promote healing.

It is another object of the present invention to provide an apparatus and method of performing an anastomosis without stopping the patient's heart in a minimally invasive manner in which the blood vessels are joined together without squeezing, compressing or otherwise manhandling them.

It is another object of the present invention to provide a method and apparatus to stabilize a vessel while performing an anastomotic procedure.

It is another object of the present invention to provide an apparatus and method of performing an anastomosis without stopping the patient's heart in a minimally invasive manner in which the blood vessels are joined together to form a confluence area that accurately accounts for flow characteristics and flow parameters.

It is another object of the present invention to provide an apparatus and method of performing an anastomosis without stopping the patient's heart in a minimally invasive manner in which blood vessels can be joined together in a side-to-side configuration.

It is another object of the present invention to provide an apparatus and method of performing an anastomosis without stopping the patient's heart in a minimally invasive manner in which blood vessels can be joined together in an-end-to-side configuration.

It is another object of the present invention to provide an apparatus and method of performing an anastomosis without stopping the patient's heart in a minimally invasive manner in which blood vessels can be joined together to form a junction that is anatomically correct and accurately reflects blood vessel geometry at the junction.

It is another object of the present invention to reduce tissue inflammation and necrosis due to mishandling and over compression.

It is another object of the present invention to provide an anastomotic stapling device that provides blood flow to the heart while making the anastomosis.

It is another object of the present invention to provide an anastomotic apparatus and method which can join dissimilarly sized vessels.

It is another object of the present invention to provide an anastomotic apparatus and method which will accommodate joining vessel walls at a junction angle that varies with respect to a reference line.

It is another object of the present invention to provide an anastomotic apparatus and method which can effect a junction without a hemostatic medium.

It is another object of the present invention to provide an anastomotic apparatus and method which can be used in proximal junctions and in multiple anastomotic sites on the same vessel.

It is another object of the present invention to provide an anastomotic apparatus and a method for performing an anastomosis which will lend itself to efficient and cost-effective multiple by-pass techniques.

It is another object of the present invention to provide an anastomotic apparatus and method for performing an anastomosis which will lend itself to efficient and cost-effective jump graft techniques.

It is another object of the present invention to provide an anastomotic apparatus and method which is especially well suited for all types of blood vessel anastomosis procedures and techniques, such as, but not limited to, proximal, side-to-side, end-to-side, jump grafts as well as others that will occur to those skilled in the art based on the teaching of the present disclosure.

It is another object of the present invention to provide an anastomotic apparatus and method in which the two vessels involved in the procedure are properly and accurately aligned in an expeditious manner.

It is another object of the present invention to provide an anastomotic apparatus and method for ensuring the proper formation of fasteners used to attach anastomosis elements to vessels.

It is another object of the present invention to provide a hemostatic joint by the interdigitation of the tines.

It is another object of the present invention to provide an adjustable hemostatic joint.

It is another object of the present invention to provide a hemostatic joint that promotes tissue healing.

It is another object of the present invention to provide a hemostatic joint that does not crush tissue.

It is another object of the present invention to provide joining apparatus with an asymmetrical design of the tines.

It is another object of the present invention to provide a hemostatic joint with an atraumatic-sealing configuration.

It is another object of the present invention to provide a hemostatic joint by using the vessel as a compliant sealing media.

It is another object of the present invention to provide a hemostatic joint by varying the spacing of the tines based on the wall thickness at the vessel to provide optimum sealing compression.

It is another object of the present invention to provide a hemostatic joint having a ring-shaped stent for forming the joint in which the tines on the stent enter the outside wall of a vessel and turn the tissue of the vessel inward and up onto the stent.

It is another object of the present invention to provide a device that will deliver a hemostatic malleable ring-shaped stent to a vessel.

It is another object of the present invention to provide a device that will deliver a hemostatic malleable ring-shaped stent in a disposable cartridge.

It is another object of the present invention to provide a device that will provide proper guidance of the tines to enable proper formation of the tines on the tissue.

It is another object of the present invention to provide a device that will deploy a secondary anvil to crimp the tips of the tines; thereby locking on the tissue.

It is another object of the present invention to provide a device that will deploy a cutter to open the vessel wall within a ring to a predetermined size.

It is another object of the present invention to provide a ring-shaped stent that will change shape after installation on a vessel.

It is another object of the present invention to provide a device that is compact in size and allows the surgeon to position the tool with one hand.

It is another object of the present invention to provide a device that is ergonomic and allows adequate visualization to the surgical site.

It is another object of the present invention to provide a device for use with malleable ring-shaped stents used for tissue joinder that will approximate the malleable stents.

It is another object of the present invention to provide a device that will approximate the malleable stents and can be remotely activated.

It is another object of the present invention to provide a device that will join where joint compliance is provided by a docking leg.

It is another object of the present invention to provide a device that will join with joint compliance in the joining device.

It is another object of the present invention to provide a device that will approximate the malleable ring-shaped stents with a low profile end effector.

It is another object of the present invention to provide a device that will join the malleable stents.

It is another object of the present invention to provide a device that will permanently join the malleable stents and can be activated remotely.

It is another object of the present invention to provide an apparatus for joining the malleable stents that will deform one ring-shaped stent to fit on another.

It is another object of the present invention to provide an apparatus for joining the malleable stents with pre-tied suture loop.

It is another object of the present invention to provide an apparatus for joining the malleable stents with an elastomeric ring.

It is another object of the present invention to provide an apparatus for joining the malleable stents with a v-shaped spring clip.

It is another object of the present invention to provide an apparatus for joining the malleable stents with a c-shaped clip that will deform.

It is another object of the present invention to provide an apparatus for joining the malleable stents with a post and hole arrangement.

It is another object of the present invention to provide an apparatus for guiding the malleable stents together with a guide suture.

It is another object of the present invention to provide a method of manufacturing an anastomotic device with a chemical etch process.

It is another object of the present invention to provide a method of manufacturing an anastomotic device with chemical double etch process to produce areas of different thickness and edge properties.

It is another object of the present invention to provide a method of manufacturing an anastomotic device in a cost-efficient batch operation.

It is another object of the present invention to provide a method of manufacturing an anastomotic device in a cost-efficient batch operation with registration features for a secondary operation.

It is another object of the present invention to provide a method of manufacturing an anastomotic device with tines that have a sharp pointed tip with rounded edges.

It is another object of the present invention to provide an anastomotic apparatus and method in which the elements can be absorbed into the patient's body after the healing process is complete.

It is another object of the present invention to provide an anastomotic device with absorbable polymer sections.

It is another object of the present invention to provide an anastomotic device with expandable sections.

It is another object of the present invention to provide an absorbable polymer and stainless steel anastomotic device.

It is another object of the present invention to provide an absorbable polymer and titanium anastomotic device.

It is another object of the present invention to provide an anastomotic device that will change size based on the increased demand of blood flow to the heart.

SUMMARY OF THE INVENTION

These and other objects are achieved by the minimally invasive devices and methods disclosed in the parent applications which is further improved by including an apparatus and method for controlling the edges of the vessel wall to define an accurate and leak-free joint.

Specifically, the apparatus and method of the present invention designs and positions fasteners on malleable mounting structures so each fastener grabs the vessel and pulls the inside edge of the vessel adjacent to the incision upwardly in an evagination movement whereby the inside surfaces of the vessels of the anastomosis joint adjacent to the incisions in these vessels are in abutting contact when the fasteners are being formed on the vessels. Still further, the fasteners are positioned relative to each other so fasteners on one mounting structure associated with one of the vessels are interdigitated with adjacent fasteners on the mounting structure associated with the other vessel. The interdigitated orientation of fasteners creates a sinusoidal shape for the adjacent vessel edges. The sinusoidal shape of the abutting vessel edges creates a leak-free joint and does not require a hemostatic medium. The fasteners extend past the inside edge of the mounting structure when formed. This outward projection evaginates the tissue and the interdigitation of projecting fasteners causes the flexible vessel edge of one vessel to overlap the flexible vessel edge of the other vessel. The overlapping of tissue forms the leak-free joint. The interdigitation of fasteners on one structure with fasteners on the other structure forces tissue associated with the fasteners on the one structure to be deformed by the fasteners on the other structure. The deformation creates the sinusoidal-like shape at the joint. This sinusoidal-like shape has lobes that overlap each other; thereby forming the leak-free joint.

Still further, the fasteners, also referred to herein as tines, are sized, positioned and set to achieve this goal. The spacing between adjacent tines of the ring-shaped stents embodying the present invention is adjusted to achieve apparently counter-purpose goals. The tines are staggered between one side and the other creating an interdigitation of fasteners when the joint is formed. This allows compliance in the joint by opposing tissue-on-tissue and is referred to herein as a sinusoidal joint due to the sinusoidal shape of the abutting tissue. In addition, for a given vessel thickness there is a range of optimum spacing between the tissue retaining tines. Too many tines close together compress the tissue too much and lead to an increase of crush trauma. If the tines are too far apart, the joint will not seal properly.

In another embodiment the malleable stents can be attached in, a different way. The vessel docking legs would have malleable protrusions perpendicular to the body of the docking legs. The protrusions would be bent around the body of the docking leg on the artery side thereby affixing the stents together.

In yet another embodiment the malleable stents can be attached by folding or twisting or crimping the vessel docking leg over the artery docking leg thereby affixing the stents together.

In yet another embodiment the malleable stents can be attached by pushing the vessel docking leg, which has a hole in it, over a post attached to the artery docking leg. The post would have a one-way barb or a rib on it to prevent the stents from coming apart. Another way of preventing the docking legs from separating is to have tabs protruding from the hole on the vessel docking leg. This would create a one-way fit by binding against the post.

In yet another embodiment the malleable stents can be attached by running a spring-loaded clip down the guide suture and opening up over the docking legs thereby capturing the legs. The spring-loaded clip would have an integral cutter to sever the guide suture after it has been mounted.

In yet another embodiment the malleable stents can be attached by placing a suture loop over the mated docking legs. The suture loop would be cinched, tied and cut thereby affixing the stents together.

Still further, the apparatus and method of the present invention includes means and methods for accurately and efficiently aligning a mounting structure on one vessel with the mounting structure on the other vessel. The mounting structures of the present disclosure can be formed to include at least portions that are formed of absorbable material whereby at least a portion of the anastomosis joint will be absorbed by the patient's body after the healing process is complete.

Still further, the present invention includes a cost-effective process for producing a malleable ring-shaped stent which will achieve the goals set forth herein for the anastomosis procedure.

The process includes a chemical double etch process. In this process the planar pattern or pre-formed shape of the stent is duplicated on a sheet of material by a photo negative mask. The areas that have been covered by the photo negative mask will not be etched by the chemicals that the stent will be immersed into. Only the areas that have not been masked will be etched. The malleable stent would be held in place during the chemical bath through a series of carrier tabs. Once the sheet is removed from the chemical bath it would be re-masked with a photo negative around the malleable body of the stent except for the tines. The sheet would be re-immersed into the chemical bath for a set period of time to create a dual taper on the tines producing a sharp beveled point with rounded edges leaded to the point. Once the sheet is removed with a multitude of ring-shaped stents, it would be passed through a progressive die where the tines would be formed and removed from the carrier sheet into the final shape. Additionally the carrier sheet can be etched to create registration features which will provide exact alignment between the malleable ring-shaped stent and the tines still held in the carrier sheet for any secondary processes, such as die forming or over-molding.

The present invention can accommodate increased demand flow and correspondingly increase the confluence section of the joint by providing an oversized anastomosis. The device may alternately include a malleable ring-shaped stent made partially or entirely of a polymer material with tissue pins being metal. In some cases it is advantageous to make the stent from an absorbable material. There are a variety of reasons to make the stent at least partially absorbable, but the most basic begins with the surgeon's desire to have a device that can be used as an implant that will not require a second surgical intervention for removal or that changes properties in the body over time. In addition an anastomosis may expand demand for increased blood flow increases as the heart becomes healthier. Absorbable polymers are well known in the art, for example, there are about 125 million absorbable sutures sold each year in the United States, see for example "Synthetic Biodegradable Polymers as Medical Devices" by John C. Middleton and Arthur J. Tipton appearing in the March/April 1998 issue of "Medical Plastics and Biomaterials" at pages 30–39, the disclosure of which is incorporated herein by reference. Absorbable sutures allow the surgeon to mechanically fasten tissue, while over a short amount of time the tissue will remodel while the suture is absorbed into the body. The partially absorbable malleable stent of the present invention uses absorbable sections as a mechanical means to join tissue; while over time these sections will degrade thus freeing segments of the malleable stent to grow as needed. One form of the stent of the present invention has malleable sections and absorbable sections. In this stent the non-absorbable malleable sections have interrupted sections that are imbedded in the polymer. Since absorbable materials are formulated to break down and become absorbed in the body at different times, the chemistry of the polymer can be designed to break down after the vessel walls have had sufficient time to heal and create a structural bond. After that time, the integrity of the polymer stent will break down; therefore, the non-absorbable sections are free to move away from each other allowing the anastomosis to grow if necessary. The number and positions of the malleable sections and breakaway absorbable sections are determined by the overall size of the stent and the expected need to allow the anastomosis to expand.

BRIEF DESCRIPTION OF THE DRAWING FIGURES

FIG. 4 is a side view of a cuff which is included in the apparatus for performing an anastomosis.

FIG. 5 is a sectional view of the cuff when taken along line 5—5 of FIG. 4A.

Figure 25:
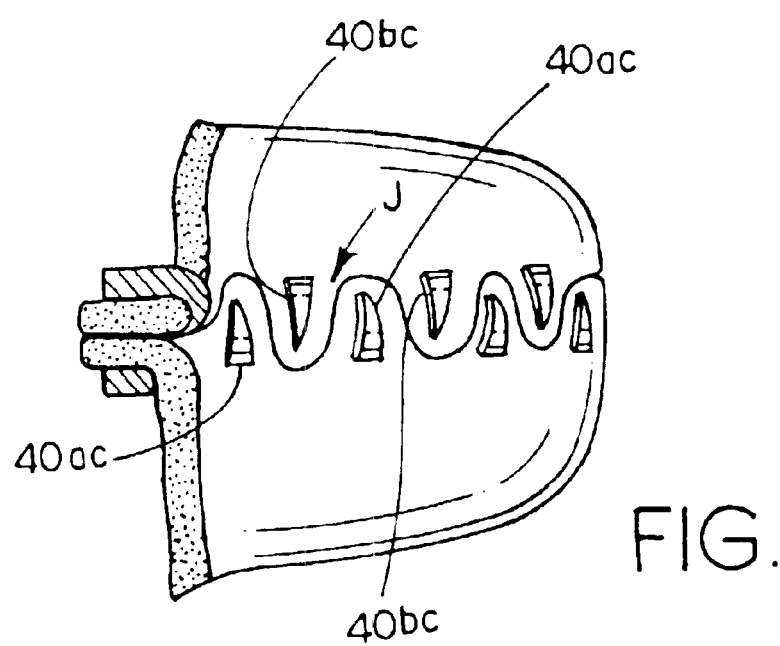

FIG. 25 also shows the sinusoidal-like shape of the joint formed between the two vessels.

Figure 26:
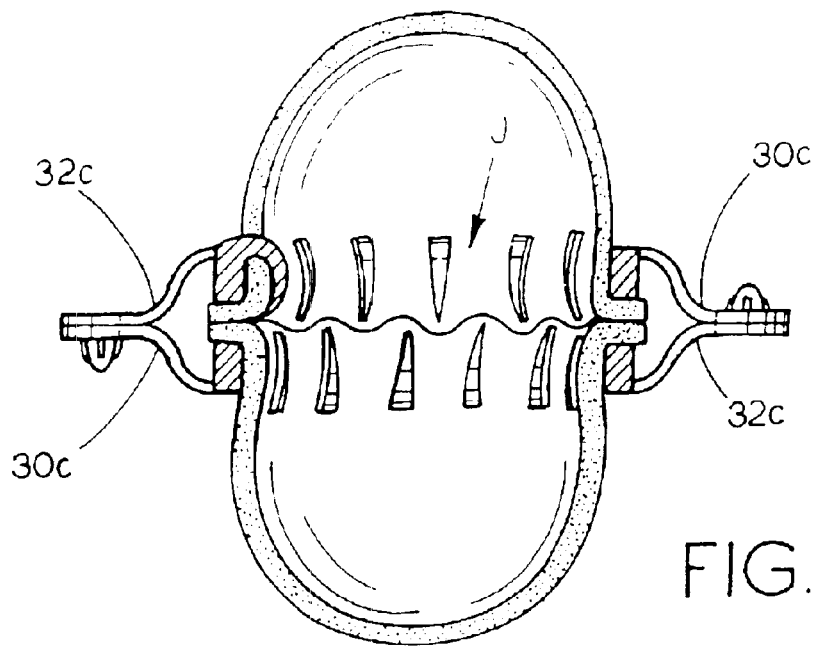

FIG. 26 shows a cross section of a finished anastomosis.

Figure 27:
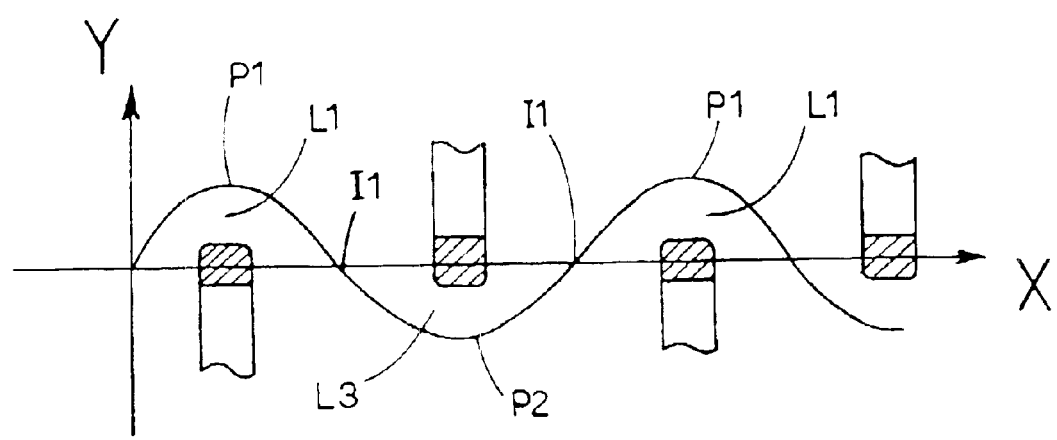

FIG. 27 is a sine curve used to define the terms used in this disclosure.

Figure 27A:
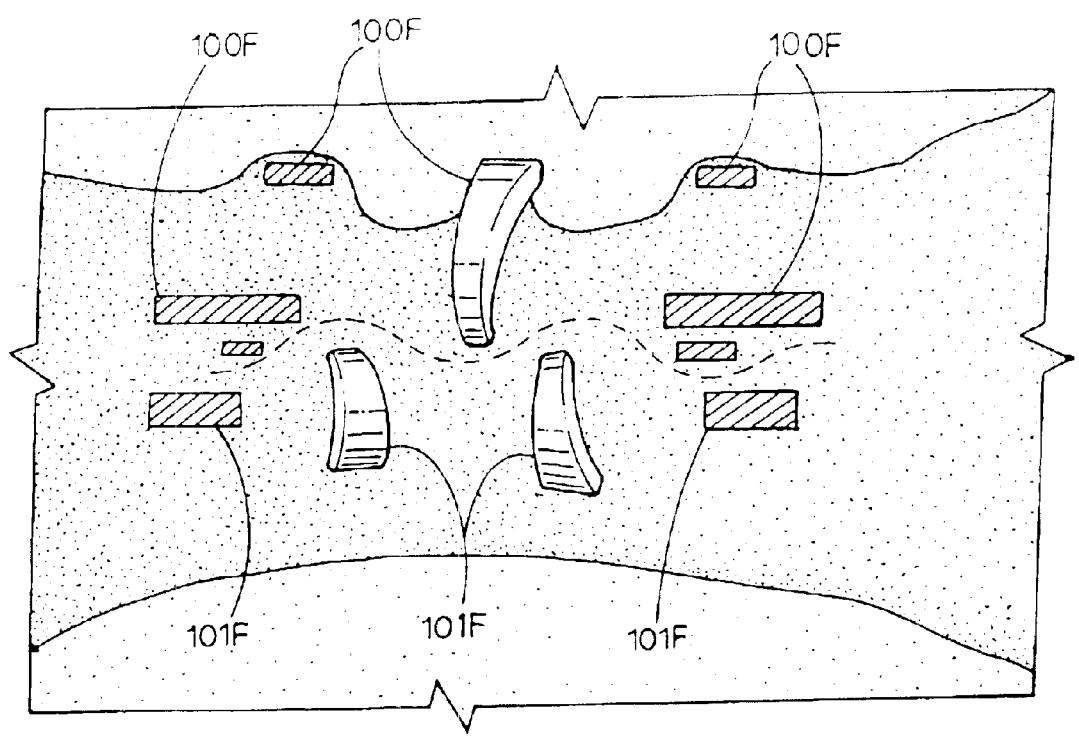

FIG. 27A shows a histology cross section.

Figure 27B:
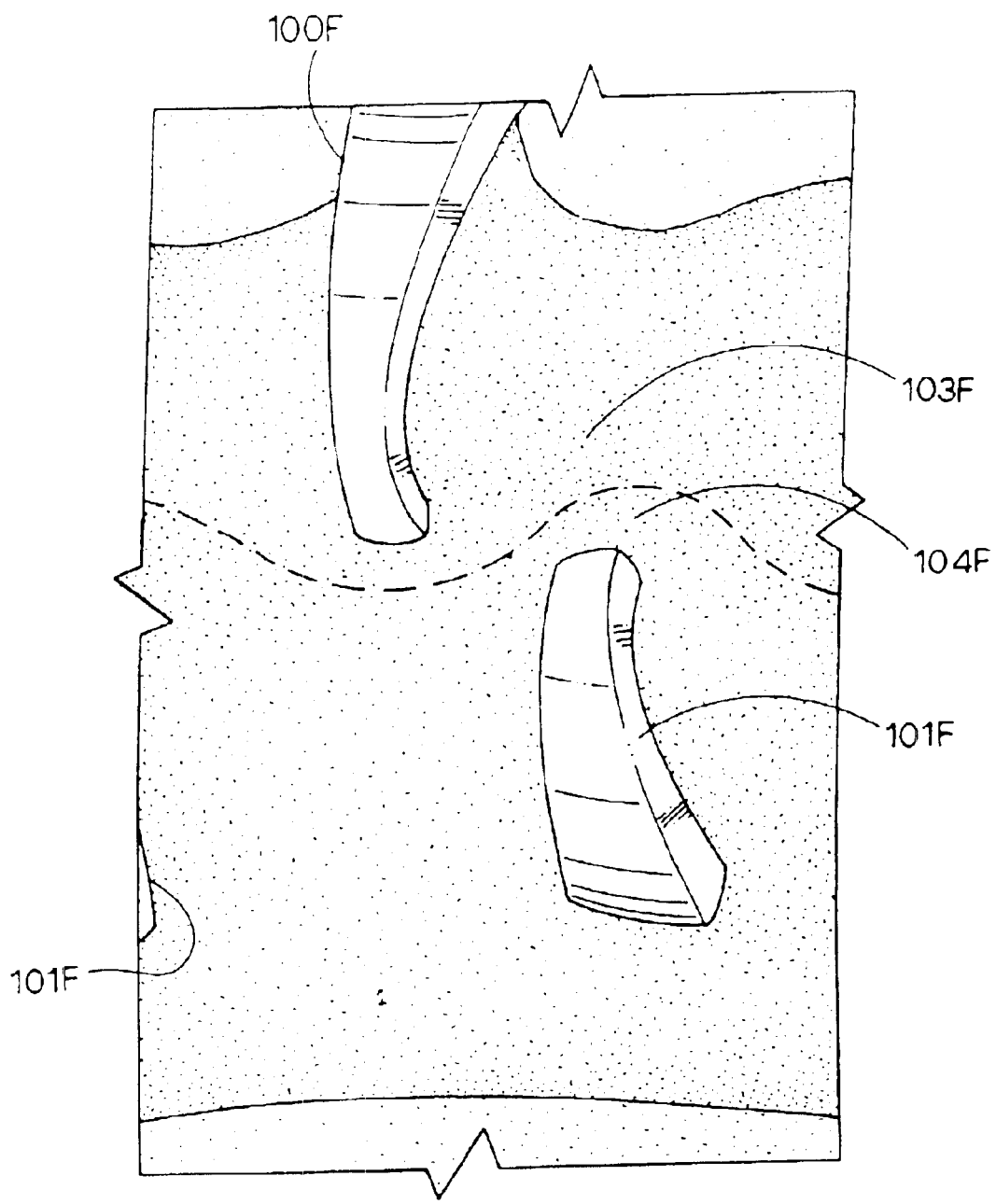

FIG. 27B is a magnified view from the central area of FIG. 27A.

Figure 28:
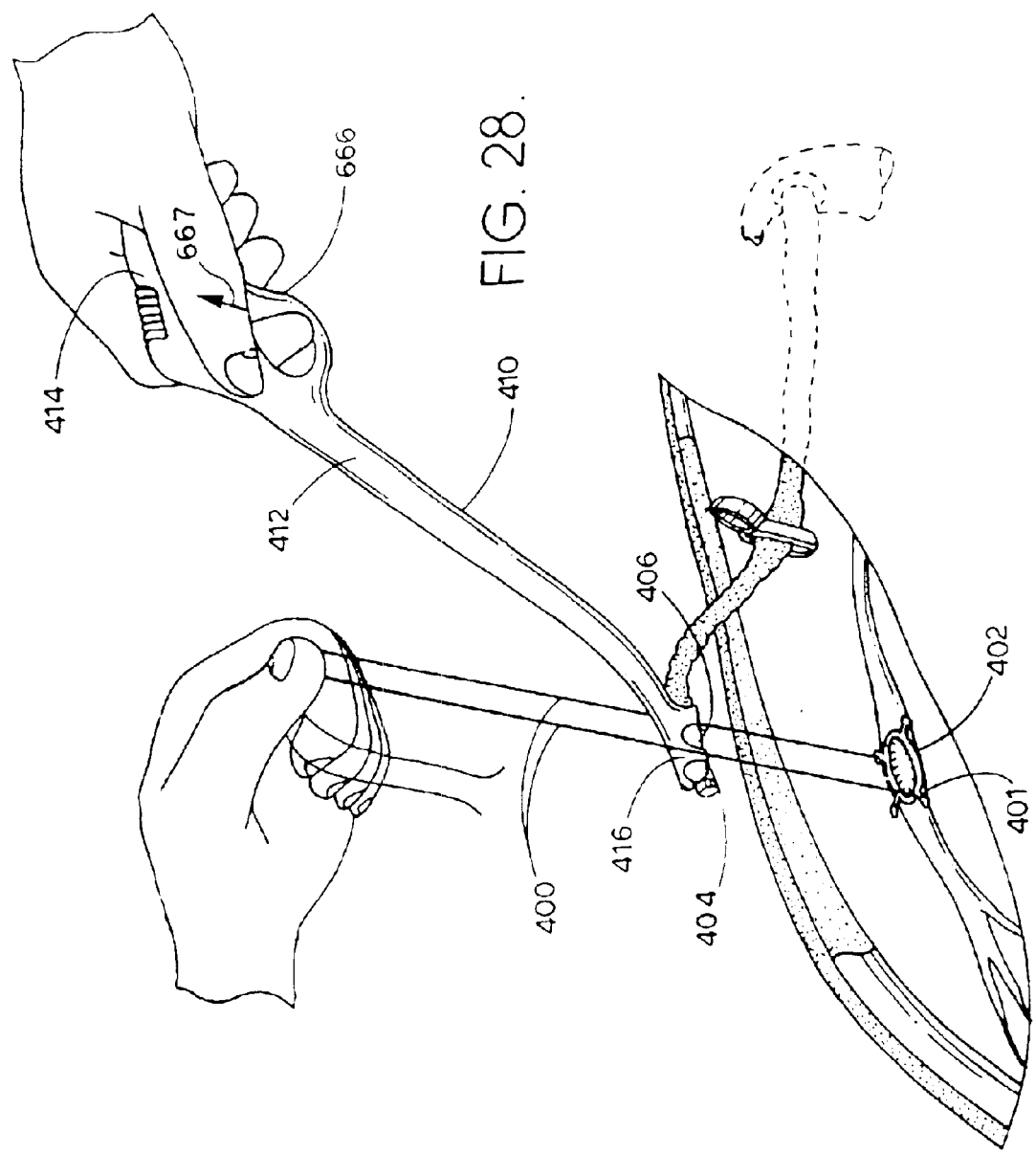

FIG. 28 illustrates guiding a graft vessel into place on an artery.

Figure 29A:
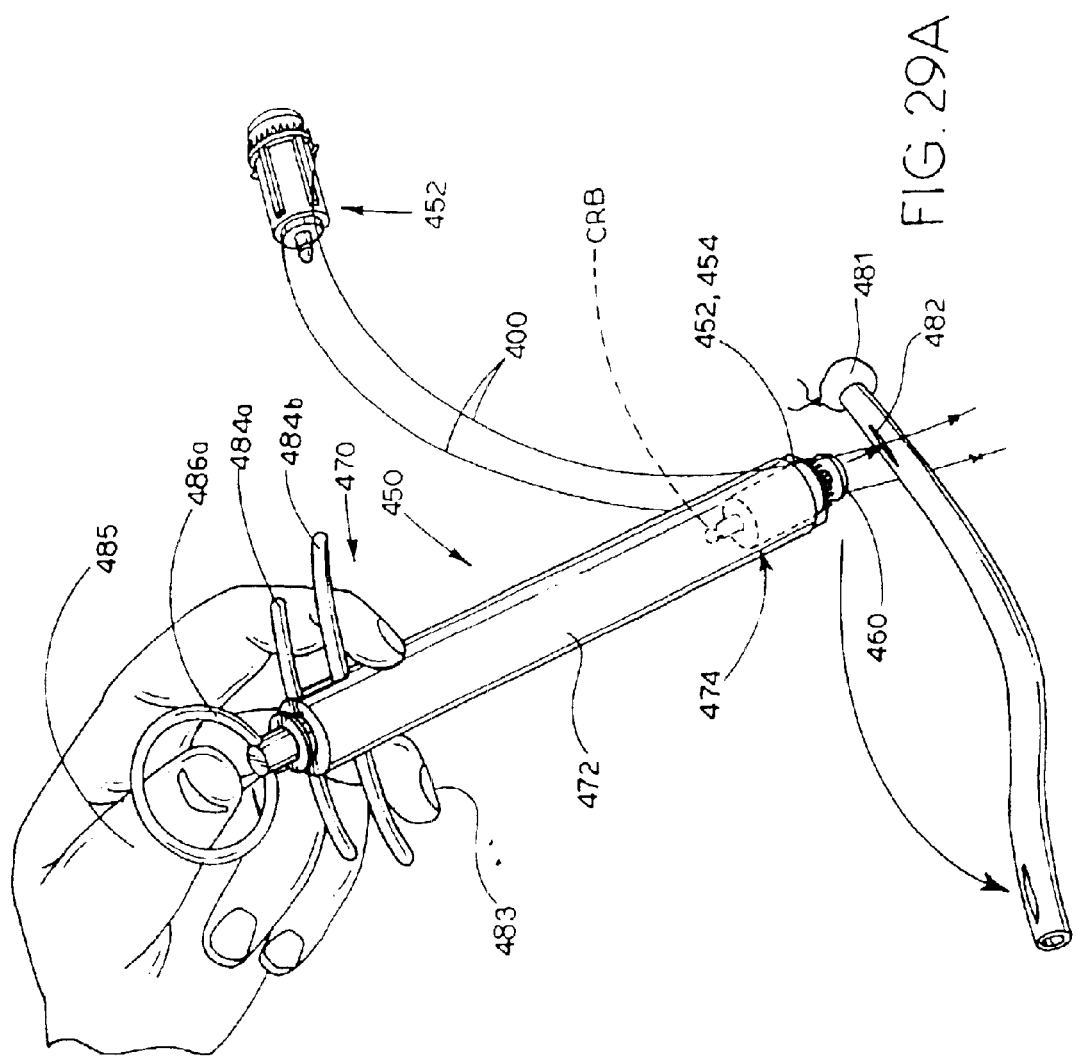

FIG. 29A illustrates placement of the malleable support structure ring-shaped stent on a graft vessel through use of a compact firing tool having a disposable cassette which holds the stent.

FIG. 29B is a longitudinal sectioned view through the compact firing tool of FIG. 29A, showing the disposable cassette spaced from and about to be inserted into the tool.

FIG. 29C is a longitudinal sectioned view of the compact firing tool of FIG. 29A, with parts thereof broken away, showing the disposable cassette inserted into the tool.

FIG. 29D is an exploded perspective view of the compact firing tool and cassette of FIG. 29A, with parts thereof broken away.

FIG. 30 is a longitudinal sectioned view of the cassette used in the compact firing tool of FIG. 29A.

Figure 31:
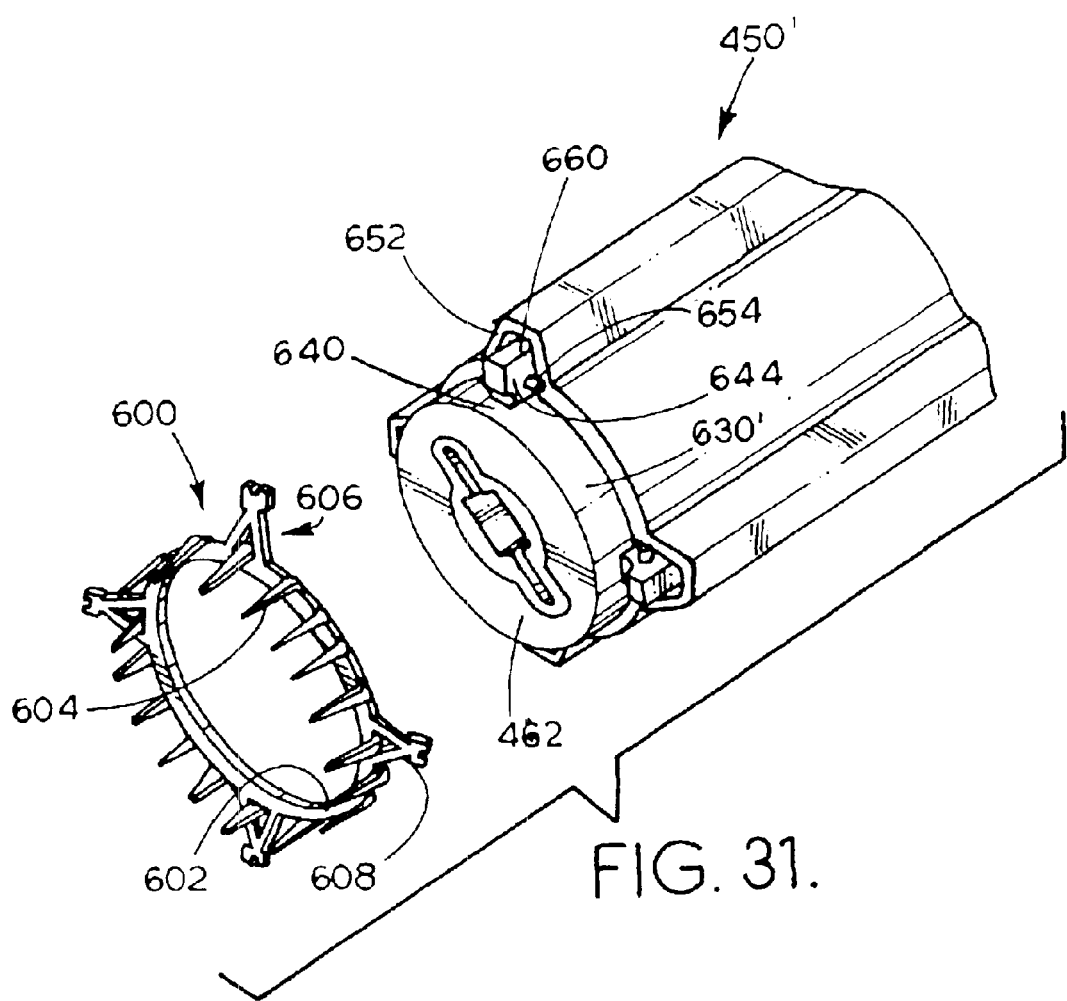

FIG. 31 is an exploded perspective view with parts thereof broken away, of a compact firing tool for placing the malleable ring-shaped stent on a vessel, wherein the stent is supported directly on tool without the use of a disposable cassette.

Figure 32A:
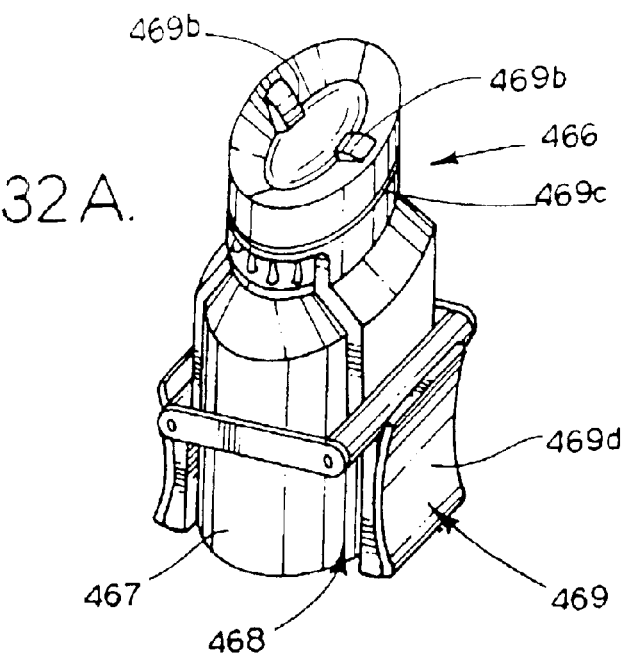

FIG. 32A is a perspective view of a loading cartridge which may be used to load a malleable ring-shaped stent directly on the tool of FIG. 31.

Figure 32B:
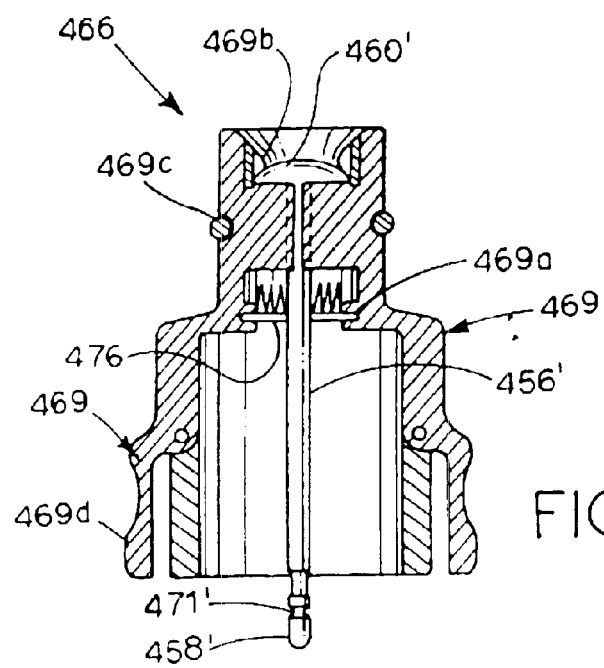

FIG. 32B is a longitudinal sectioned view of the cartridge of FIG. 32A.

FIG. 33A is a longitudinal sectioned view, with parts thereof broken away, of the compact firing tool of FIG. 31 with the cartridge of FIGS. 32A and 32B about to be used to load a malleable ring-shaped stent onto the tool.

FIG. 33B is a longitudinal sectional view, with parts thereof broken away, of the compact firing tool of FIG. 31 with the cartridge of FIGS. 32A and 32B engaged thereon to load a malleable stent onto the tool.

FIG. 33C is a longitudinal sectioned view, with parts thereof broken away, of the compact firing tool of FIG. 31 with the cartridge of FIGS. 32A and 32B released from the tool for removal.

FIG. 34A shows a portion of a tool used to set and manipulate a mounting structure on a vessel.

Figure 34B:
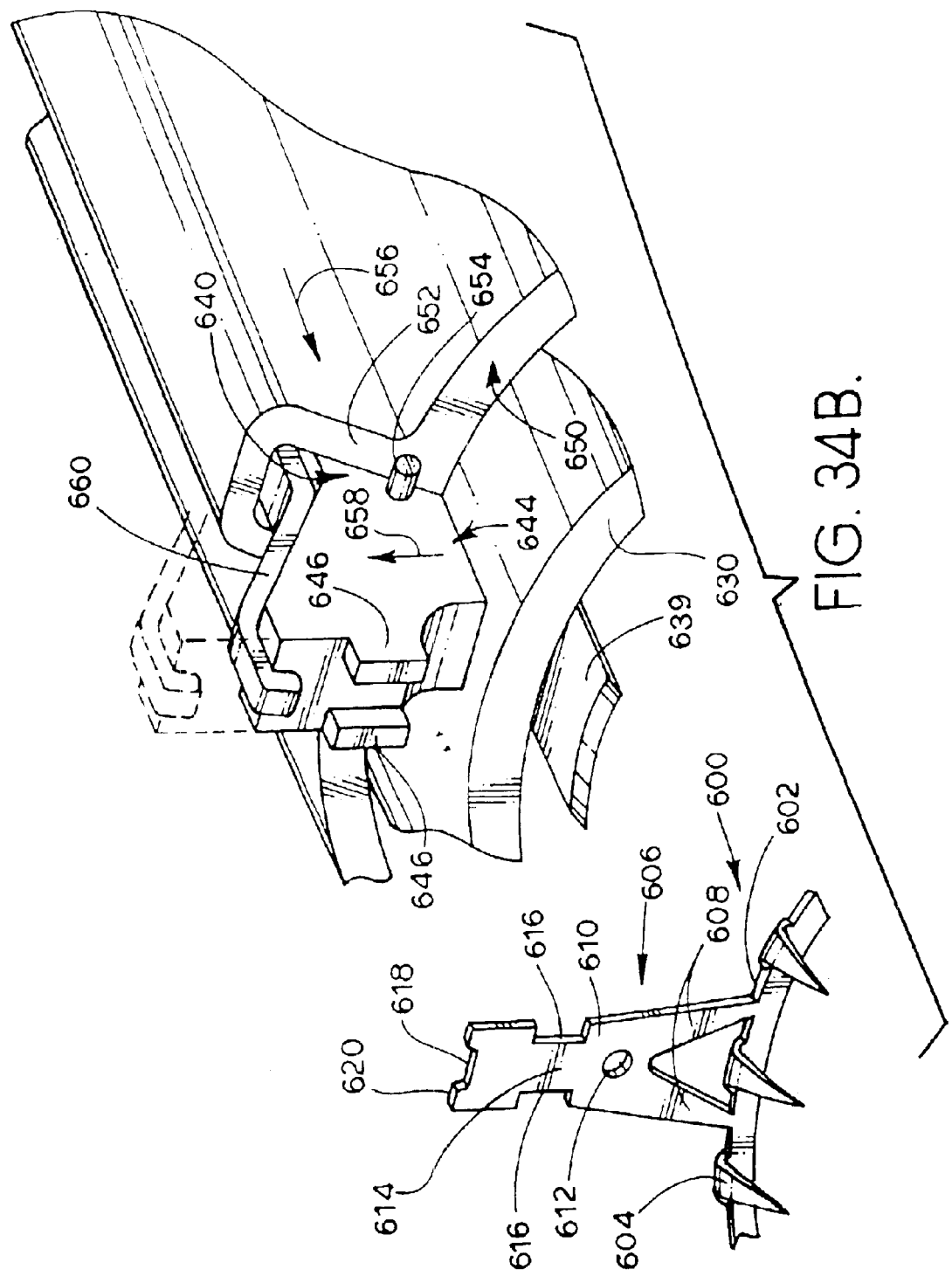

FIG. 34B is an enlarged view of the distal end of the tool shown in FIG. 34.

FIG. 35A illustrates a ring-shaped stent engaged with guide sutures.

FIG. 35B illustrates guiding one mounting structure to the other mounting structure according to the teaching of this invention.

Figure 35C:
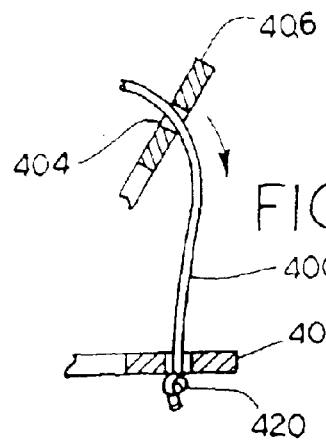

FIG. 35C shows portions of the two mounting structures of FIG. 35B before they are guided into contact with each other.

Figure 35D:
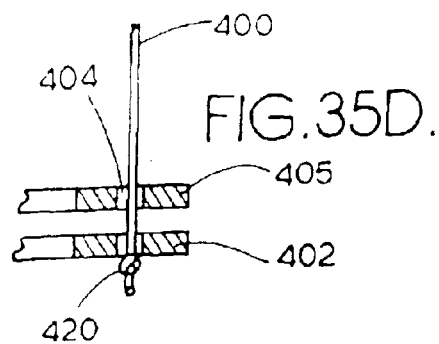

FIG. 35D shows portions of the two mounting structures of FIG. 35B just before they are guided into contact with each other.

Figure 35E:
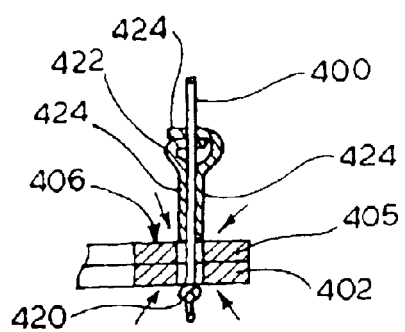

FIG. 35E shows portions of the two mounting structures of FIG. 35B just after they are guided into contact with each other.

Figure 35F:
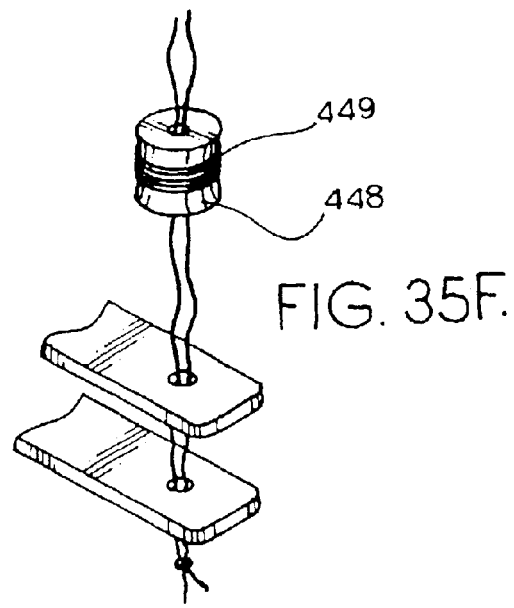

FIG. 35F shows an alternative form of a means for holding the two mounting structures of FIG. 35B together.

Figure 36A:
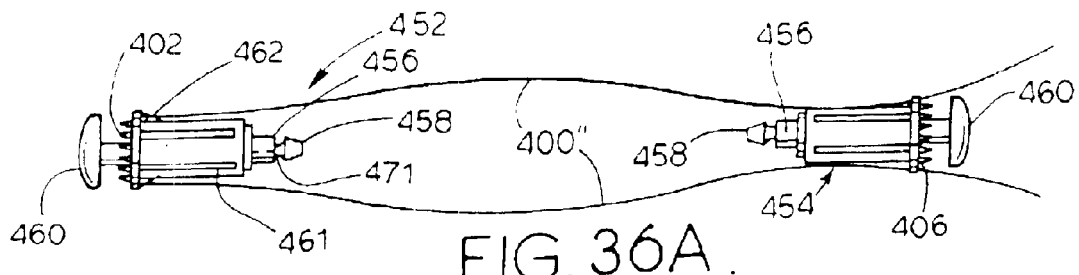

FIG. 36A shows cassettes used to store and set mounting structures on a graft vessel.

Figure 36B:
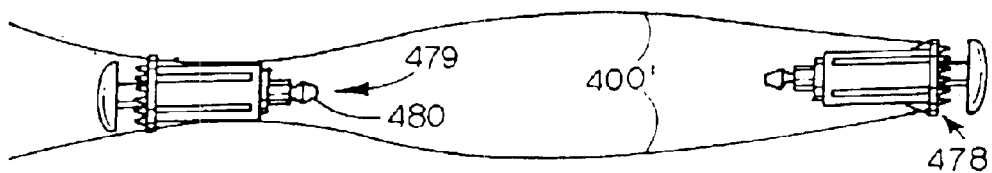

FIG. 36B shows cassettes used to store and set mounting structures on an aorta vessel.

Figure 37A:
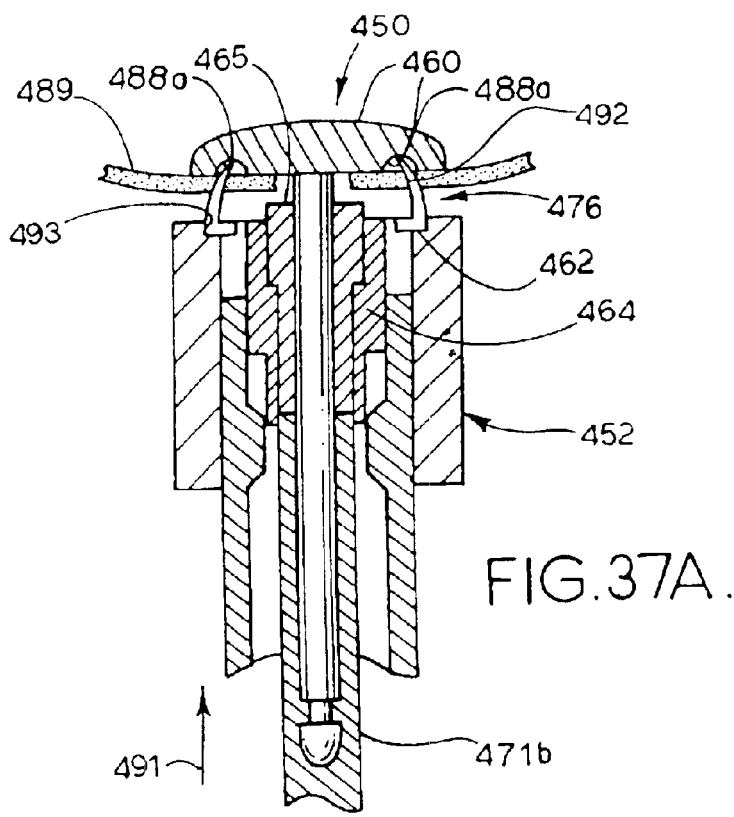
Figure 37C:
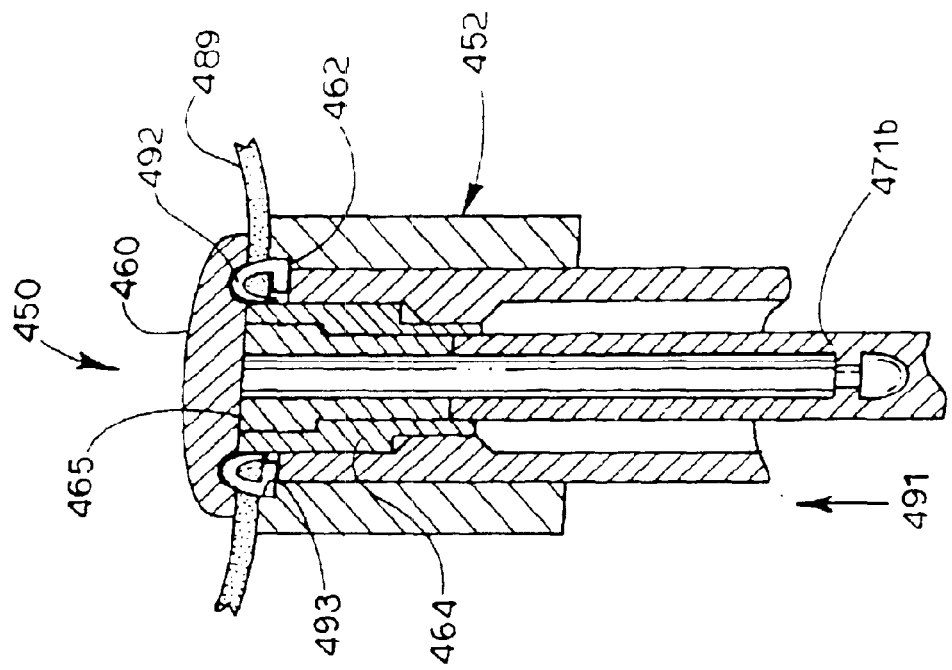
Figure 37B:
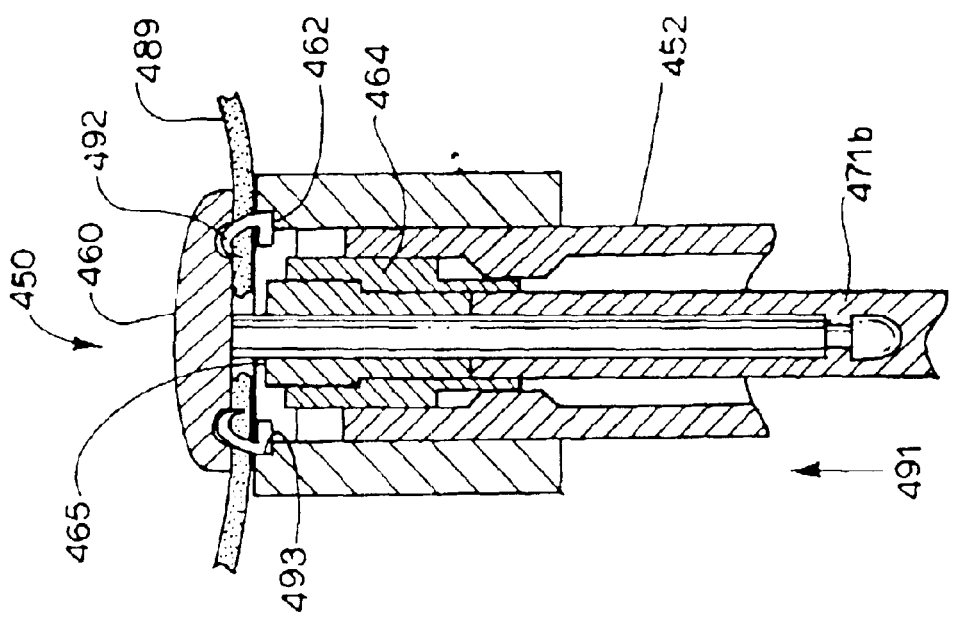

FIGS. 37A–37C show cross sectional views through the tip of a disposable cartridge as the malleable ring-shaped stent is placed.

Figure 38C:
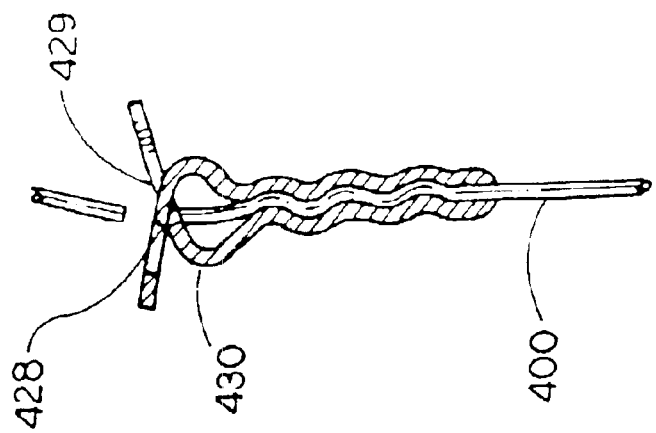
Figure 38B:
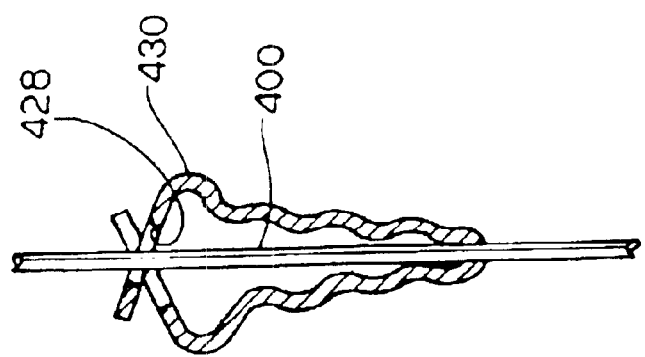
Figure 38A:
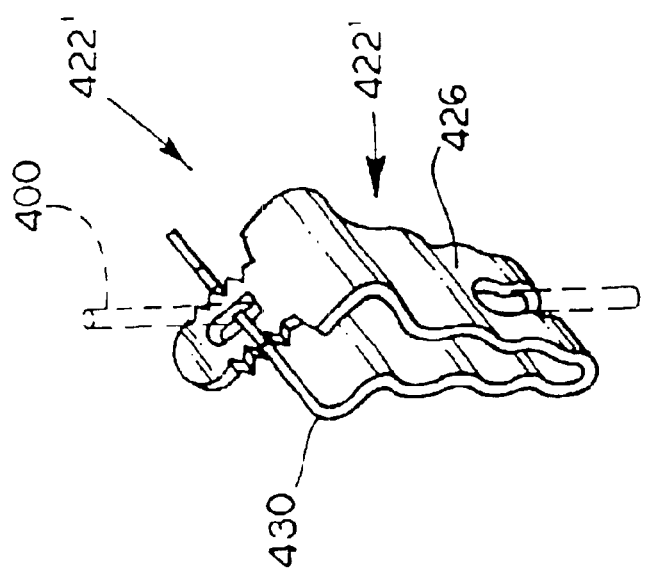

FIG. 38A shows a clamp for attaching one mounting structure to the other.

FIG. 38B shows an elevational view of the clamp shown in FIG. 38A.

FIG. 38C shows the clamp shown in FIG. 38A in a closed condition.

Figure 39:
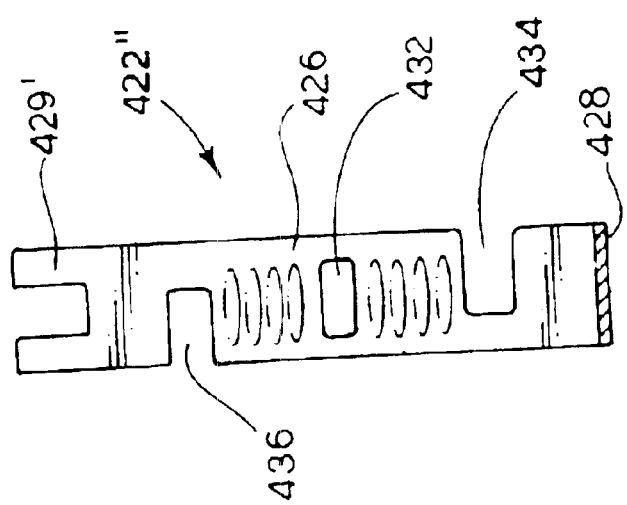

FIG. 39 shows another form of a clamp used to attach one mounting structure to another.

Figure 40:
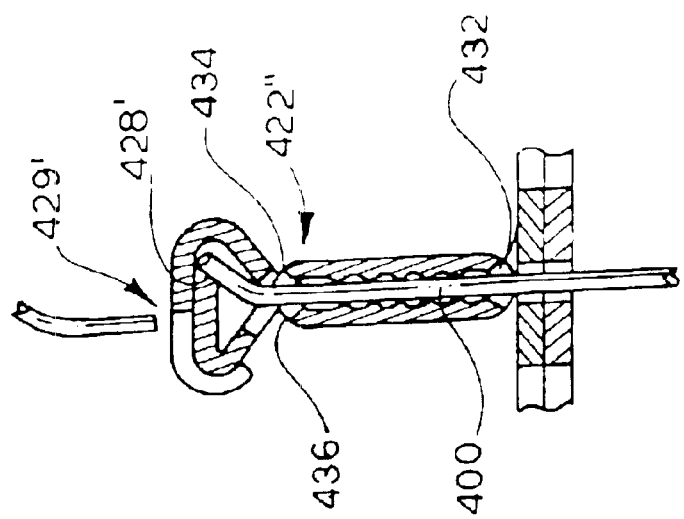

FIG. 40 shows the clamp shown in FIG. 39 in position on the mounting structures.

Figure 41:
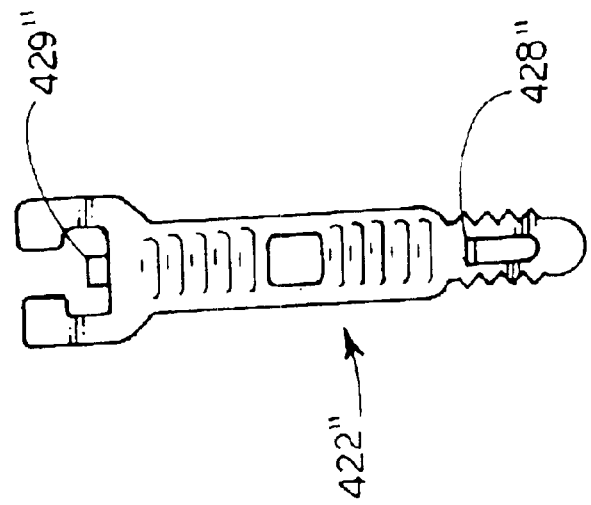

FIG. 41 shows another form of the clamp used to attach one mounting structure to the other.

FIG. 42A shows another form of the clamp used to attach one mounting structure to the other.

FIG. 42B is an elevational view of the clamp shown in FIG. 42A.

FIG. 43A shows another form of clamp for holding two mounting structures together.

FIG. 43B shows another form of clamp for holding two mounting structures together.

Figure 43C:
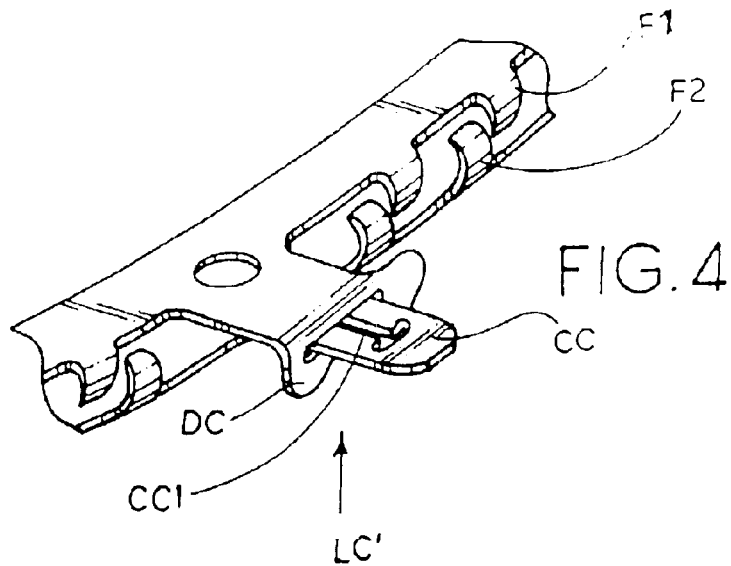

FIG. 43C shows another form of clamp for holding two mounting structures together.

Figure 43D:
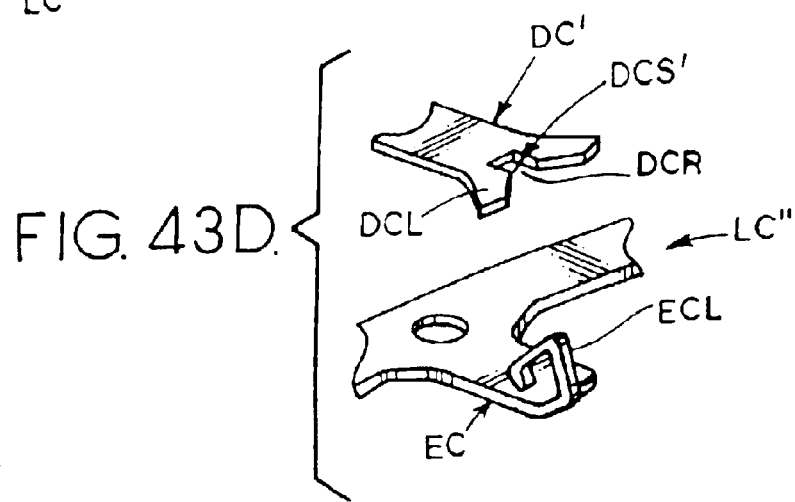

FIG. 43D shows another form of clamp for holding two mounting structures together.

Figure 43E:
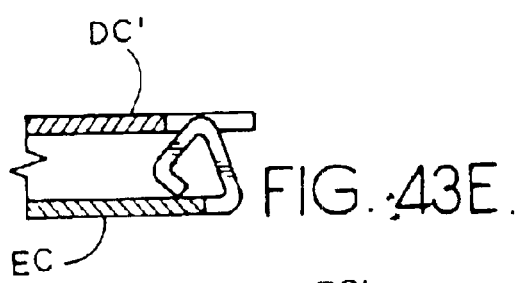

FIG. 43E shows a portion of the FIG. 43D clamp just prior to engagement.

Figure 43F:
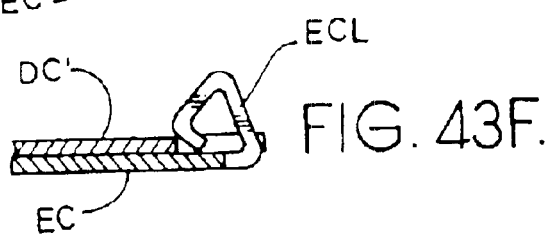

FIG. 43F shows a portion of the FIG. 43B clamp after engagement.

Figure 43G:
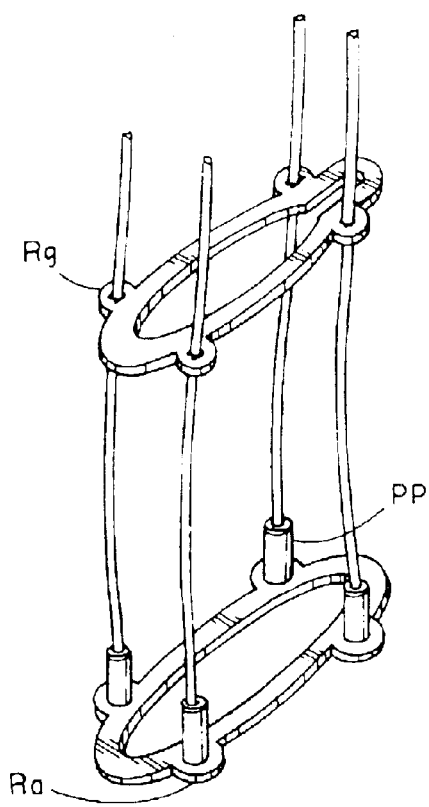
Figure 43H:
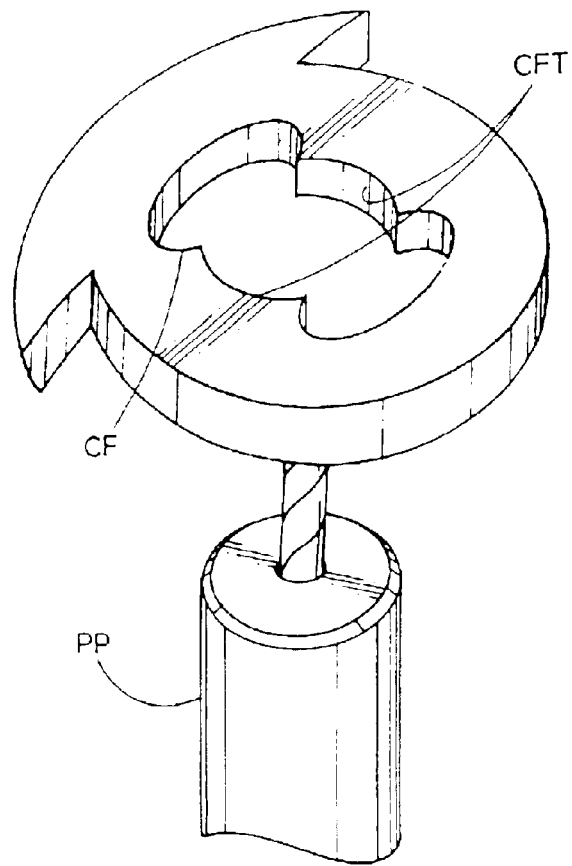

FIGS. 43G and 43H show another form of clamp for holding two mounting structures together.

Figure 43I:
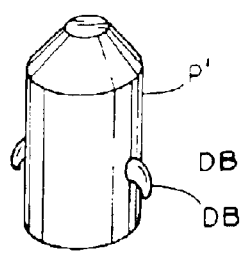

FIG. 43I shows another form of clamp for holding two mounting structures together.

Figure 43J:
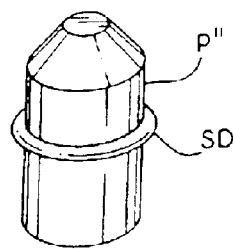

FIG. 43J shows another form of clamp for holding two mounting structures together.

Figure 43K:
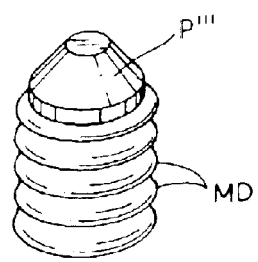

FIG. 43K shows another form of clamp for holding two mounting structures together.

Figure 43L:
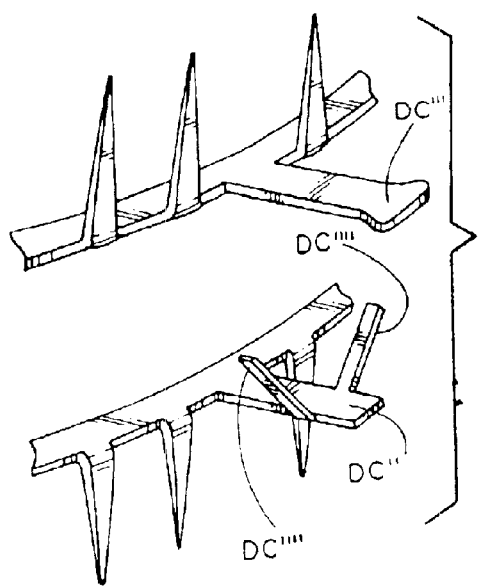
Figure 43M:
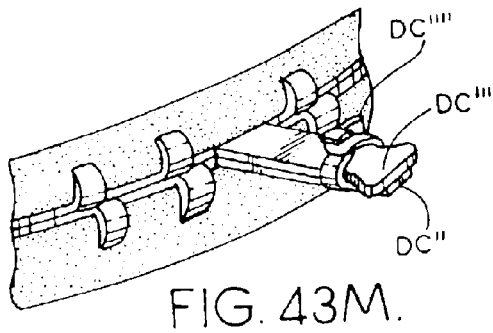

FIGS. 43L and 43M illustrate a twist clamp for holding to mounting structures together, with FIG. 43K showing the clamp open and FIG. 43L showing the clamp closed.

FIG. 44 shows a malleable ring-shaped stent attached to a graft vessel.

FIG. 45 shows a bottom view of the distal end of a docking guide tool.

FIG. 46 illustrates a flexible docking tool.

FIG. 47 illustrates the docking tool of FIG. 46 applying an O-ring to an in-place joint.

Figure 48:
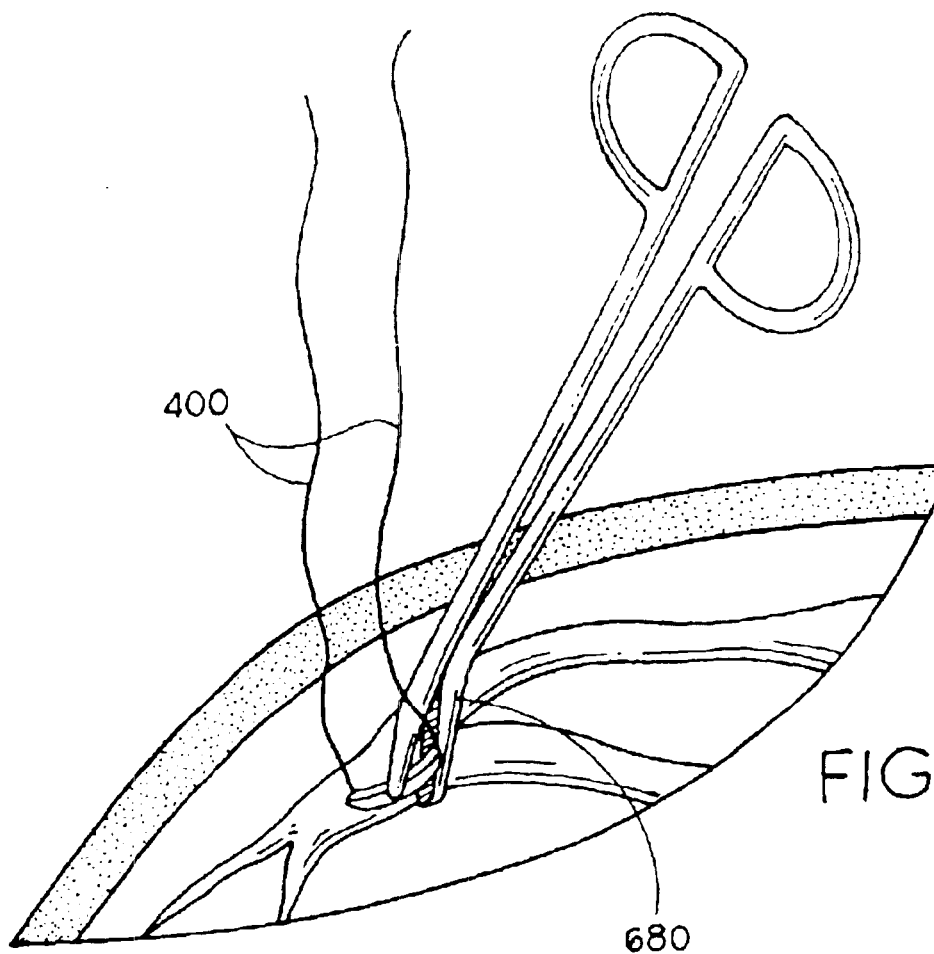

FIG. 48 illustrates cutting of guide sutures after the joint is in place.

Figure 49:
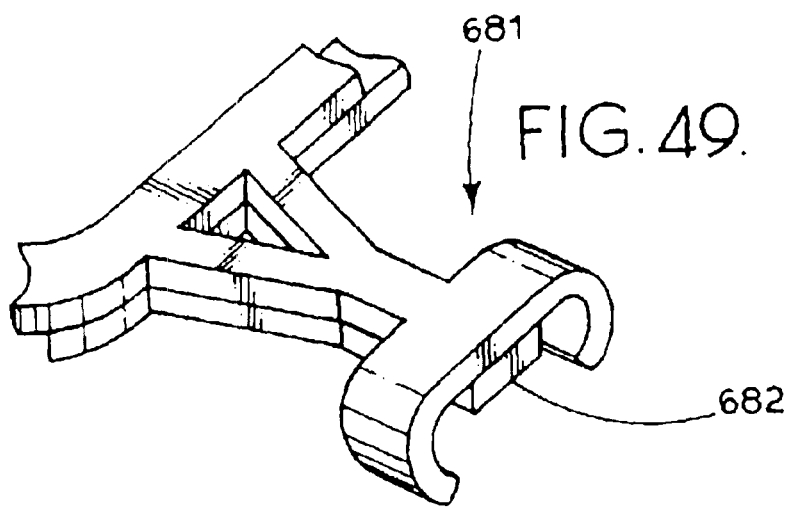

FIG. 49 illustrates a way of attaching two ring-shaped stents together.

FIGS. 50A–50C illustrate the attaching process for the stent shown in FIG. 49.

FIG. 51 shows a fastener element having a multiplanar shape so it will form into the desired shape during the anastomosis procedure of the present invention.

Figure 52:
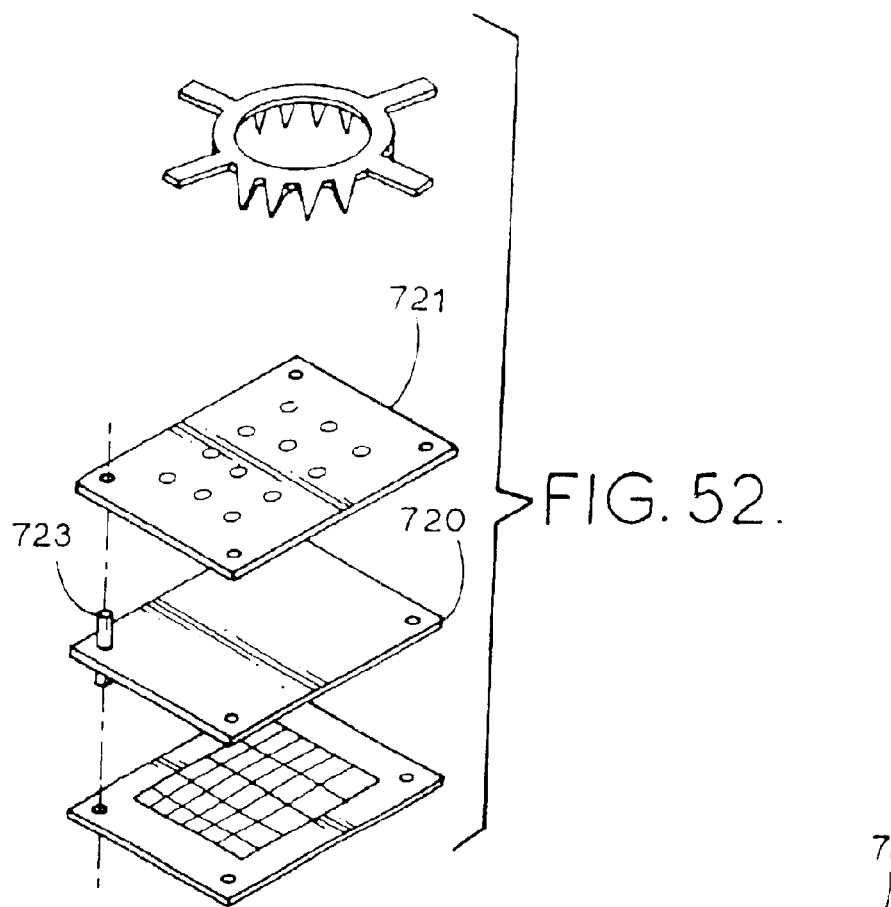

FIG. 52 is an exploded perspective view illustrating the elements associated with the process for forming the malleable ring-shaped stent of the present invention.

Figure 53:
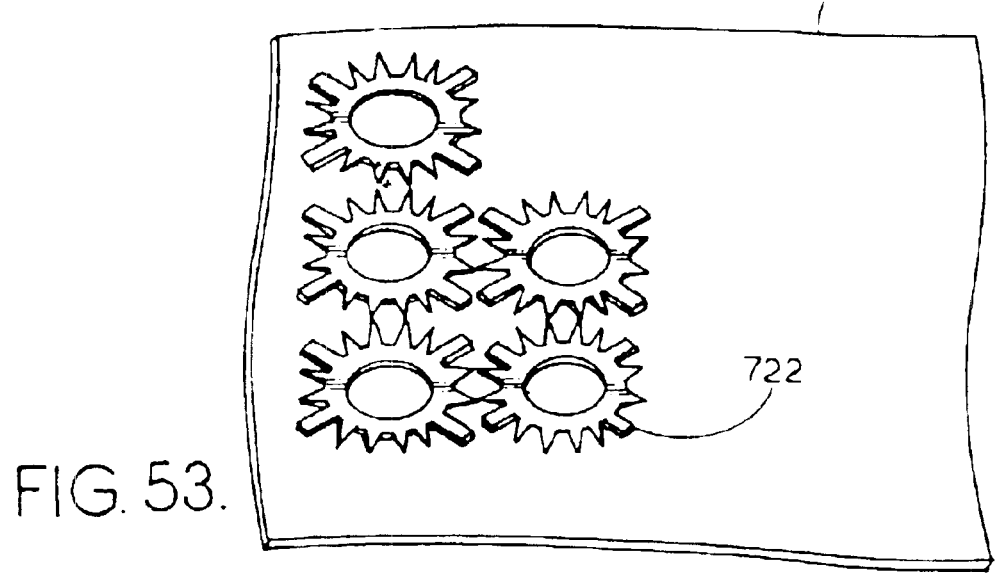

FIG. 53 illustrates the resist image used to produce a plurality of malleable stents.

FIG. 54 shows a chisel point formed in a single pass chemical etch process.

FIG. 55A illustrates a point configuration formed by the process of the present invention.

FIG. 55B shows an end elevational view of a tine formed by the process of the present invention.

FIG. 56 shows the body of a malleable ring-shaped stent formed by the process of the present invention being re-masked on both sides of etched stents.

Figure 57:
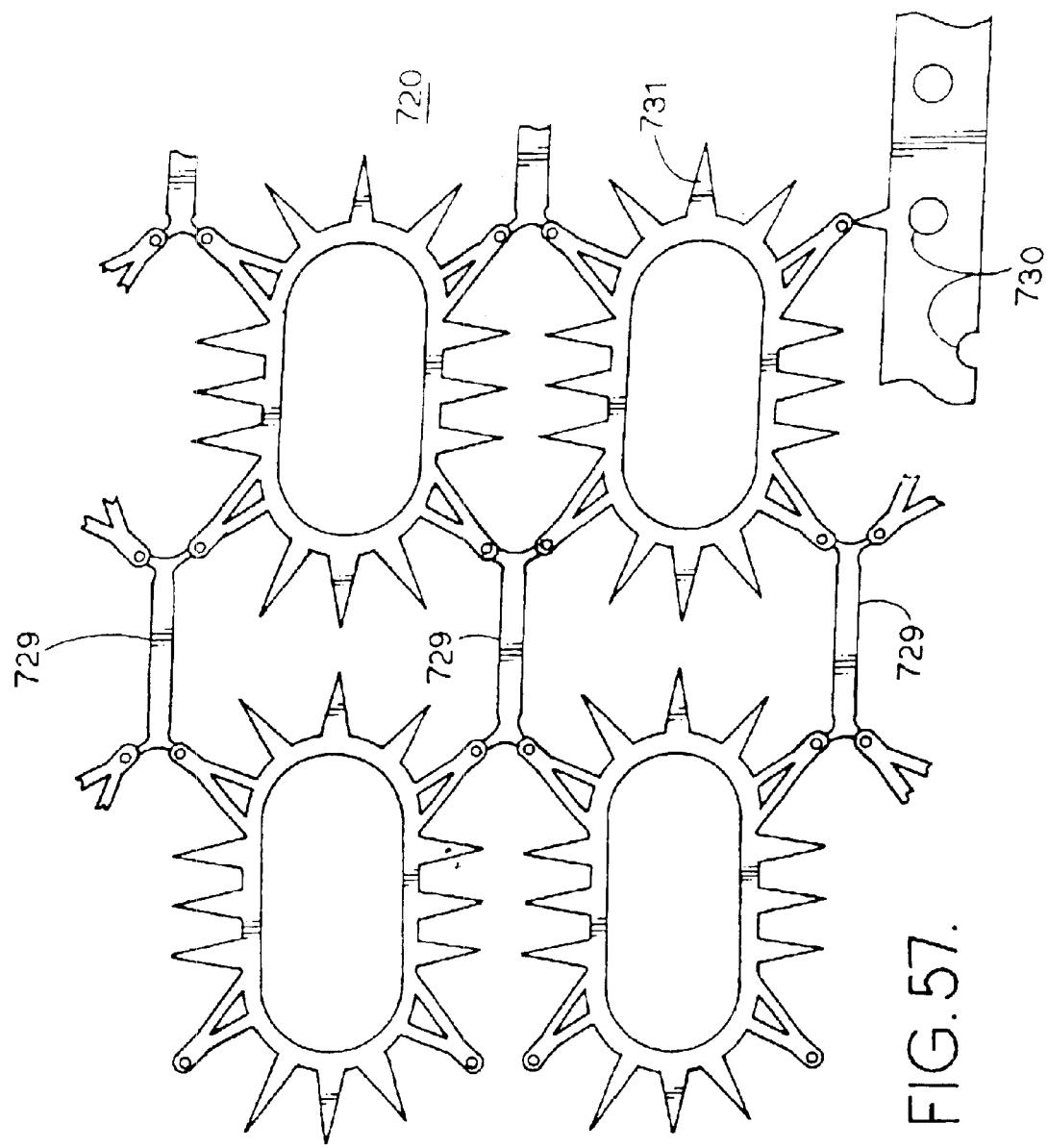

FIG. 57 is a partial view of a finished sheet of malleable stents formed according to the process of the present invention.

Figure 58A:
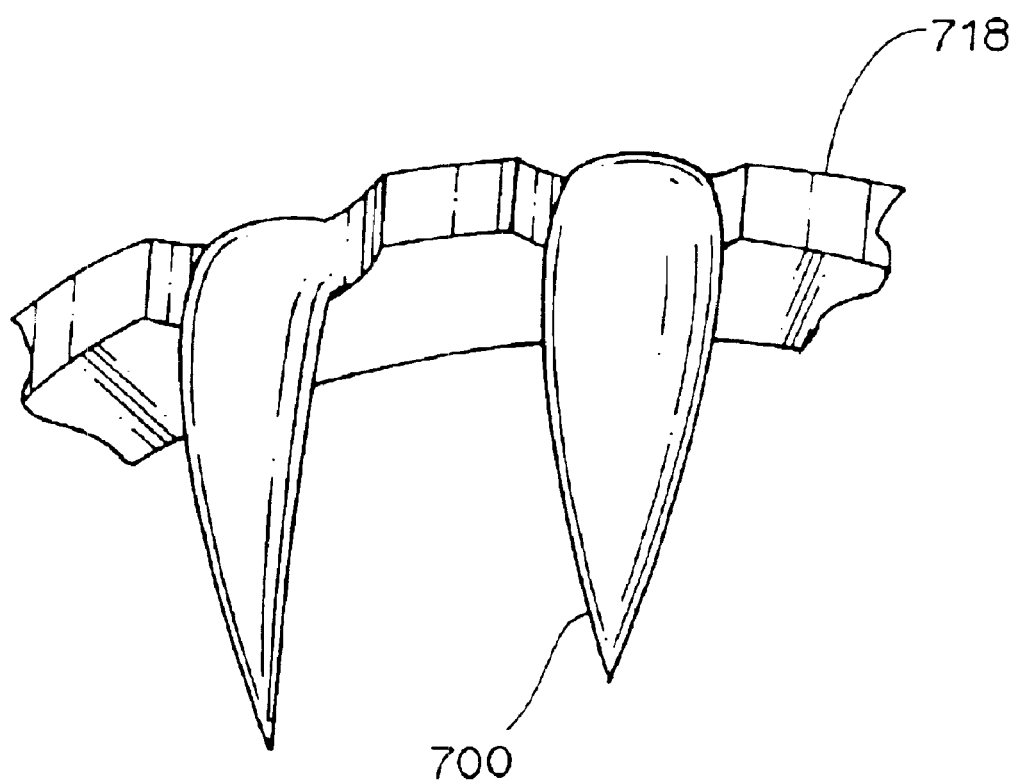

FIG. 58A shows a portion of a malleable ring-shaped stent of the present invention.

Figure 58B:
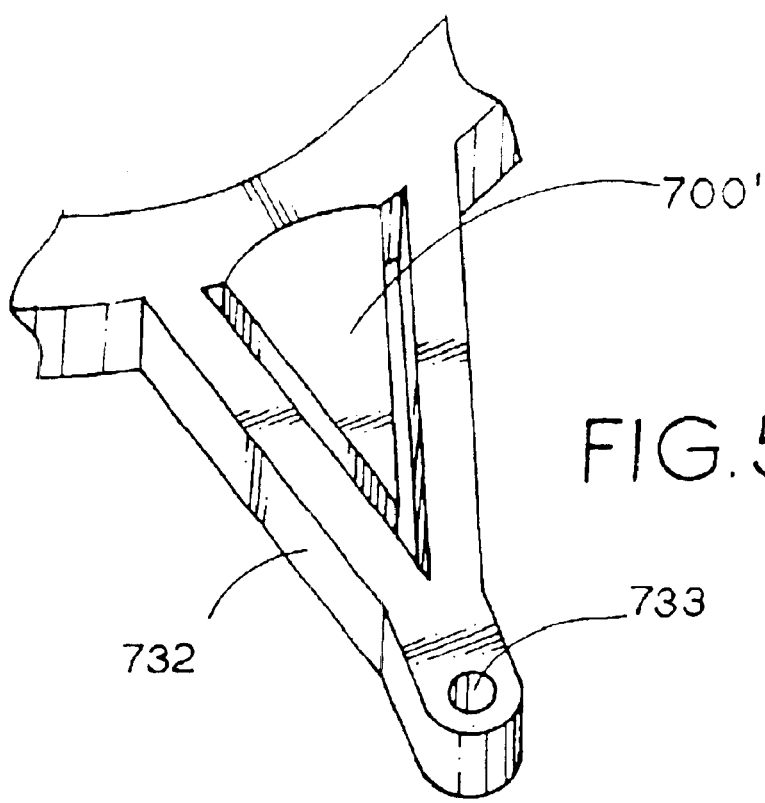

FIG. 58B shows a tine coincident with a connection tab.

Figure 58C:
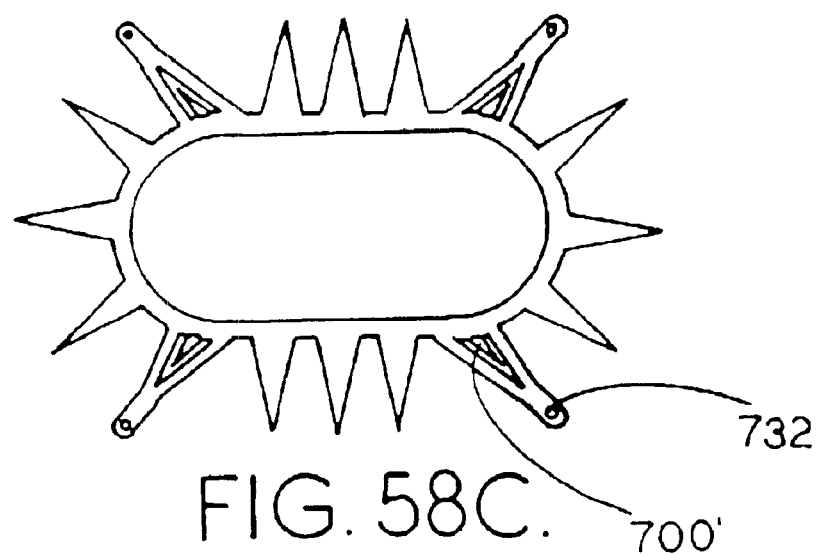

FIG. 58C shows a malleable ring-shaped stent with at least one tine coincident with a connection tab that is used to connect the stent with another stent.

Figure 59A:
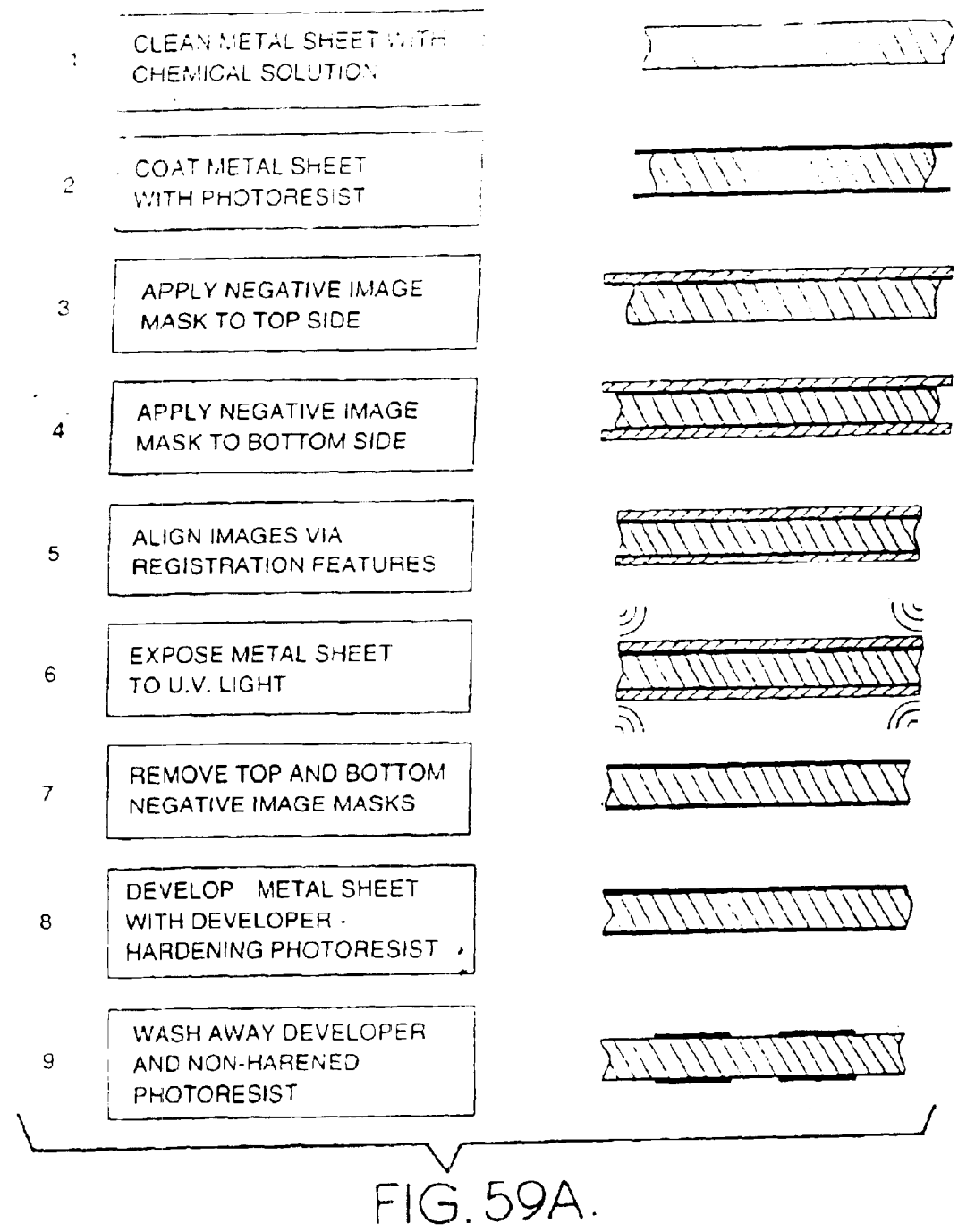
Figure 59B:
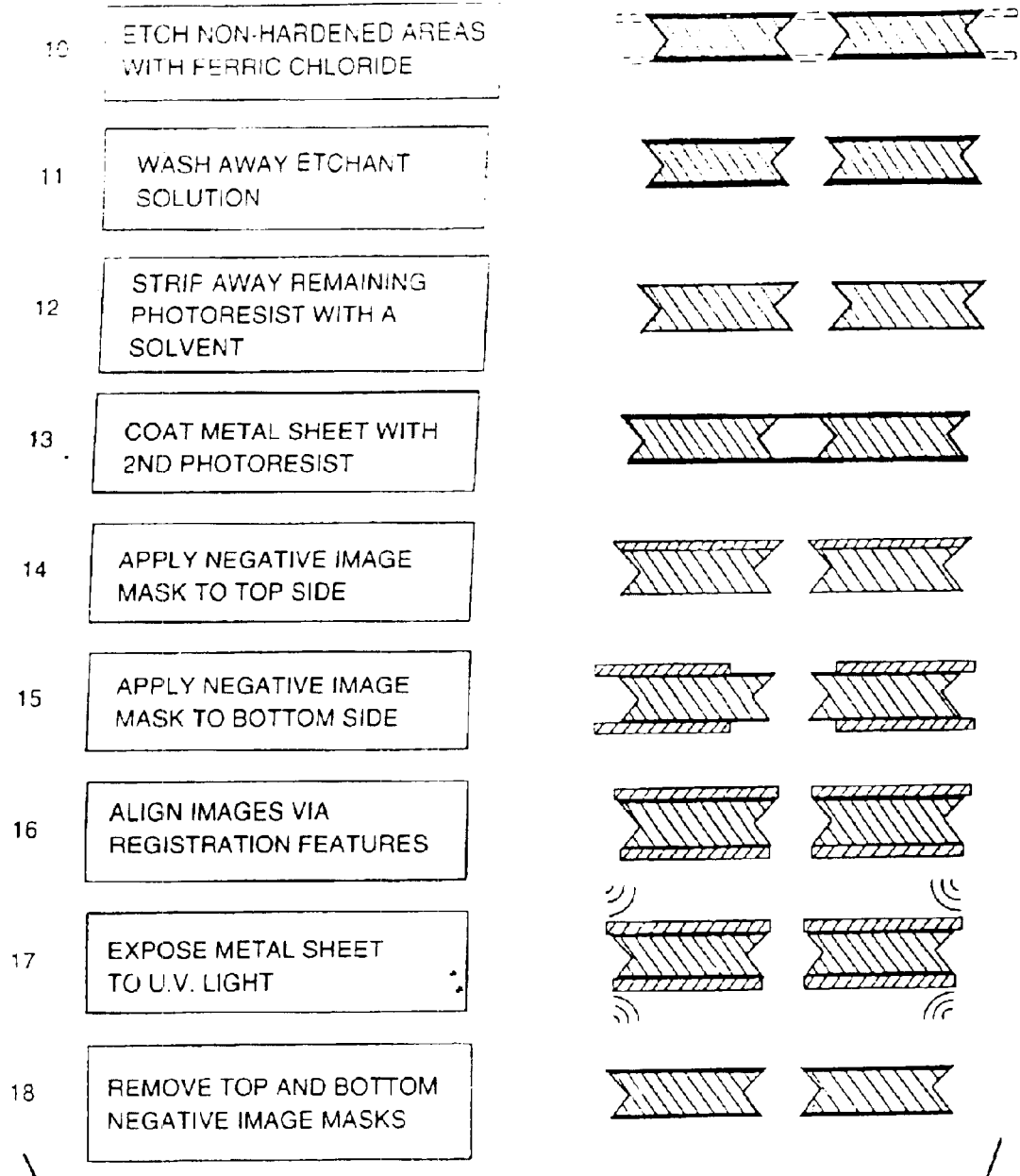
Figure 59C:
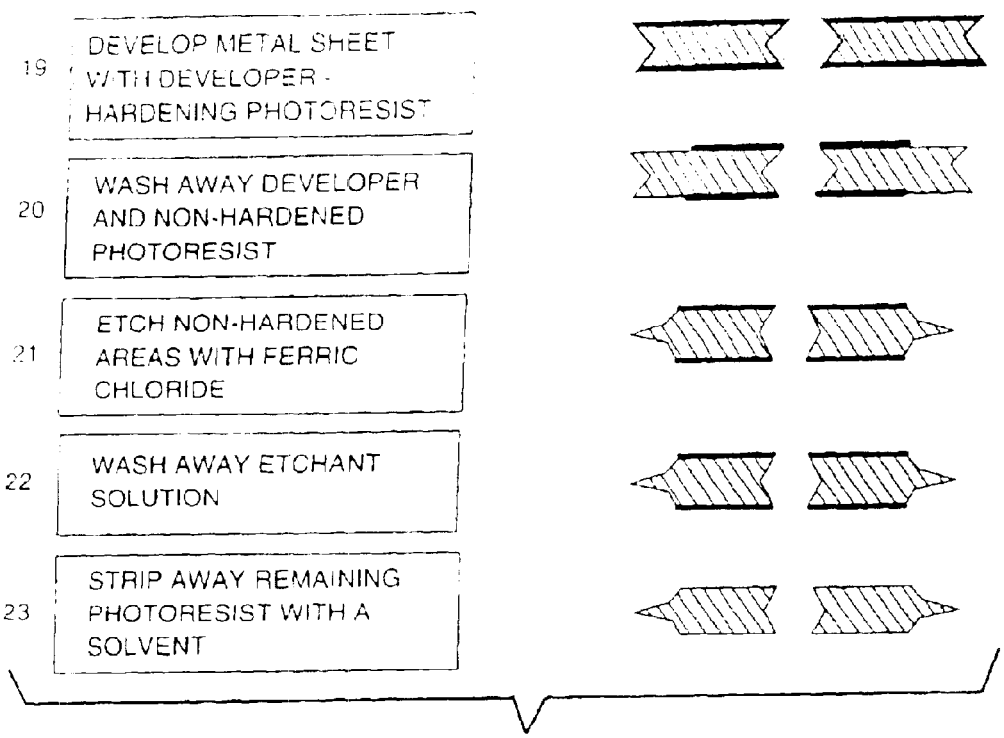

FIG. 59 is a flow chart showing the process of the present invention.

Figure 60:
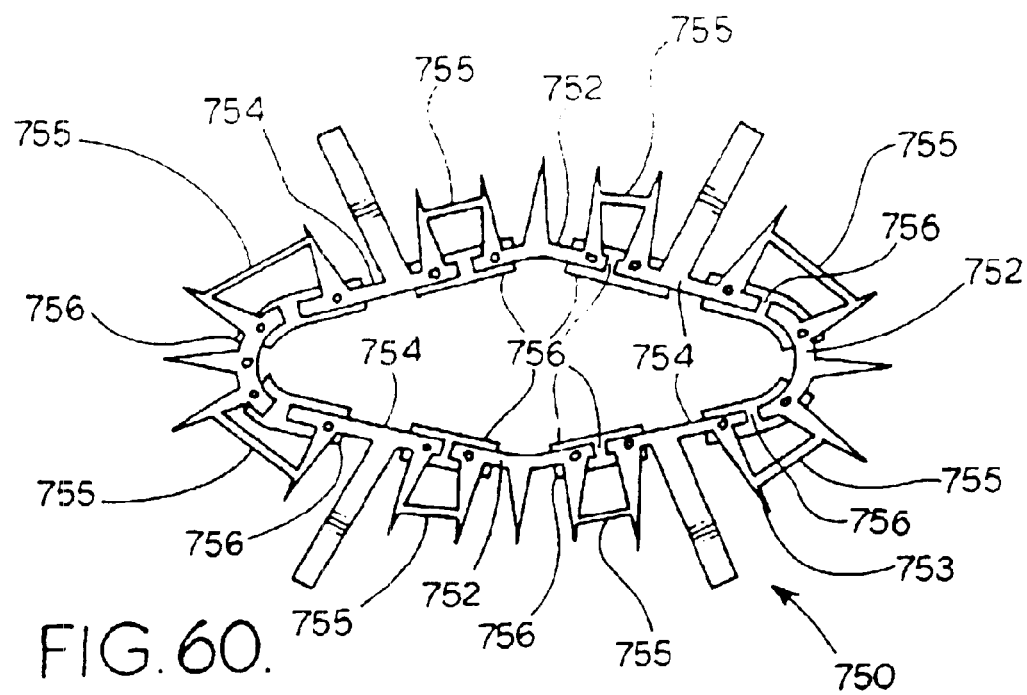

FIG. 60 shows another form of the mounting structure of the present invention with absorbable portions.

Figure 61:
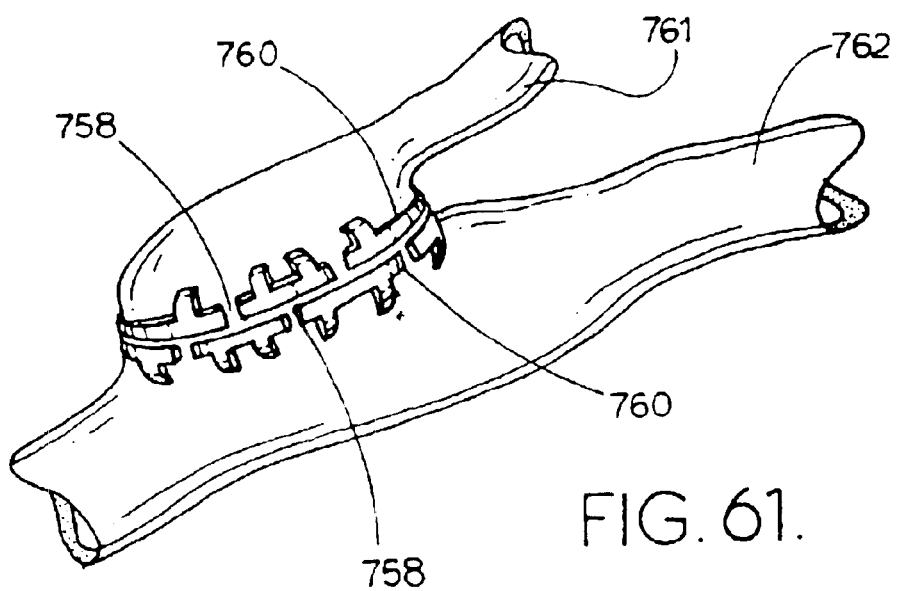

FIG. 61 shows the FIG. 60 mounting structure in place after the absorbable portions have been absorbed.

Figure 62A:
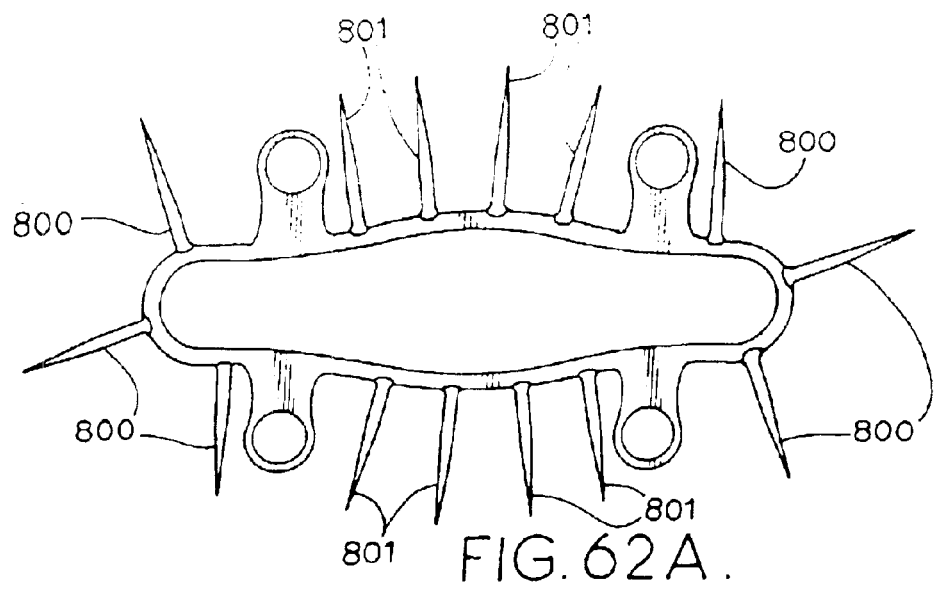

FIG. 62A is a top plan view of a malleable ring-shaped stent structure showing spacing and size for the tines.

Figure 62B:
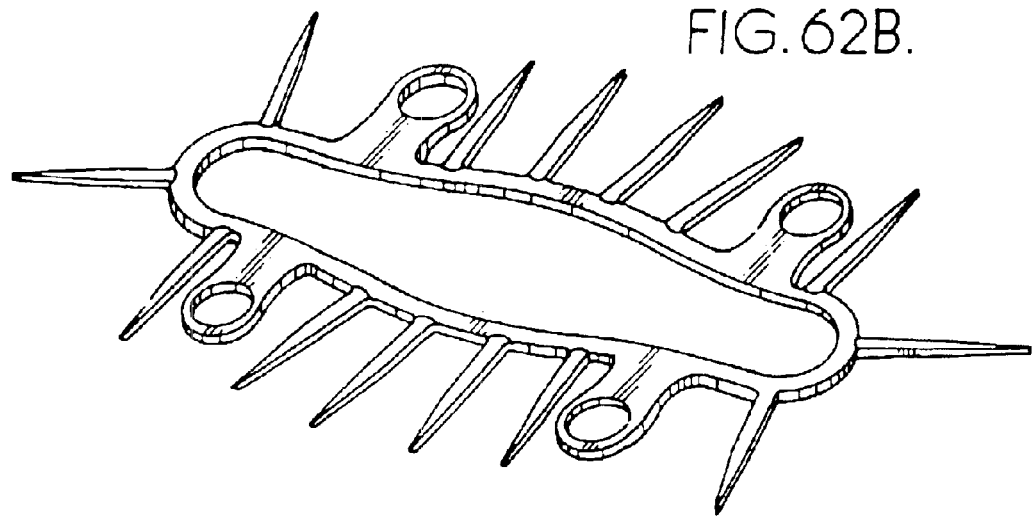

FIG. 62B is a perspective view of the stent structure shown in FIG. 62A.

Figure 63:
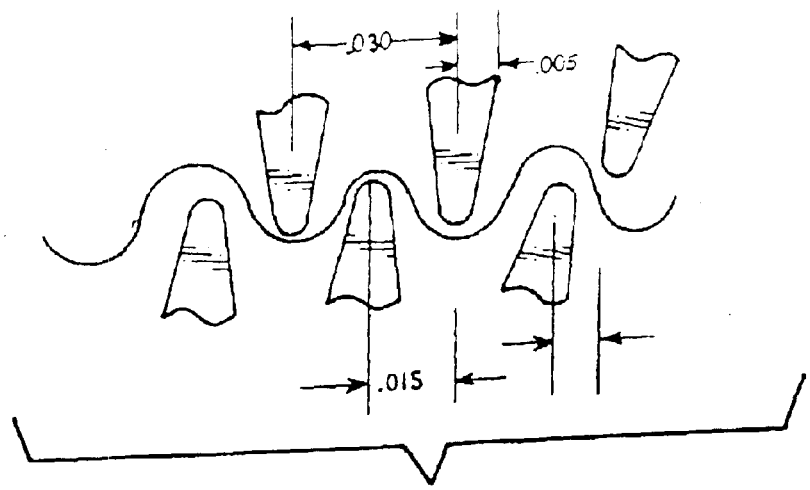

FIG. 63 illustrates spacing and sizing for the best mode of the malleable stent of the present invention.

Figure 64A:
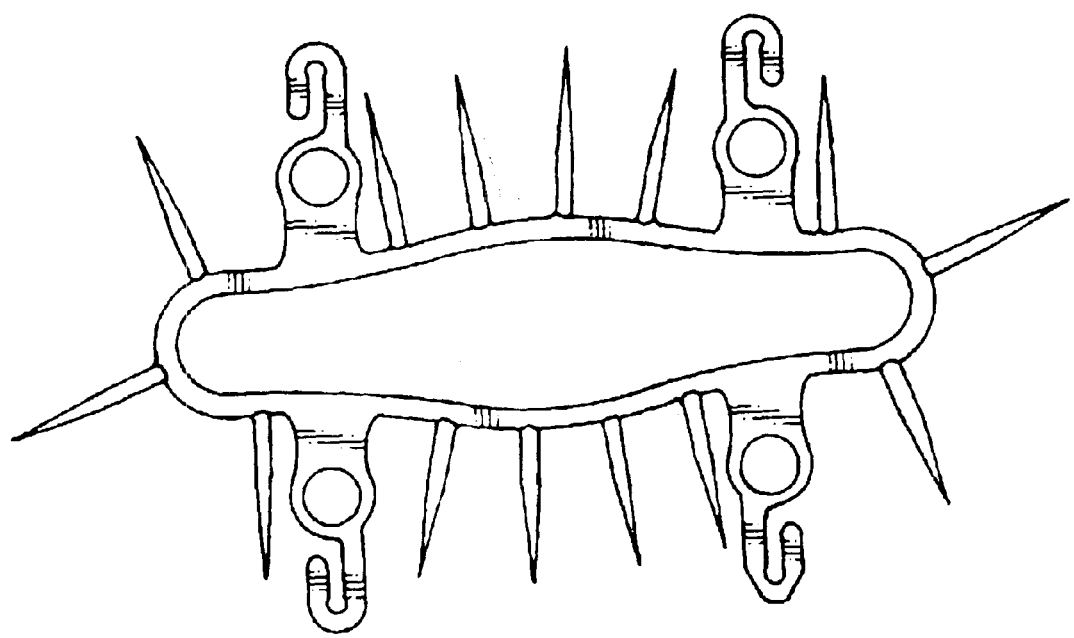
Figure 64B:
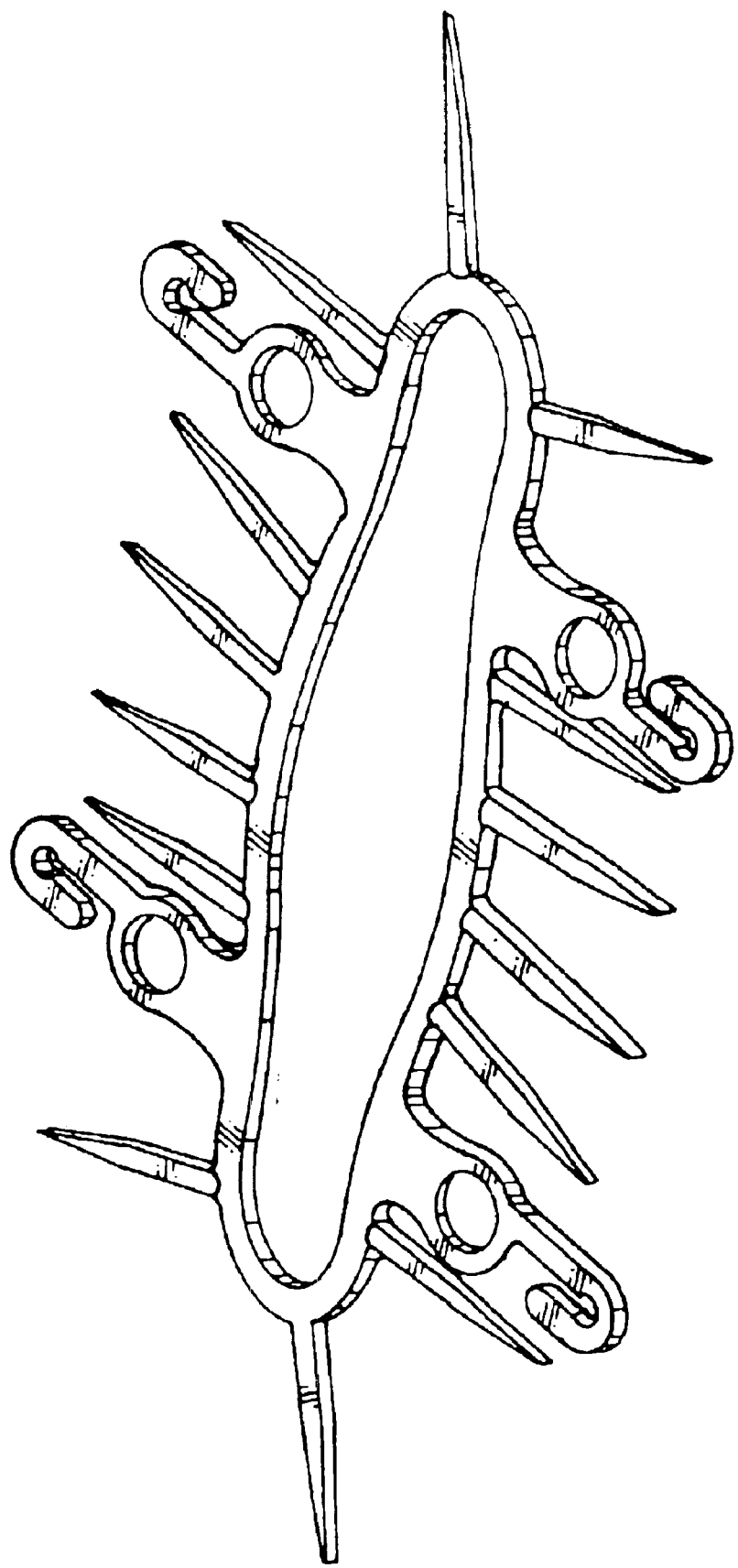

FIGS. 64A and 64B illustrate yet another alternative form of the malleable ring-shaped stent with manufacturing dimensions thereon.

DETAILED DESCRIPTION OF THE PREFERRED EMBODIMENT OF THE INVENTION

Locating and Performing the Arteriotomy

Figure 1:
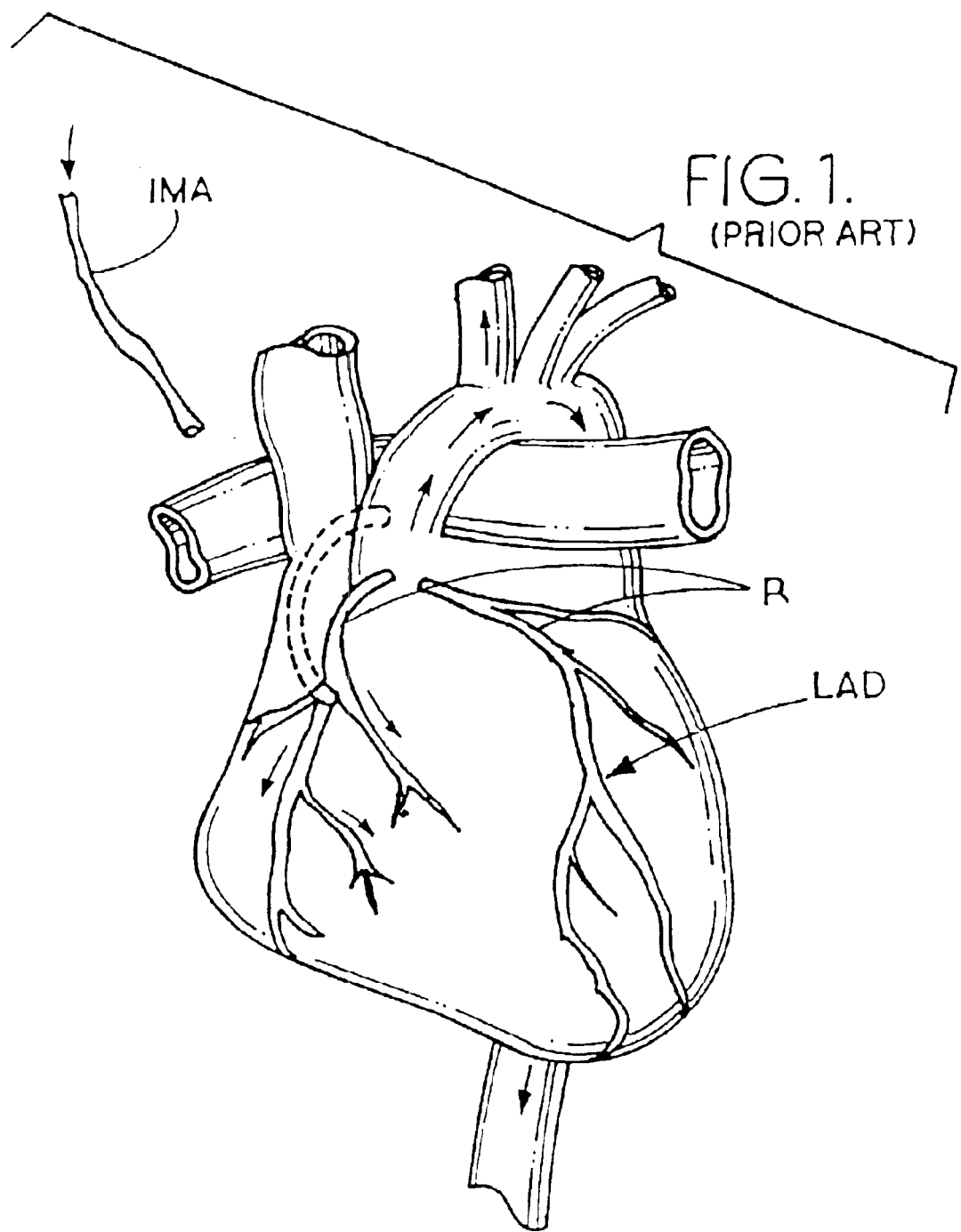
FIG. 1 is a schematic showing a heart.
Figure 2:
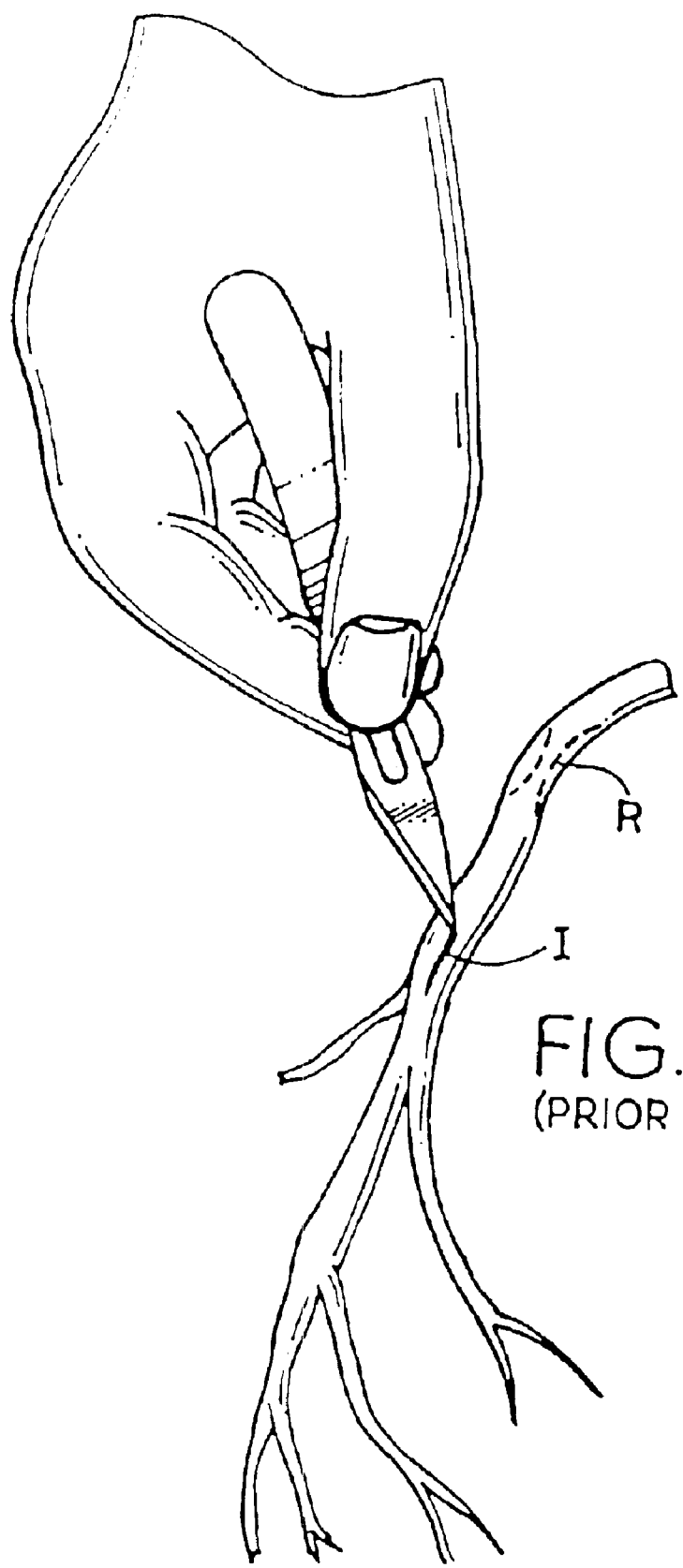
FIG. 2 illustrates a prior art method of locating an incision in an artery for performing an anastomosis.

By way of orientation, FIGS. 1 and 2 indicate the procedure used in locating and performing of an arteriotomy. As is well understood to those skilled in the art, locating the position of an anastomosis is extremely important and extremely delicate. The location must be selected with extreme accuracy and precision. This is especially necessary since the blood vessels are often extremely small. This is indicated in FIGS. 1 and 2 where the location of a restriction is indicated as R and an arteriotomy is indicated at I in FIG. 2. The arteriotomy must be made in a proper location with respect to the restriction R or the surgery will not be as effective as it could be. Furthermore, an anastomosis must be performed accurately and effectively to be successful. The present invention discloses and teaches a means and a method of performing such an anastomosis.

Figure 3:
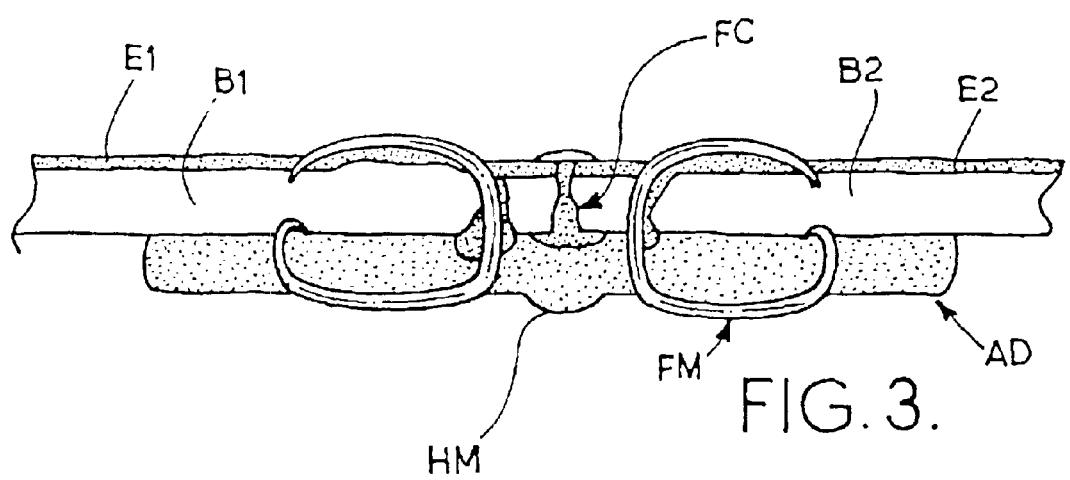
FIG. 3 illustrates an anastomosis which includes a hemostatic medium located in a manner that clots will form externally of the blood vessel.

As discussed in the parent applications, the present invention is intended to permit the performance of an anastomosis in a minimally invasive manner yet to perform the procedure in an accurate manner and in a manner that promotes proper healing. The most effective healing will occur when the hemostatic medium is located on the outside of the blood vessel so any clots will form on the outside of the vessel. This basic concept is illustrated in FIG. 3 which shows an anastomotic device AD comprising a hemostatic medium HM having a stent which includes a fastening element FM for fastening the stent to the vessel and which is located on the outside of one blood vessel B1 which is to be joined to another blood vessel B2 and for bringing vessel walls, and the endothelial lining E1, of the one blood vessel into intimate approximation with other vessel walls, represented by endothelial lining E2, of the other blood vessel whereby fibrin clot FC is formed in the proper location to effect a successful procedure. Still further, excessive clamping is avoided in the present invention by obviating the need for clamps, such as are commonly used in prior art techniques.

Cuff

Figure 6:
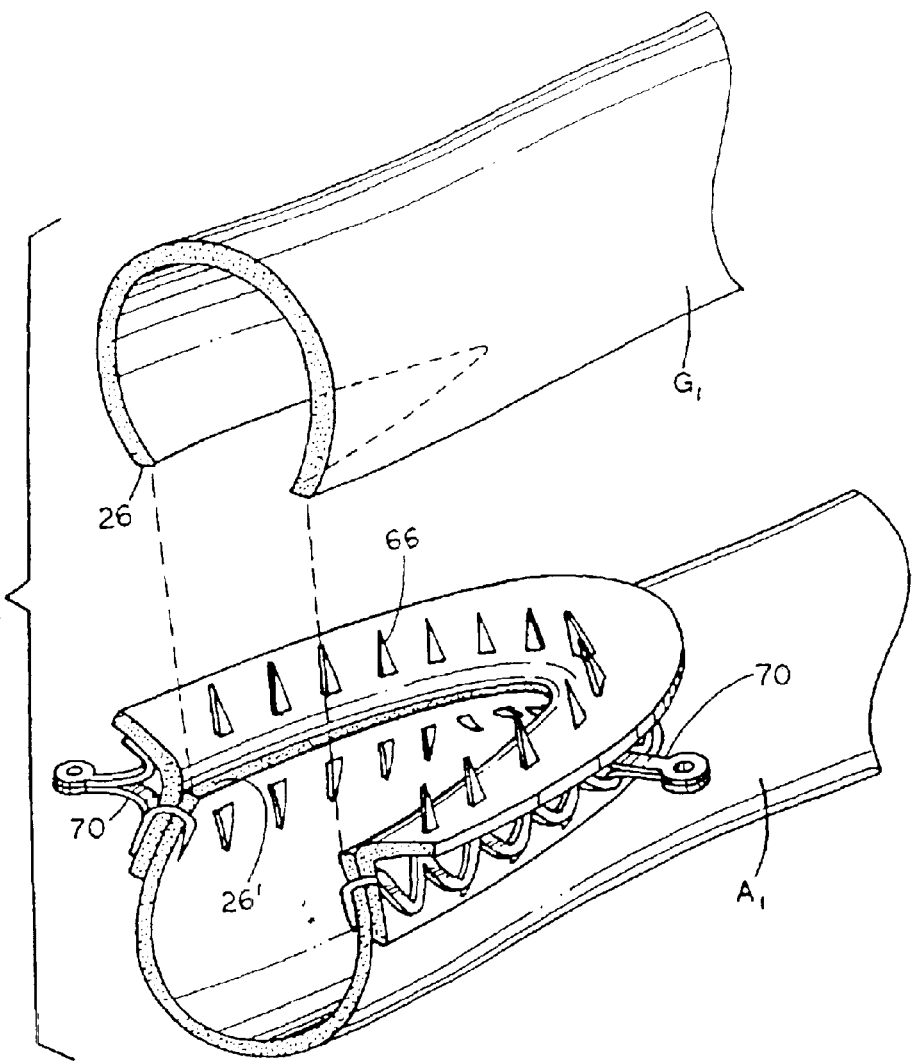
FIG. 6 is an exploded perspective view showing a single cuff form of the invention prior to joining a graft and an artery.
Figure 7:
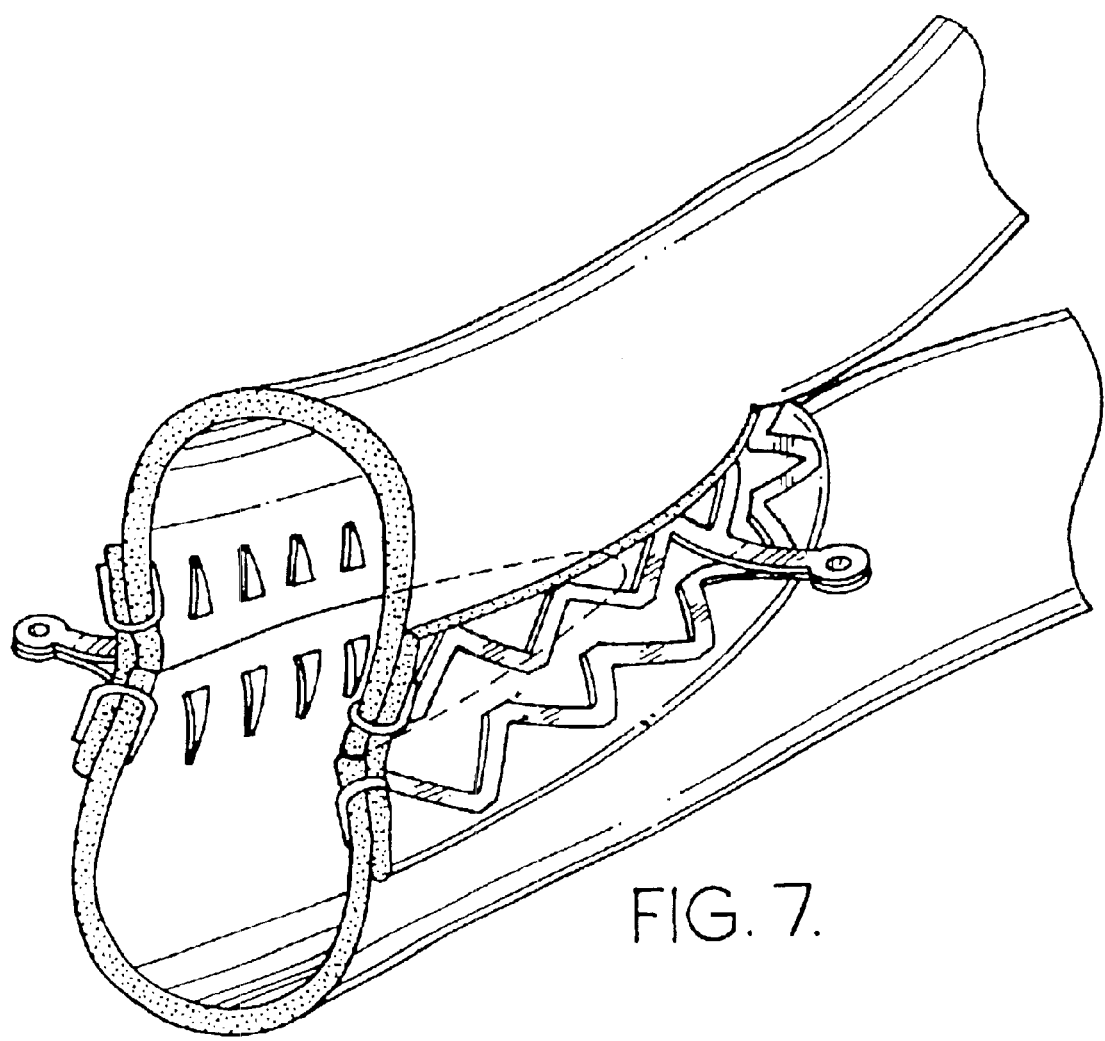
FIG. 7 is a cut away view showing the single cuff form after the graft has been joined to the artery.
Figure 8:
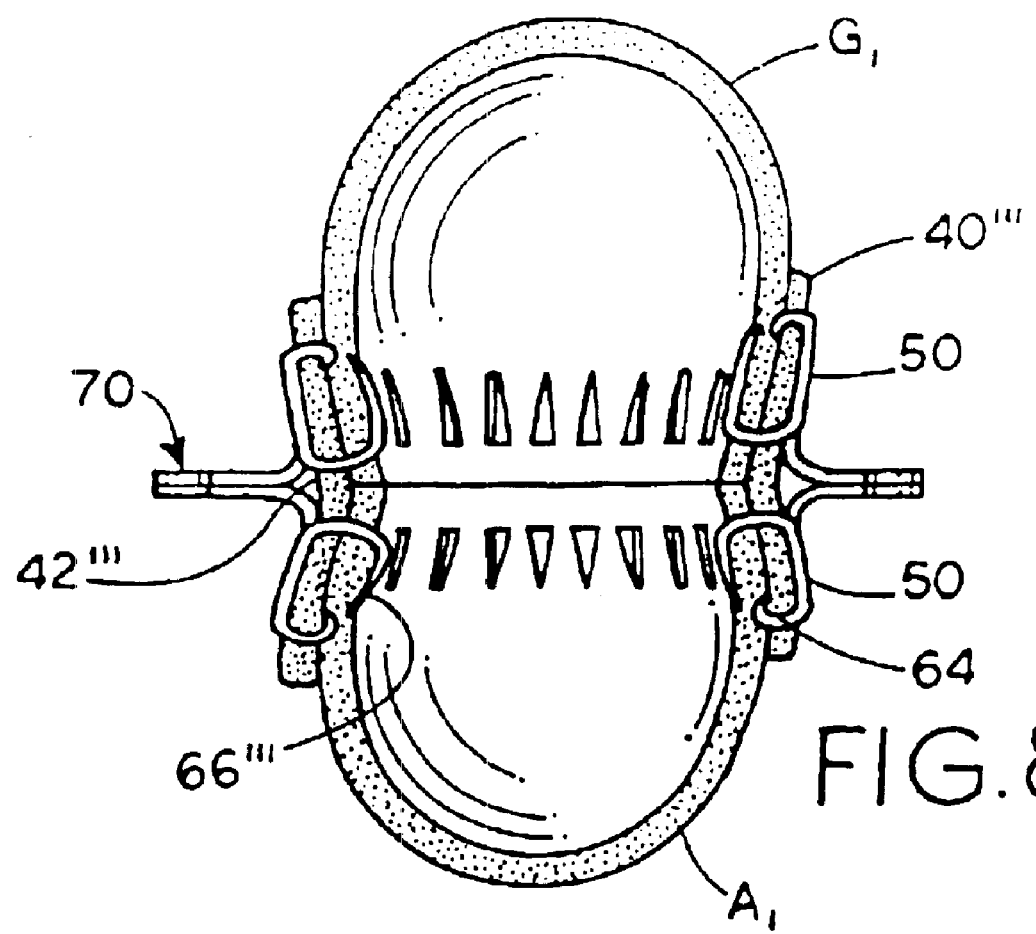
FIG. 8 is an elevational cross-sectional view of the single cuff form of the invention joining a graft to an artery.
Figure 9:
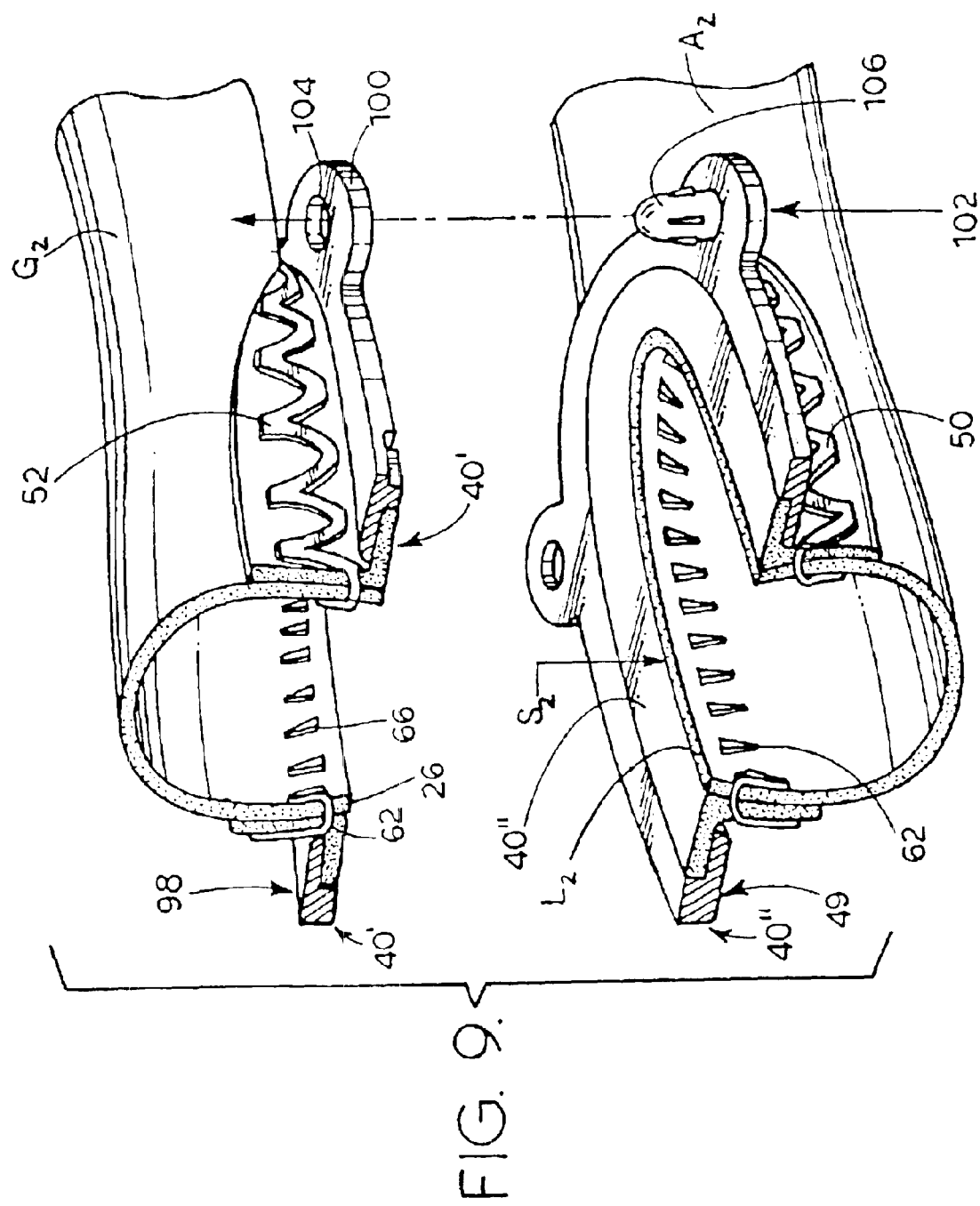
FIG. 9 is an exploded perspective view of one form of the invention in which two cuffs are used to join an artery with a graft.
Figure 10:
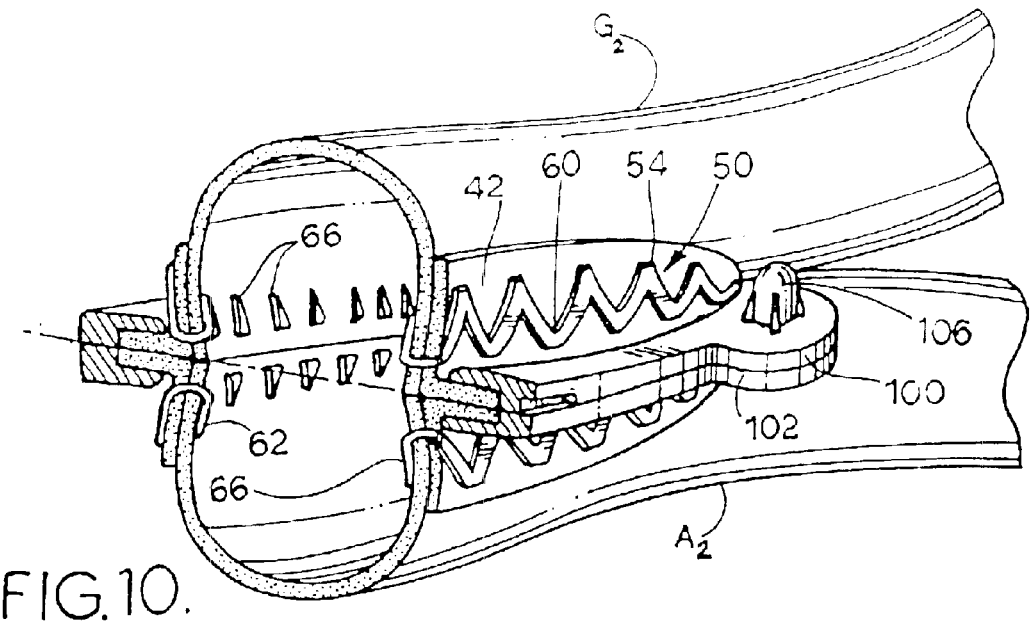
FIG. 10 is a perspective view of a section of the joined artery and graft using two cuffs.
Figure 11:
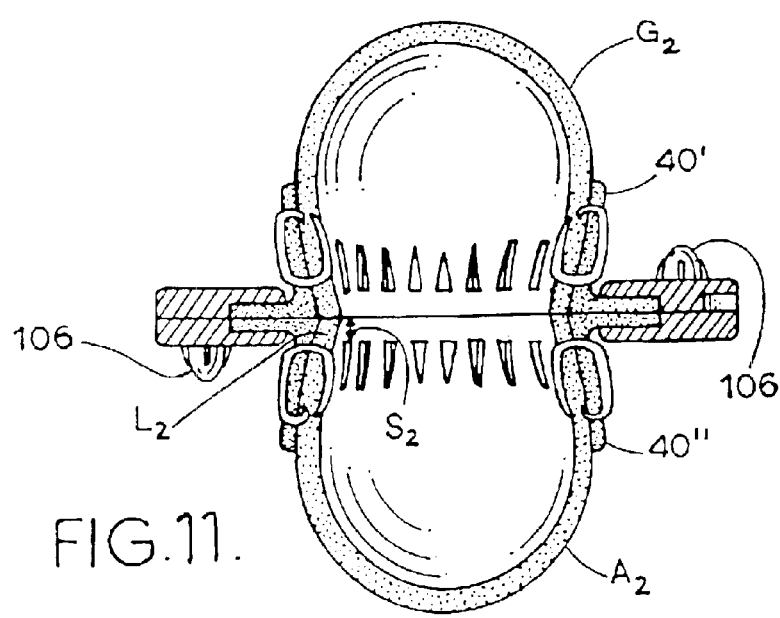
FIG. 11 is an elevational cross-sectional view of the two cuff form in situ.
Figure 12:
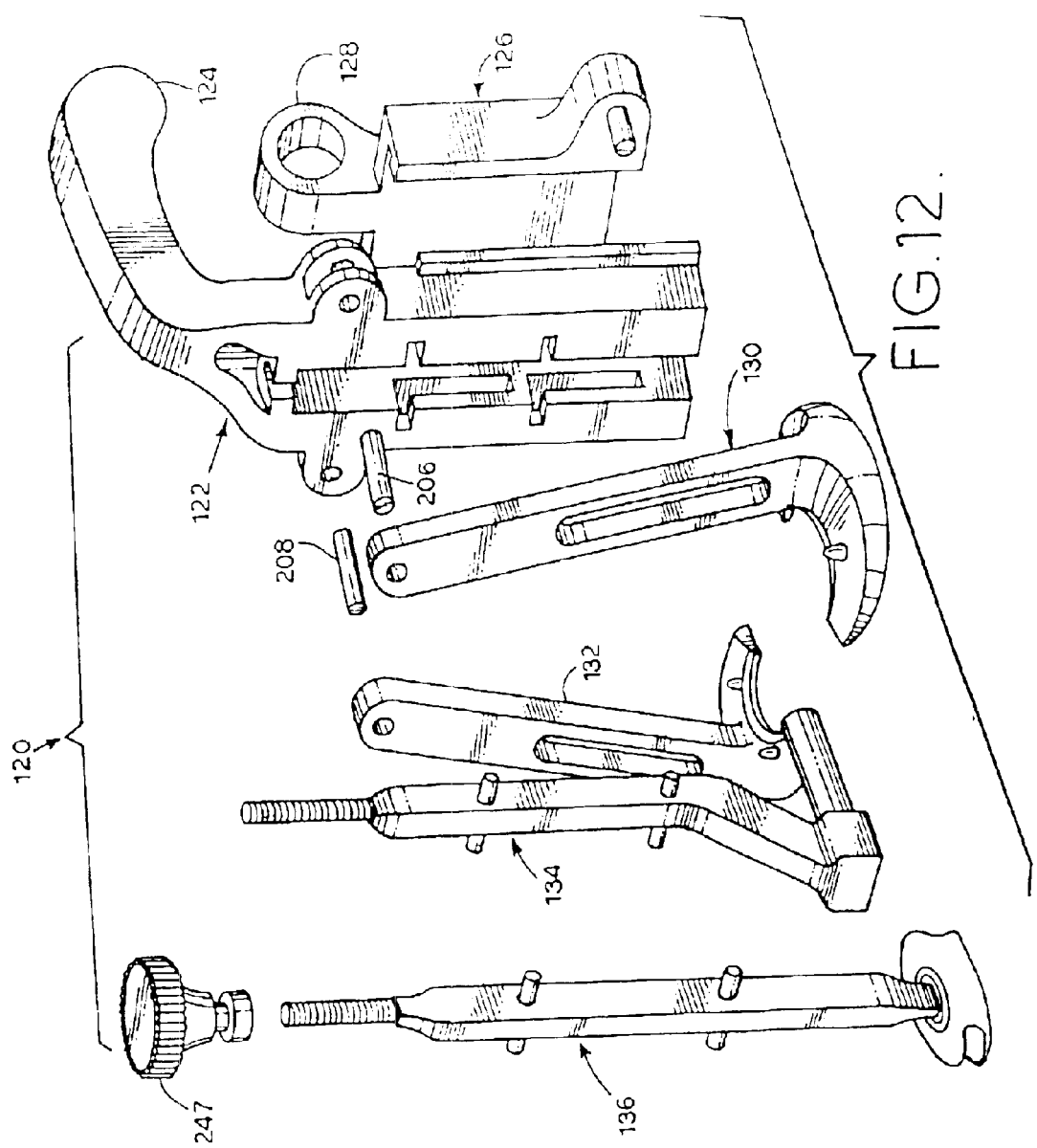
FIG. 12 is an exploded perspective view of a tool used in performing the anastomosis.

There are two forms of the invention, a single cuff form (see FIGS. 11–18B of the parent and FIGS. 6–8 herein) and a double cuff form (see FIGS. 19–24 of the parent and FIGS. 9–11 here). In the interest of brevity, this mounting element will be referred to as a cuff. However, no limitation is intended by this shorthand reference.

The single cuff form of the invention has one portion mounted on artery $A_1$, and another portion mounted on graft blood vessel $G_1$ with vessels $A_1$ and $G_1$ being brought into contact with the vessel attaching elements of the cuff to attach the two vessels together. It is here noted that for the sake of brevity, the discussion will be directed to blood vessels; however, those skilled in the art will be able to understand that the teaching can be applied to vessels of any sort that occur in a patient. Accordingly, no limitation is intended by the reference to a "blood" vessel. The double cuff form of the invention shown in FIG. 9 has one cuff attached to graft $G_2$ and a separate cuff attached to artery $A_2$. These cuffs are then attached to each other to effect the connection. The single cuff form of the invention has a single cuff attached to both the graft blood vessel and to the artery, with the single cuff attaching the two blood vessels together to effect the connection. The double cuff form of the invention has each cuff individually mounted on a blood vessel by an instrument, and the two cuffed vessels brought together with the cuffs then coupled together.

Figure 4A:
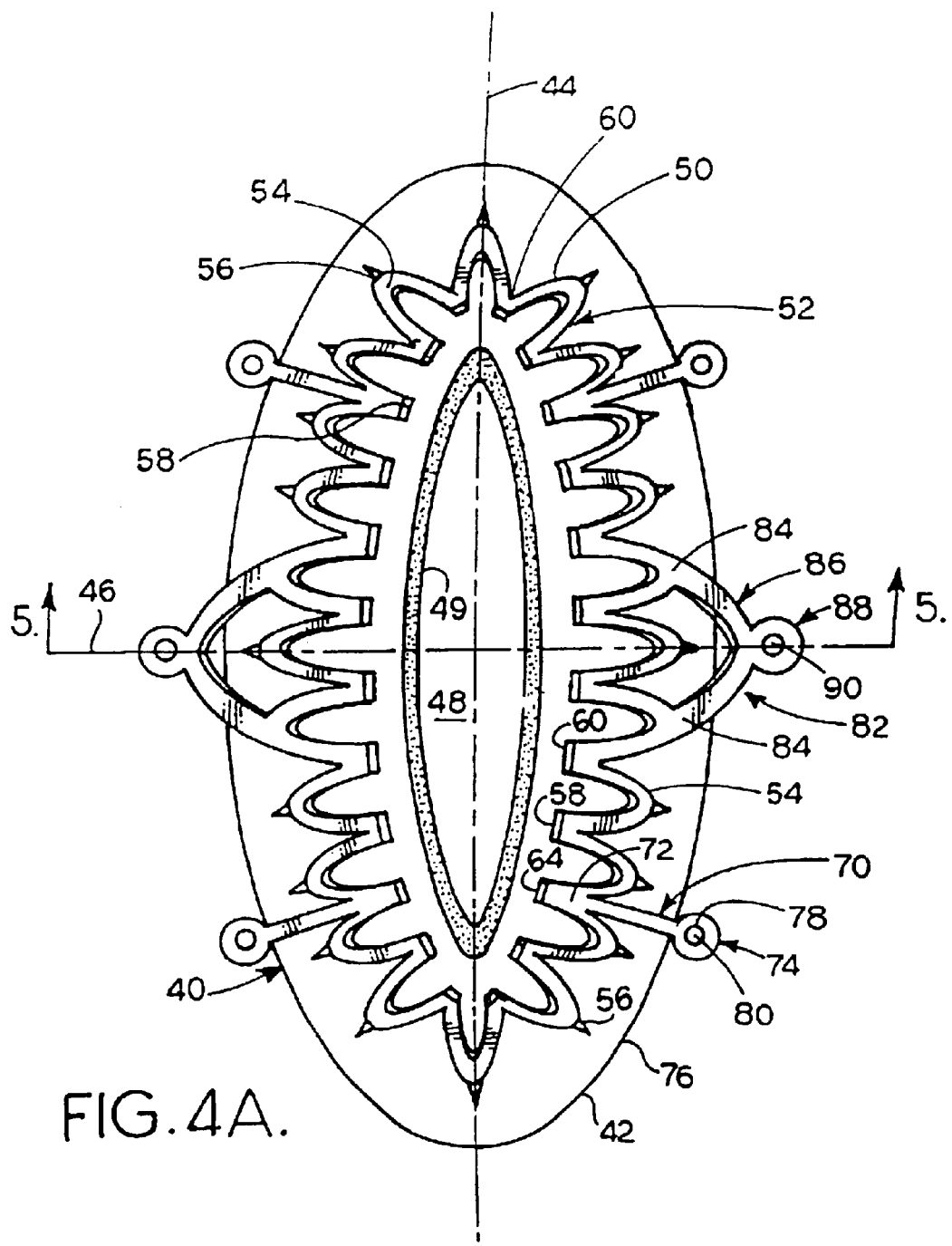
FIG. 4A is a view taken along line 4A—4A of FIG. 4.

Shown in FIGS. 4, 4A and 5 is a single cuff 40 embodying the present invention. The cuff is applied to a blood vessel and will couple that vessel to another vessel or to another cuff. The cuff can be applied to a blood vessel by an instrument while blood still flows through the vessel by using a stabilizing cuff installation tool with a flow-through anvil. This enables anastomotic surgery to be performed without stopping the heart so the procedure can be carried out in a minimally invasive manner. The cuff also permits proper shaping of the junction without mishandling the blood vessels and places the two vessels in an orientation that promotes efficient healing.

Specifically, cuff 40 includes an oval shaped flexible body 42 having a long axis 44 and a short axis 46 with an oval shaped opening 48 defined therein by cuff body waist section 49. The preferred form of body 42 is a woven fabric suitable for use in surgery. A stiffening framework or stent 50 of malleable material, is integrated into body 42 for retaining the cuff in a selected shape on a blood vessel. The preferred form of the framework is sinuous and includes a plurality of malleable sections, such as section 52. In the present context, this element will be referred to as a retention element. However, as will occur to those skilled in the art based on the teaching of the present disclosure, depending on the context of the discussion, this element can also be referred to as a "stent" or a "stiffening band." One form of the material is a wire that is suitable for use in the surgical environment associated with this invention. The retention element has little material memory in that once deformed from one shape into another, it will not move back into the first shape from the second. A second potential form for the retention element is shaped from flat stock which is processed using precise methods such as wire EDM or photo etching. Shaping the cuff is therefore efficiently carried out by deforming it into the desired shape after it is mounted on a blood vessel. The retention element will maintain the cuff in the shaped condition. Sections of the stiffening framework may be separate from other sections, such as quartered sections or the like.

Each malleable section has an apex, such as apex 54, with a cuff retaining pin, such as pin 56, thereon. Cuff retaining pins 56 attach the stiffening framework 50 to the cuff, and anchor elements 58 attach base 60 of each section 52 to body 42 to securely anchor the stiffening framework to body 42. However, many cuff pins may be used to secure the cuff frame to the cuff.

As indicated in FIG. 5, tissue retention pins or fasteners 62 are attached at a proximal end 64 thereof to body 42 and have a distal end 66 which engages a blood vessel to anchor the cuff to that blood vessel in the manner of a surgical staple. The instrument discussed below is used to force the retention pin into the blood vessel tissue to anchor the cuff to the blood vessel.

Apparatus for shaping the cuff once it is anchored on the blood vessel includes docking extensions, such as docking extensions 70 having a proximal end 72 unitary with a base of a malleable section of the stiffening framework and a distal end 74 spaced from the outer perimeter 76 of the cuff body 42. An eyelet 78 is located on distal end 74 having a central hole 80 defined therein to engage a corresponding element on the instrument used to place the cuff. The apparatus for shaping the cuff also includes a plurality of second docking extensions 82 having proximal ends 84 integral with alternate apexes of the stiffening framework 50 and a distal end 86 having an eyelet 88 with a central hole 90 for releasable connection to a corresponding element on the instrument used to place the cuff.

As was discussed in the parent application, the docking extensions are engaged with the instrument, and once the cuff is anchored to a blood vessel, the instrument can be manipulated by the surgeon to shape opening 48 to the desired size and shape. Once the desired size and shape have been established, the cuff and framework is released from the instrument and will retain the desired shape and size.

As can be seen in FIG. 4, the cuff has an hour glass shape in elevation, with body 42 having a first end section 92 and a second end section 94 of roughly the same outer dimension, with central section 95 having an outer dimension of less than those outer dimensions. Other forms of the single cuff are illustrated in the parent application with respect to FIGS. 13A–13F.

As is also discussed in the parent application, the present invention can include a double cuff. As can be seen (see, e.g., FIG. 11), one cuff 40' is attached to a graft blood vessel $G_2$, and a second cuff 40" is attached to the artery $A_2$. As can be seen in FIG. 9, there is a spacing $S_2$ between the fastening elements attaching the cuff to the vessel and the edge of the artery. This spacing is selected as the loose edge $L_2$ of the vessel can still be controlled, but the fastening element is not located too close to the edge of the vessel. Bringing the cuffs together in this manner does not mishandle the blood vessels and promotes efficient healing of the junction. A spacing $S_2$ of ½ mm to 1 mm is shown in FIG. 9. However, this spacing is disclosed for the sake of completeness and is not to be taken as limiting.

Figure 22:
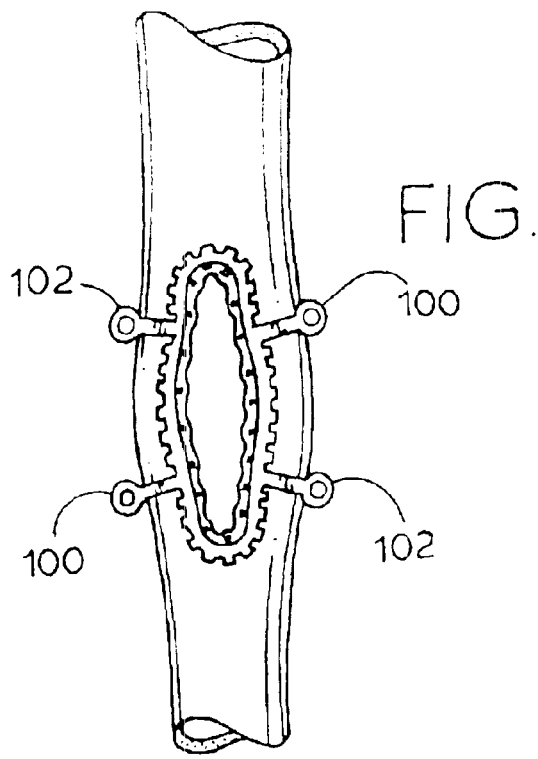
FIG. 22 shows a malleable ring-shaped stent attached to a vessel in a late stage of the fastener forming process.
Figure 23:
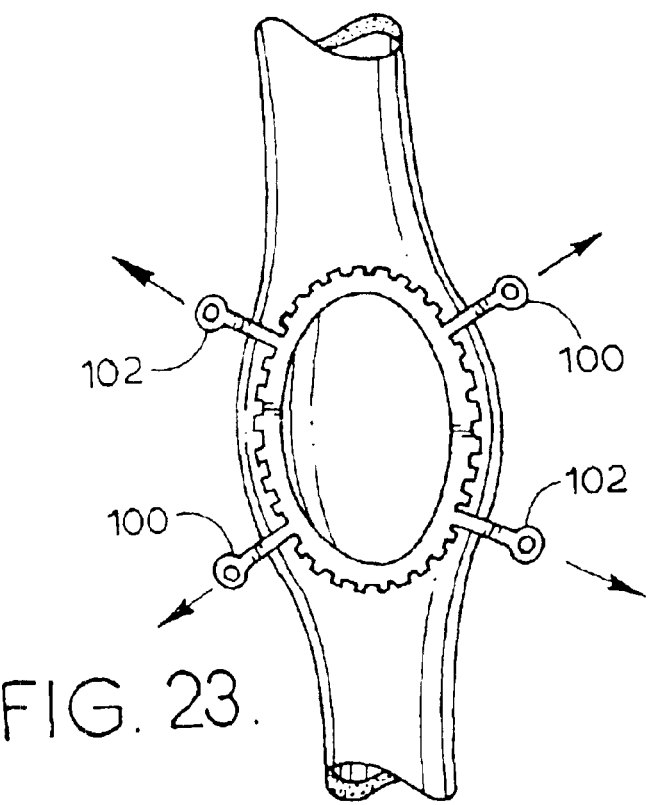
FIG. 23 shows the malleable ring-shaped stent after it has been stretched to permit removal of the anvil portion of the tool used to form the fastener.

Referring to FIG. 9, means for joining one cuff to the other in the double cuff form of the invention includes one unit 98 fixed to the graft blood vessel $G_2$ and one unit 99 fixed to the artery $A_2$. A female section 100 is fixed to cuff 40' and a corresponding male section 102 is fixed to cuff 40". Female section 100 includes an eyelet 104 that has an opening sized and shaped to snugly receive a male element 106 mounted on section 102 to establish a friction fit between elements 100 and 102 that securely couples the two cuffs together. The preferred form of the cuff joining means includes four male elements and four female elements on each unit 98 and 99, each being located on opposite sides of the cuffs as is shown in FIGS. 22 and 23. Each cuff has two male elements and two female elements with the male elements on each base whereby a secure attachment is effected.

As can be understood by those skilled in the art by comparing FIGS. 8 and 11, the double cuff form of the invention uses two cuffs, such as 40' and 40", to attach two blood vessels together, whereas, the single cuff form of the invention uses a single cuff 40''' to attach two blood vessels together. The double cuff form of the invention has two similar cuffs attached together by a coupling means. The single cuff form of the invention has a single cuff with the two ends thereof identical each having a stiffening framework therein and each having tissue retention pins 62''' therein. A single body unitary 42''' forms the cuff 40'''.

Both forms of the invention, the single cuff and the double cuff, can be used to form both a side-to-side anastomosis and the double cuff form can be used to form an end-to-side anastomosis.

The double cuff form of the invention is applied as indicated in FIGS. 9 and 11. A tool such as discussed in the parent application, is used to place a cuff on the graft, and then a second cuff on the artery. The vessels are then oriented adjacent to each other as indicated in FIG. 9, and then brought together so the two cuffs are coupled as indicated in FIG. 10. The cuffs are then coupled together as indicated in FIG. 11 to form an end-to-side anastomosis or to form a side-to-side anastomosis. The two cuffs are coupled together by a suitable fastener, such as the above-discussed male/female coupling shown in FIG. 11.

Instrument

As discussed above, the anastomosis technique of the present invention is intended to be performed in a minimally invasive manner. Therefore, the cuffs discussed above must be placed on blood vessels that are located inside a patient, with the artery carrying blood. As was also discussed above, the anastomosis technique of the present invention may involve extremely small blood vessels. Accordingly, the instrument used to effect the anastomosis must be very accurate and precise, and yet not mishandle the blood vessels during performance of the technique. The instrument will place a cuff on the artery while permitting blood to flow through that artery, and then will place a corresponding cuff on the graft blood vessel, or will attach the graft blood vessel to the single cuff mounted on the artery in the single cuff form of the invention. The instrument will then be used to shape the cuffs so the junction is the most efficient and will permit proper healing. All of this must be carried out in a minimally invasive manner.

Figure 13:
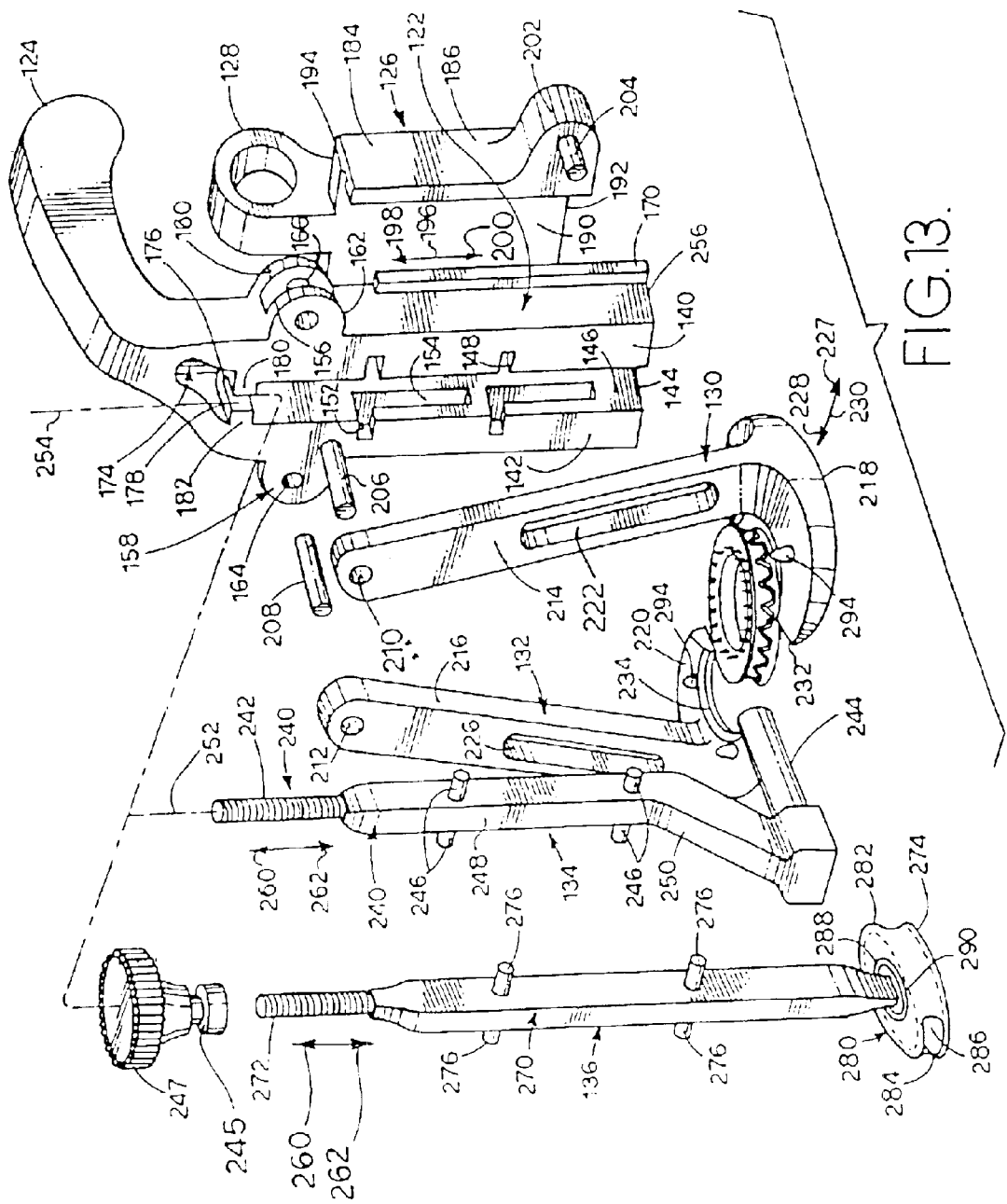
FIG. 13 is an exploded perspective view of the FIG. 12 tool used in performing the anastomosis with a cuff in place.

The preferred form of the instrument used to mount a cuff to the artery in both forms of the invention and to mount the cuff to the artery and to the graft in the double cuff form of the invention is shown in FIGS. 12–17, with FIG. 13 showing a cuff in conjunction with the instrument. Instrument 120 broadly comprises a handle frame 122 having a handle 124 that is grasped by a surgeon during operation of the instrument, and a finger frame 126 having a finger grip 128 which is operated by the surgeon, two driver arms 130 and 132 pivotally attached to the handle frame, a graft anvil 134 and an artery anvil 136.

More specifically, handle frame 122 includes a U-shaped section having legs 140 and 142 attached at one end to handle 124 and which are spaced apart to define a channel 144 therebetween. Each leg has an inside surface 146 with L-shaped anvil alignment slots 148 and 150 defined in the legs to have short legs 152 that intersect the channel and long legs 154 defined to be parallel to the channel. The function of the anvil slots will be understood from the discussion in the parent and the following discussion.

The handle frame further includes two ears 156 and 158. The ears include two spaced apart plates 160 and 162 with bores 164 and 166 defined in each plate to be centrally aligned with each other for a purpose that will be understood from the discussion in the parent disclosures. The handle frame further includes two rails 170, on the outer edges of the legs 140 and 142.

An undercut region 174 is formed in the proximal end of the handle frame and provides a lip 176 having a top shoulder at the top entrance to channel 144. Lip 176 is U-shaped and has a channel 178 defined between leg 180 corresponding to leg 140 and leg 182 corresponding to leg 142.

Finger frame 126 includes a U-shaped base 184 having two legs 186 each connected to a center section 190 and defining a channel 192 therebetween. A slot 194 is formed at the intersection of each leg and the center section, with slots 194 being sized and located to slidably receive rails 170. Sliding engagement between the rails and the slots permits the finger frame to move with respect to the handle frame longitudinally of the channel 192 as is indicated by the double-headed arrow 196, with handle frame 122 moving in direction 198 with respect to finger frame 126 to open the instrument anvils and moving in direction 200 with respect to the finger frame to close the instrument anvils as will be discussed below.

Each leg 186 of the finger frame 126 further includes an ear 202 on a distal end thereof to which a guide pin 204 is fixed to extend past the handle frame leg adjacent thereto.

Instrument 120 further includes two pivot pins 206 and 208 accommodated in the aligned bores 164 and 166. Each of the driver arms 130 and 132 has a pivot pin receiving hole 210 and 212, respectively, defined in the proximal ends 214 and 216, respectively, of the arms. Crescent-shaped driver heads 218 and 220 are located on the distal ends of the arms 130 and 132, respectively, with cam slots 222 and 226 being defined in the arms 130 and 132, respectively.

Figure 15:
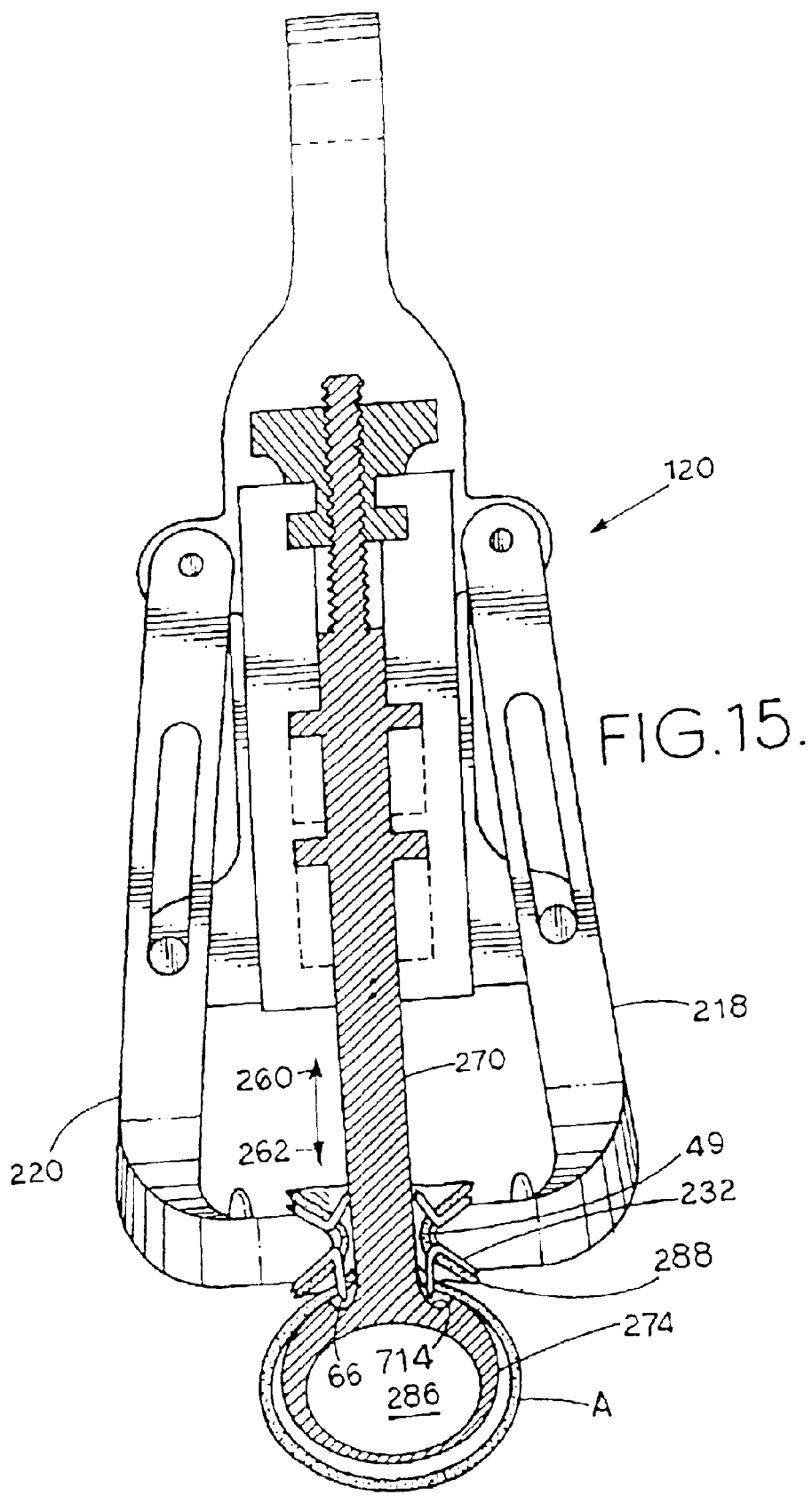
FIG. 15 is an elevational view, with parts shown in section, of the FIGS. 12 and 13 tool in place in an artery just prior to setting a cuff on the artery.

The arms are pivotally attached to the handle frame by the pins 206 and 208 to move in directions 227 and 228, as indicated by double-headed arrow 230, when finger frame 126 moves in directions 198 and 200, respectively, to open and close the driver heads 218 and 220. Slots 222 and 226 slidably receive guide pins 204 to effect this opening and closing movement. Since the driver arms are secured to handle frame 122 by pivot pins 206 and 208 and guide pins 204 move longitudinally with respect to the handle frame and slidably engage cam slots 222 and 226, longitudinal movement of the finger frame with respect to the handle frame will cause the above-mentioned pivotal movement of the driver arms. The opening and closing of the driver arms is illustrated in FIGS. 15 (closing) and 16 (opening).

Each driver head, 218, 220 has a V-shaped cuff-engaging edge 232 which is sized and shaped to engage the waist section 49 of a cuff. Each edge 232 also has two surfaces 234 that diverge away from each other from the edge 232 to engage surfaces 236 and 238 (see FIG. 4) respectively of the cuff sections 92 and 94. Engagement of the surfaces 234 with the surfaces 236, 238, along with movement of the anvils 134 and 136, forces the tissue fasteners 62 into the tissue of the blood vessel while shaping the cuff to the blood vessel.

The tissue fasteners must be turned in the manner of a staple in order to fully connect a cuff to a blood vessel. Accordingly, instrument 120 includes artery anvil 136 and graft anvil 134 which are removably fixable to the handle frame. Graft anvil 134 includes a body 240 having a threaded portion 242 on a proximal end thereof, a graft anvil head 244 on a distal end thereof and alignment pins 246 between the two ends thereof. A fastening knob 247 is also included with instrument 120, and is internally threaded to threadably engage threaded portion 242.

Knob 247 is accommodated in undercut region 174 and threaded portion 242 is extends through channel 178 to be engaged by the threaded portion of the fastening knob 247. Longitudinal movement of the graft anvil in directions 260 and 262 is effected by threading the knob 247 on the threaded portion 242. Threaded movement in one direction moves the graft anvil in direction 262 and threaded movement in the opposite direction moves the graft anvil in direction 260 whereby the location of the graft anvil head 244 with respect to the driver heads 218, 220 can be adjusted and set. The purpose of this movement will be understood from the discussion in this disclosure.

A groove 245 in knob 247 engages lip 176 of handle 124 to hold the knob against axial movement as the anvil moves up or down to bend or cinch the fasteners 62. Body 240 includes a first portion 248 and a second portion 250 that is angled with respect to the first portion 248. Graft anvil head 244 has a proximal end thereof fixed to portion 250 to extend transverse to longitudinal centerline 252 of the body 240. The length of body 240 as measured between its proximal and distal ends is greater than the length of the handle frame as measured along its longitudinal centerline 254 between the shoulder of the lip 176 and distal end 256 whereby graft anvil head 244 is spaced from distal end 256 when the graft anvil 134 is mounted on the handle frame. First portion 248 is also long enough so that graft anvil head 244 is also spaced from driver heads 218 and 220 when the graft anvil is in place on the handle frame. Alignment pins 246 are received through alignment slots 148 and 150 and are slidably accommodated in slots 154 so the graft anvil is securely and movably mounted on the handle frame.

Artery anvil 136 includes a body 270 having a threaded portion 272 on a proximal end thereof and an artery anvil head 274 on a distal end thereof. Alignment pins 276 are located on the body to be received through short legs 152 of slots 148 and 150 and slidably accommodated on the handle frame in the long portions of the slots 154. When the artery anvil is attached to the handle frame, threaded portion 272 extends through channel 178 and is threadably received by knob 247 to attach the artery anvil to the handle frame and to move that artery anvil in directions 260 and 262 with respect to the handle frame as was discussed above with regard to the graft anvil whereby the location of the artery anvil head 274 with respect to the driver heads 218, 220 can be set. The artery anvil head 274 is located beneath the driver heads so that the head can be inserted into an artery and a cuff being supported by the driver heads will be located outside that artery. Once the artery anvil head is positioned inside an artery, the knob 247 is operated to move the anvil head 274 toward the driver heads 218, 220 until the cuff supported in the heads 218, 220 engage the outside of the artery. The tissue retention pins can then be set.

Figure 16:
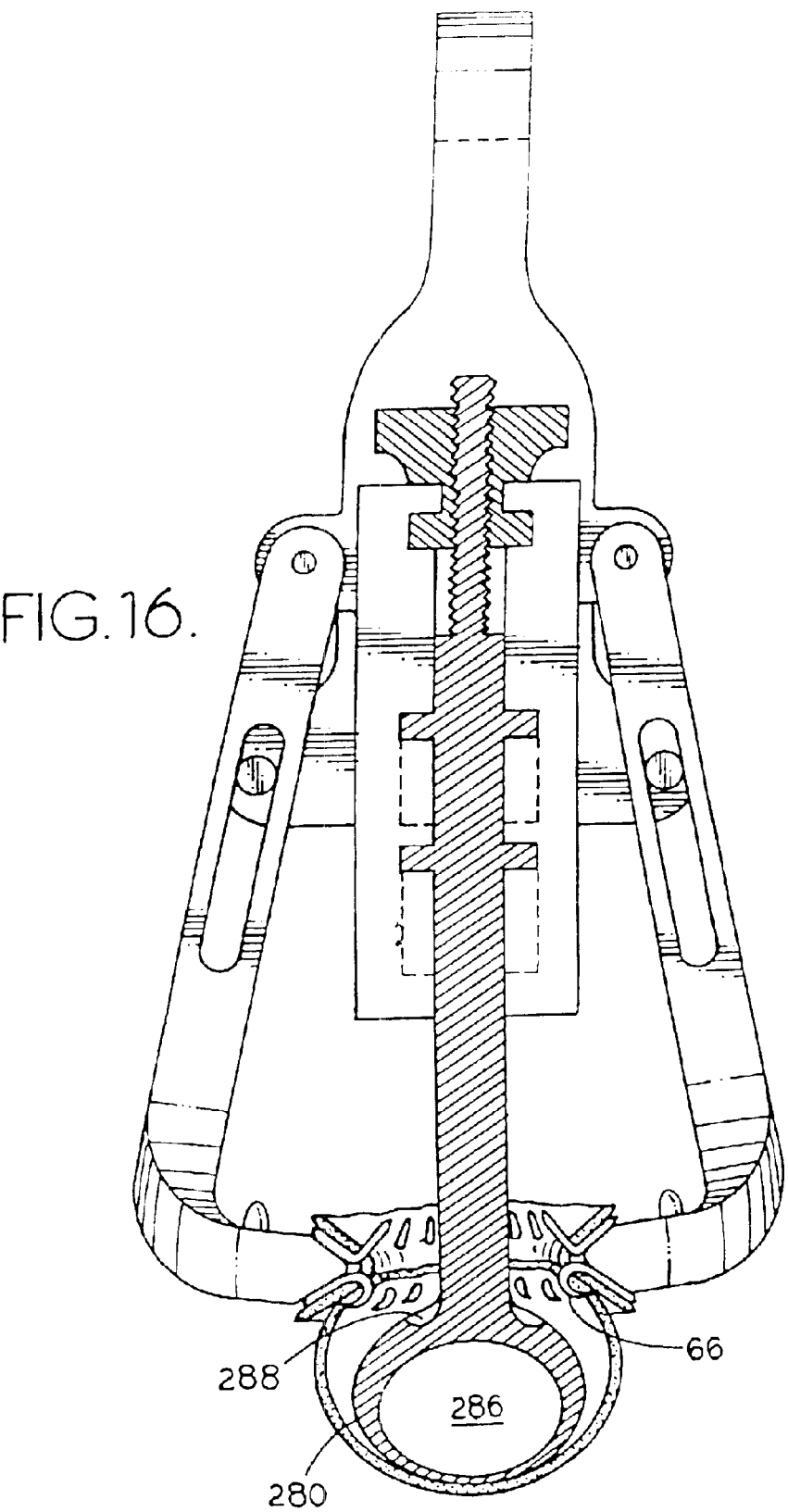
FIG. 16 is an elevational view of the FIGS. 12 and 13 tool in place after a cuff has been set onto an artery and-just prior to removing an anvil of the tool from the artery.

Artery anvil head 274 includes a bullet shaped body 280 having two ends 282 and 284 with a bypass channel 286 defined longitudinally therethrough from one end 282 to the other end 284. This channel permits blood flow through the anvil head maintaining perfusion while the cuff is being attached. A fastener turning section 288 is defined in top surface 290 of the head 274 adjacent to the intersection of the head and the body 270 and in a location to receive ends 66 of the tissue fastening pins when they are forced through the blood vessel wall. The fastener turning section is concave so the pin is turned as it engages and follows the anvil head surface adjacent to the turning section. This rotates the fastener end so the fastener is gradually bent to a curved shape, as shown in FIG. 16, for example. The tissue fastener is forced to follow this turning section by engagement of the driver head surface against the cuff and against the tissue retention pins 62 as the heads 218, 220 are moved into engagement with the cuff by operation of the finger frame 126 and as the artery anvil is moved in direction 260 by operation of the knob 247 on threaded portion 272.

Driver heads 218, 220 include docking pins 294 which releasably engage holes 80 and 90 of the docking extensions 70 and 82 on the cuff to control the shape of the cuff. The friction fit between pins 294 and the extensions 70 and 82 is great enough to permit the cuff to be pulled and shaped by movement of the driver heads, but low enough so the pins 294 can be pulled out of the docking elements without pulling the cuff off of the blood vessel. Alternatively, pins 294 could be retracted through a flexible shaft connected up to the handle. Pulling the driver heads outwardly in direction 227 will enlarge the junction and will change its shape from oblong toward circular. Therefore, a surgeon can shape the junction in the manner that is most efficient to healing and to defining an effective anastomosis.

Figure 14:
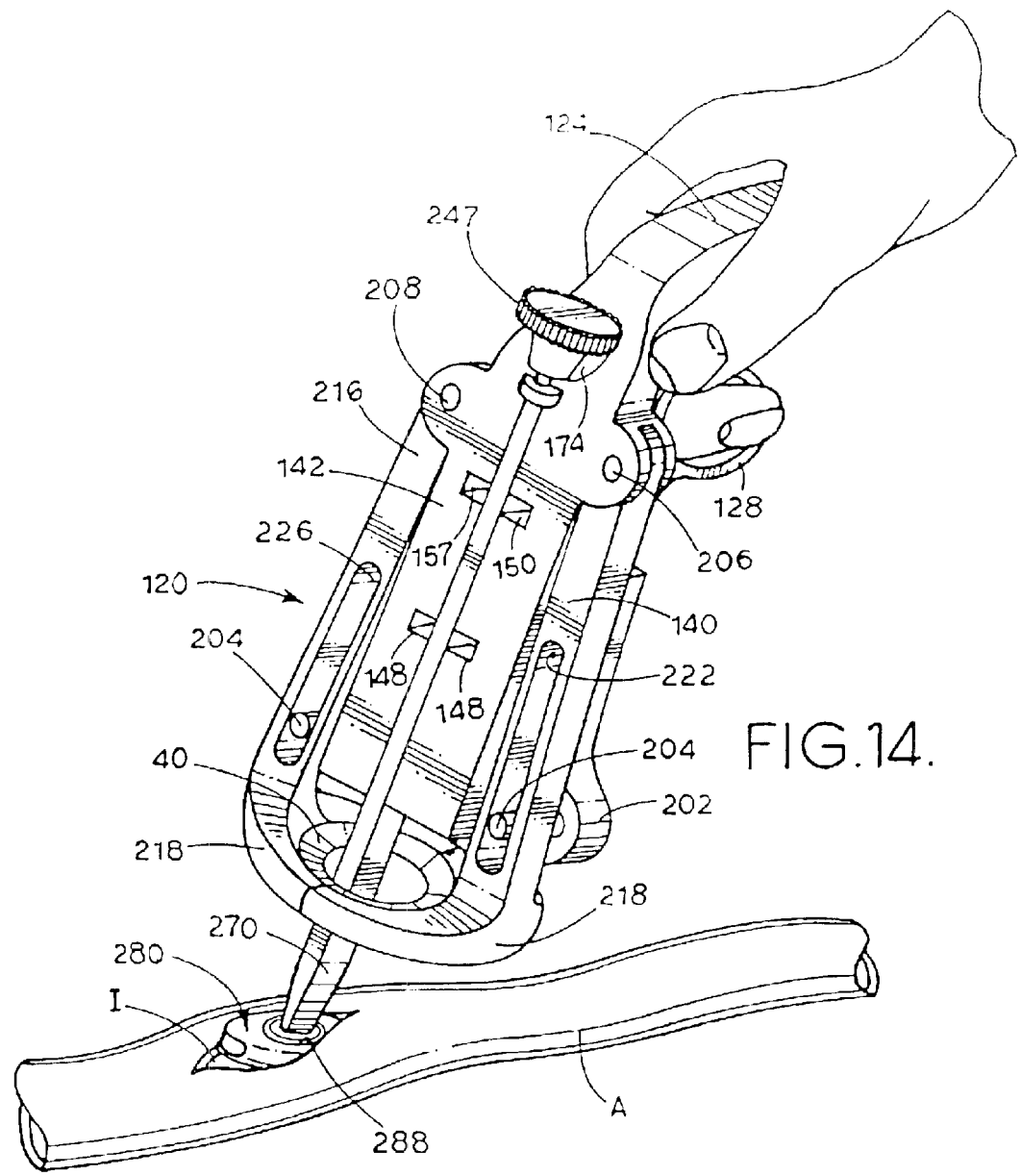
FIG. 14 is a perspective view showing the FIGS. 12 and 13 tool in use in placing a cuff on an artery.

An assembled instrument is shown in FIG. 14 with an artery anvil being inserted through an arteriotomy I in an artery A and a cuff 40 on the driver elements. As can be seen, once the incision is made, the artery anvil head is button holed into the artery via the incision. The anvil head is actually larger than the incision in the artery but can be angled through the incision into position as shown in FIG. 14. The knob 247 is operated to draw the anvil head and vessel surface at the incision up toward heads 218, 220. This action also isolates the working area from motion associated with the beating heart. As indicated in FIG. 15, after the head supported cuff contacts the outside of the artery, driver heads 218, 220 are operated to force the edges 232 against the waist section 49 and against the surfaces of the edges 236 and 238, and the knob 247 is further operated to draw the anvil and the cuff together. Further operation of the knob 247 forces the tissue fasteners through the blood vessel tissue, into turning section 288 and around on themselves in the manner of a staple whereby the cuff is fixed to the blood vessel. During this operation, blood flows through the artery via channel 286. Once the cuff is attached to the artery, the driver heads 218, 220 are opened as shown in FIG. 16 so the anvil head 274 can be removed from the artery. Since the cuff is connected to the driver heads, opening the driver heads will enlarge the incision thereby permitting the artery anvil to be removed.

The graft vessel is prepared in a similar manner. The graft anvil is inserted into the graft blood vessel via the end of that blood vessel and is tied to the graft anvil head 244 with a garroting suture. The graft anvil 134 is attached to handle frame 122. The instrument is operated to attach a cuff to the graft blood vessel in a manner similar to that just described for attaching a cuff to the artery. Actually, the graft is prepared first because the surgeon has more time to work on the graft than on the artery. The graft anvil allows the surgeon to prepare the graft on the anvil first and then attach the anvil to the instrument at a later time when it is convenient to do so.

Figure 17:
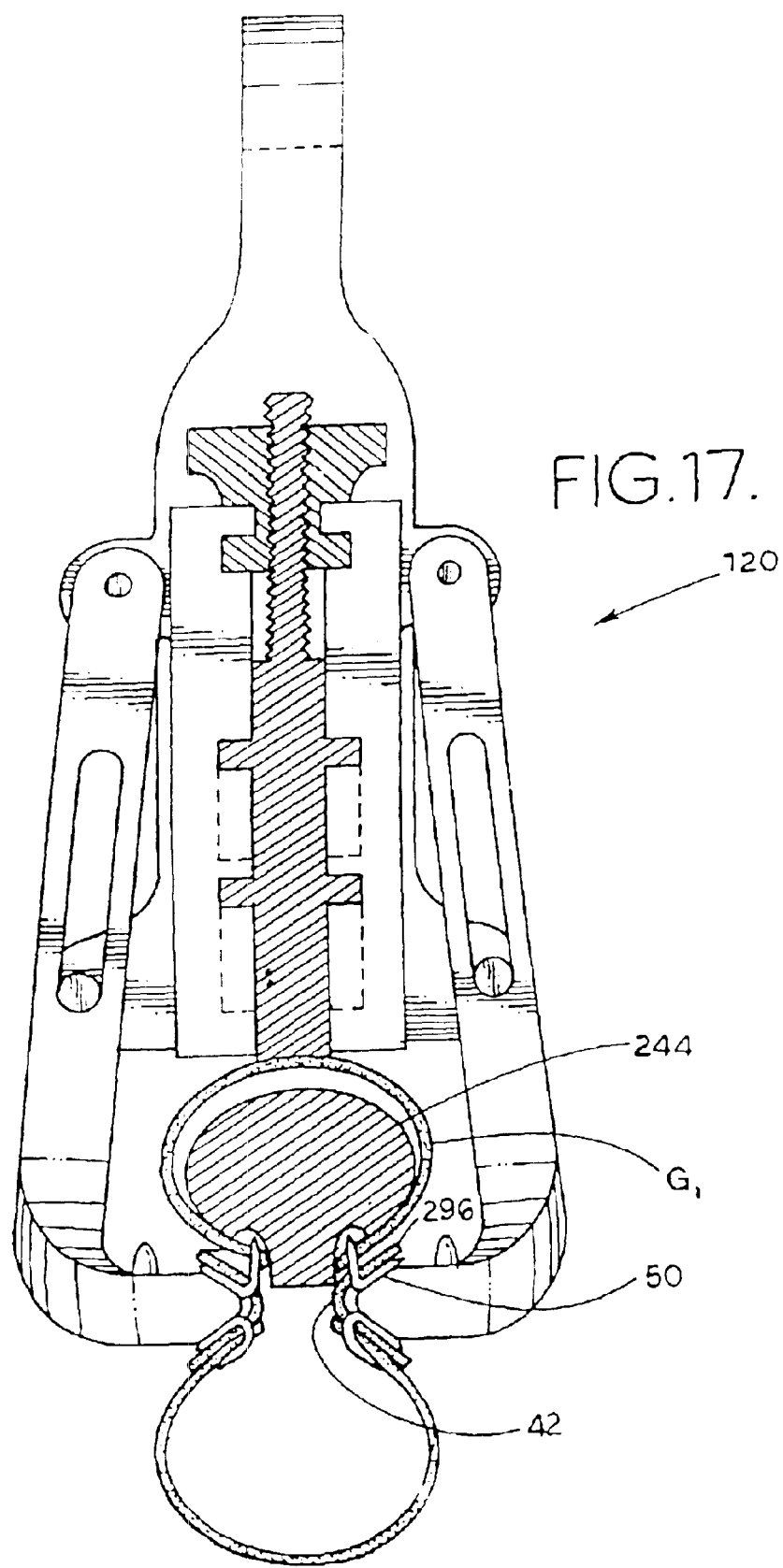
FIG. 17 is an elevational view of the FIGS. 12 and 13 tool with an anvil in place in a graft for placement of a single cuff form of the invention.

The instrument is then maneuvered so the graft blood vessel is adjacent to the cuff mounted on the artery. The knob 247 is then operated to force the graft blood vessel into contact with the cuff portion that is not attached to the artery to attach the graft vessel to the artery attached cuff. As shown in FIG. 17, the graft anvil head has a fastener turning section 296 which operates to turn the fasteners in that section of the cuff in a manner identical to the above-described turning of the fasteners in the artery. This is illustrated in FIG. 17 for a single cuff embodiment. Turning section 296 is used to turn the tissue retention pins to either attach a single cuff to the blood vessel or to attach a separate cuff to the blood vessel. Once the cuff is attached to the graft (for the single cuff embodiment), or the cuff on the graft is attached to the cuff on the artery (for the double cuff embodiment) inside edges 26 and 26' of the vessels are brought together (see FIG. 6), the driver heads 218, 220 are manipulated to enlarge the graft incision to permit the graft anvil head to be withdrawn from the graft vessel via the end of that vessel. The driver heads can then be further manipulated to size and shape the junction, and then manipulated to remove the docking extensions 70 and 82 from the docking pins 294 to release the cuff or cuffs from the instrument. The graft blood vessel is then tied off and the anastomosis is complete.

A sinusoidal shape for the joint is disclosed in the parent application (see FIG. 43 thereof). By careful and precise configuration of alignments between the two malleable ring-shaped stents and the fasteners, a leak-free joint can be formed. As the two malleable ring-shaped stents are shaped, it is important to maintain the alignment between the stents in order to create a leak-free joint. Alignment in the present invention is maintained through the use of pins and sockets which extend from the malleable stents, as discussed in the parent application. The pins and sockets not only align but also retain the two stents in compression to hold the stents securely together.

The parent application discloses both a single and a double stent for forming the joint. It is noted that a sinusoidal shape for the joint realizes the most significant benefits for the double stent embodiment.

Figure 18:
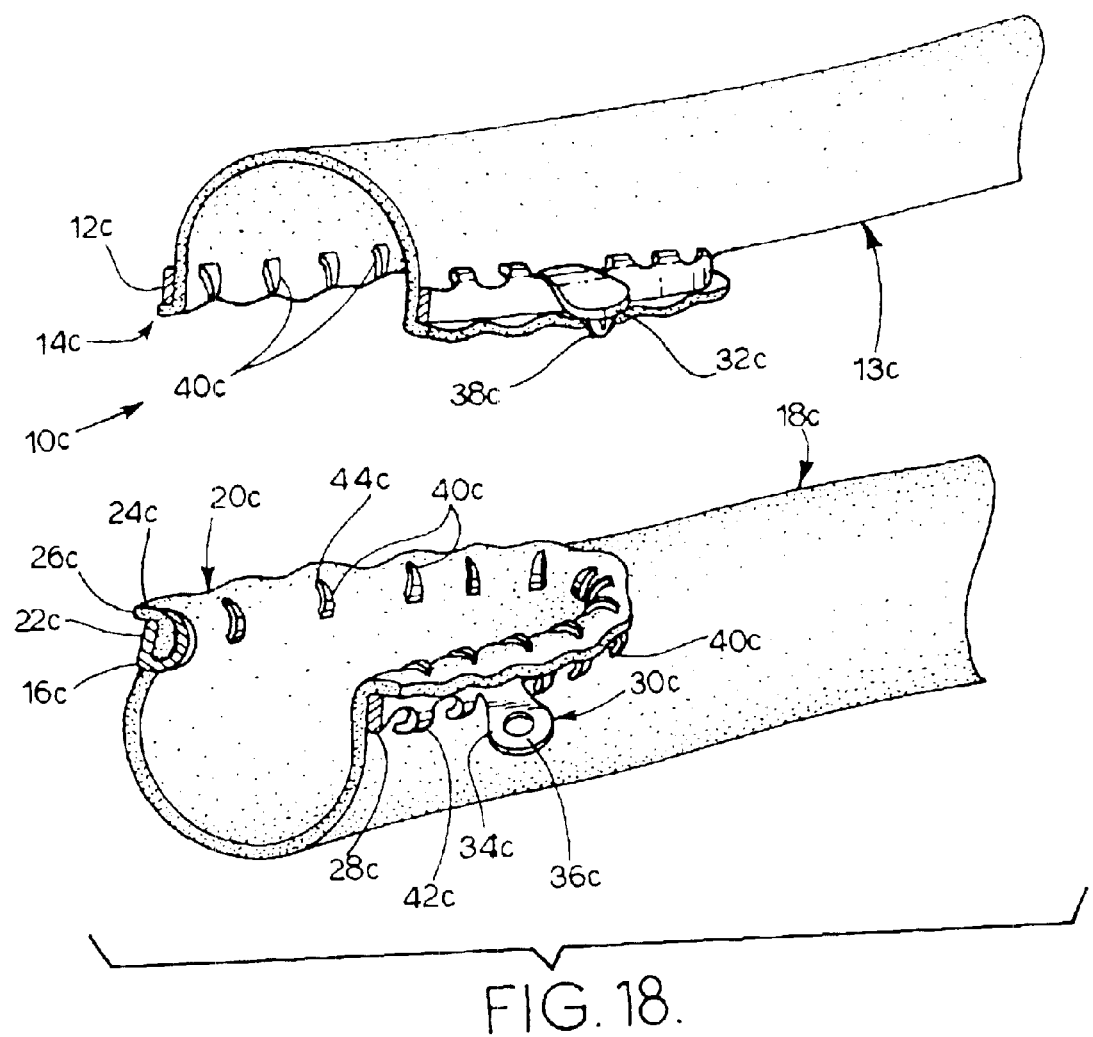
FIG. 18 is an isometric section showing a two cuff device.

Shown in FIG. 18 is a two cuff device 10C in which a first malleable ring-shaped stent 12C is mounted on a first vessel 13C adjacent to an incision 14C in the first vessel, and a second malleable ring-shaped stent 16C mounted on a second vessel 18C adjacent to an incision 20C defined in the second vessel.

The stents are identical, therefore, only one stent will be discussed. Stent 16C includes a body 22C having an inner edge 24C located closely adjacent to edge 26C of vessel 18C. Edge 26C is formed by the vessel 18C adjacent to the incision 20C. Body 22C further includes an outer edge 28C, with the body being located between the inner and the outer edges 24C and 28C.

Stent 16C also includes two coupling elements 30C and 32C (which is shown on stent 12C for ease of illustration). As shown, element 30C includes a body 34C integrally fixed to body 22C to extend beyond inner edge 26C and which has a pin-receiving hole 36C near a distal end thereof. Element 30C is flexible so it can be distorted near hole 36C and will flex and then return to the shape shown in FIG. 18. Element 32C is integrally attached to the stent body to extend past the inner edge thereof and has a locking pin 38C thereon near a distal end thereof in position to be received in hole 36C to couple the two stents together. An element 30C is on one portion of each stent and an element 32C is on another, diametrically opposite, side of the stent so the stents can be coupled together. As shown in FIG. 18, the-coupling elements lie in the same plane as the bodies of the malleable stents. Therefore, when the coupling elements are rotated, the stent bodies will correspondingly rotate. The purpose of this rotation will be understood from the following disclosure.

Referring next to FIGS. 18–21, it can be seen that each stent includes a plurality of fasteners 40C. All of the fasteners are identical, therefore, only one fastener will be described. Fastener 40C includes a proximal portion 42C integrally fixed to body 22C adjacent to outer edge 28C and a distal tip 44C. As can be seen in the figures, body 22C is located between fastener proximal portion 42C and inner edge 24C.

Figure 19:
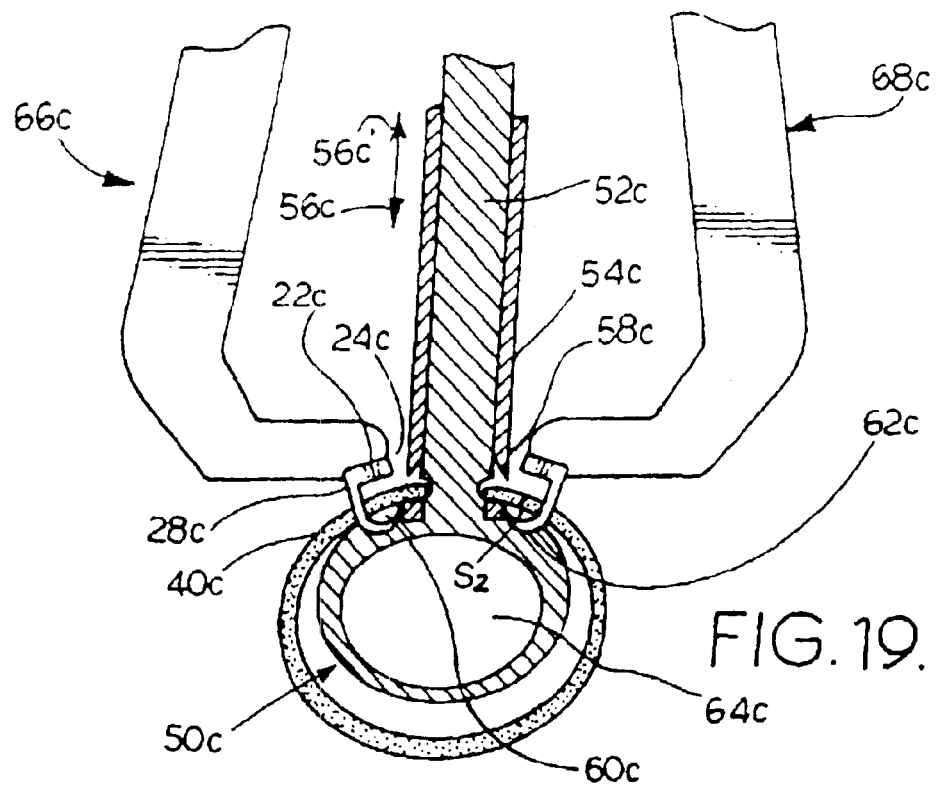
FIG. 19 is a sectional view of the FIGS. 12 and 13 tool in the process of forming the fasteners in an early step of the forming process.
Figure 20:
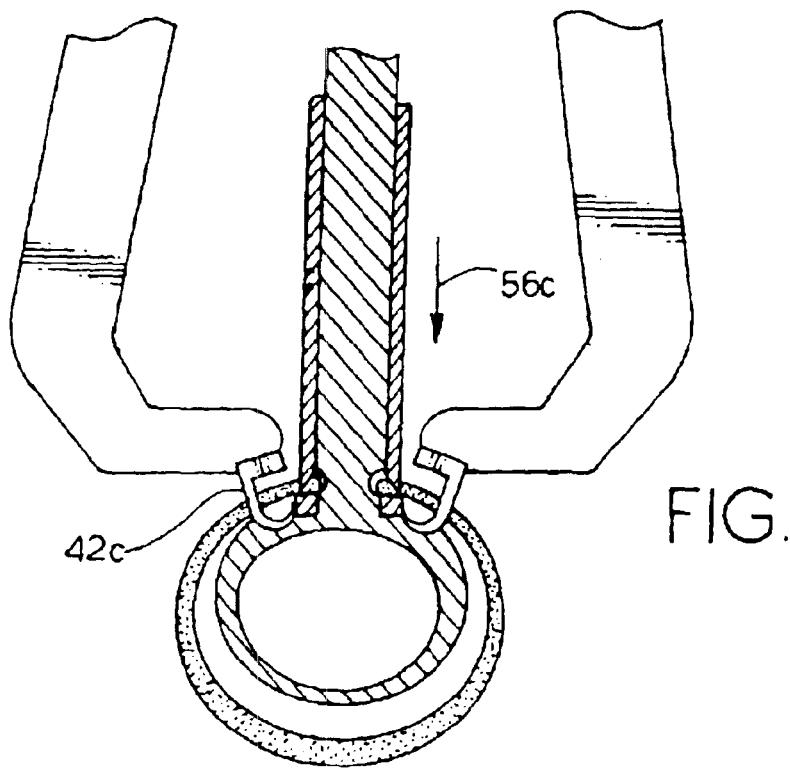
FIG. 20 is a sectional view of the FIGS. 12 and 13 tool in the process of forming the fasteners in another step of the forming process.
Figure 21:
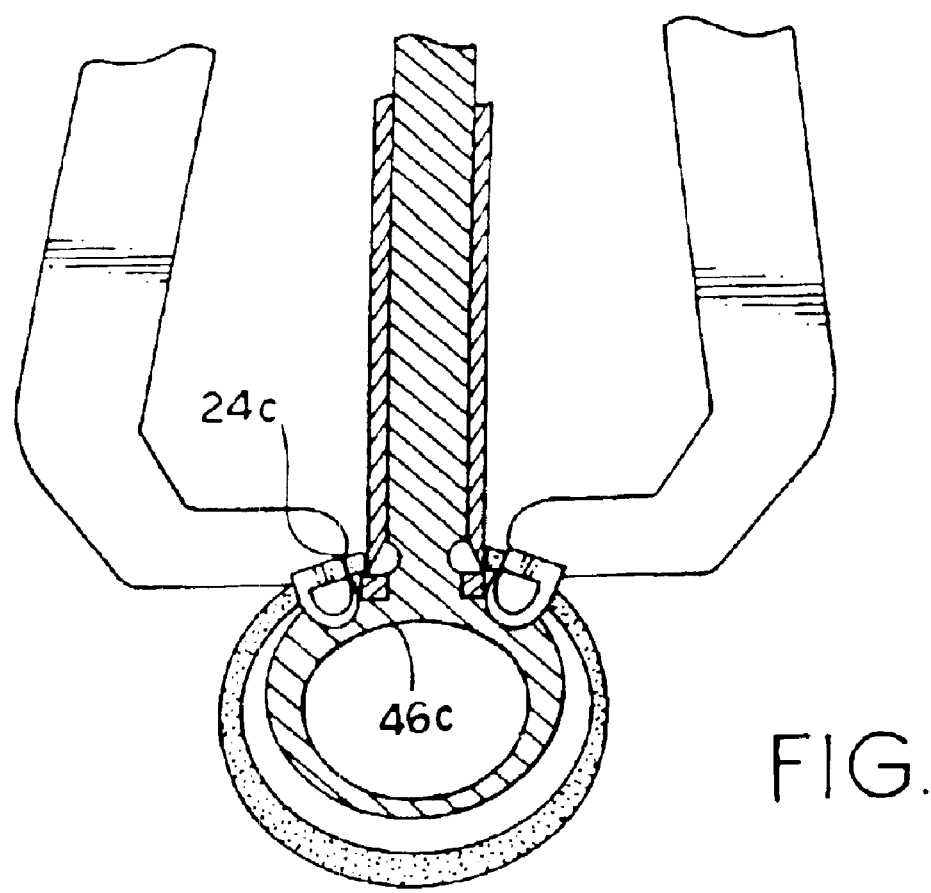
FIG. 21 is a sectional view of the FIGS. 12 and 13 tool in the process of forming the fasteners in a late step of the forming process.

When the fasteners are formed, the tip 44C is forced around and toward inner edge 24C as can be seen by comparing FIGS. 19–21. The fastener is forced through the vessel wall, around and toward inner edge 24C to mount the stents on the vessel adjacent to the incision. As can be visualized, such movement grasps the vessel wall and pulls it toward the incision. The vessel wall is thus captured and controlled during the fastener forming process thereby improving the accuracy of the joint forming process over the prior art.

As can be seen in FIG. 21, the formed fasteners have a portion 46C that extends beyond inner edge 24C. The stents can be oriented in a vertical manner (see FIG. 26) or in a horizontal manner (see FIGS. 24 and 25) after coupling. Depending on the coupled orientation of the stents, the fasteners are formed accordingly so the tip is closely adjacent to the inner edge of the body in the horizontal orientation, and somewhat spaced from the inner edge of the body in the vertical orientation. In either orientation, the vessel wall is grasped and rotated toward the incision to force the vessel wall adjacent to the incision to rotate about the outer edge of the body. This evaginates the vessel wall to expose the intima, or inner surface, of each vessel to the intima, or inner surface, of the other vessel.

Figure 24:
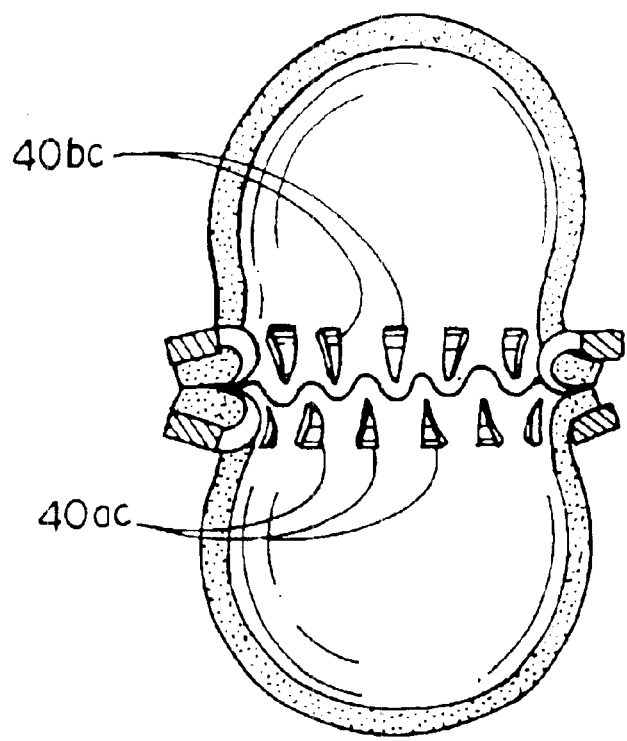
FIG. 24 is a side elevational cross-sectional view of a completed anastomosis and shows the sinusoidal form of the joint at the abutting tissue edges.

As can be seen in the figures, some portion of each fastener protrudes beyond the edge of the vessel adjacent to the incision. As can also be seen in the figures, especially FIGS. 24 and 25, fasteners on stent 12C are staggered with respect to fasteners on stent 16C. This is illustrated in FIGS. 24 and 25 by fasteners 40aC and 40bC. This staggered relationship interdigitates the fastener 40aC between the two fasteners 40bC on either side of fastener 40aC when the joint J is formed.

The interdigitation of fasteners combined with the protrusion of a portion of each fastener beyond inner edge 24C of each stent, causes the vessel wall to be deformed by the fasteners when the stents 12C and 16C are coupled together to form a joint. The deformation of the vessel walls takes the form of a sinusoidal-like shape as best shown in FIGS. 24–26. For the sake of clarity of description, a sinusoidal function is shown in FIG. 27 along an x-axis and a y-axis. The function includes lobes L1 and L3 formed by the intersection $I_1$ of the function with the x-axis. Lobe L1 will be referred to as a positive lobe, and lobe L3 will be referred to as a negative lobe. As shown, lobes L1 and L3 are adjacent to each other, and lobe L1 includes a maximum point P1 while lobe L3 has a minimum point P2.

Comparing FIGS. 26 and 27, it can be seen that the anastomosis joint J is sinusoidal in shape and includes lobes L1 and L3 formed by the vessel walls that have been deformed by the fasteners. As shown, the fasteners are located opposite to the maximum and minimum points P1 and P2 with these points being located adjacent to the tips of the fasteners.

Further, as indicated in FIG. 26, the joint includes coupling elements 30C and 32C. These elements act like compliant springs which gently press on the stent to ensure a secure clamping of the stent against the interposed tissue. The interposed tissue can act like a compliant seal as well whereby an adjustable hemostatic joint is defined. Still further, the stiffness of the joint is a function of the compliance of the malleable ring-shaped stent. Thus, by varying the thickness and dimensions, such as the width, of the stent, the stiffness of the joint can be influenced. By adjusting these same characteristics, including the length dimension, of the docking legs, the amount of pressure applied to the tissue to hold the stents together can be altered. This discussion applies to both the single cuff configuration as well as the double cuff configuration such as shown in FIG. 11.

As discussed above, the overlapping nature of the lobes of the junction seals the junction and creates a leak-free joint. It is also noted that the cross-sectional shape of the malleable ring-shaped stents is not necessarily a limiting factor in the joint configuration, and many shapes can be used without departing from the scope of the present disclosure.

It is also noted that the stents and coupling means could be injection molded from a plastic polymer and the fastener legs could be made from wire. In this manner, the fasteners would be captured on the polymer base. The polymer base could also be made of an absorbable materials such as that used in absorbable sutures. In addition, a single wire loop could be embedded into the polymer in order to make it retain its shape when it is opened to allow removal of the anvil from the vessel. Once the polymer is absorbed, the wire ring and fasteners will remain on the outside of the vessel. This will not cause a problem since the tissue will have healed by that time.

FIG. 27A shows a histology cross section of the healing process of an anastomotic joint that has been prepared by those who are skilled in the art of pathology. This is a standard means for a pathologist to study tissue at the cellular level. Tines 100F are from the proximal side or the graft side. Tines 101F are from the distal side or the artery side. FIG. 27B is a magnified view from the central area of FIG. 27A. This shows the metal tines 100F and 101F associated with an interposed sinusoidal zone 103F of reparative tissue 104F. This tissue is composed primarily of a solid ingrowth of dense fibrous tissue. There is minimal evidence of old hemorrhage.

Method

The method of forming joint J is discussed in the parent application with respect to FIGS. 41–42B thereof. Accordingly, the details of placing the anvils, button-holing the artery anvils, and the like will not be presented here, but reference is made to the just-mentioned disclosure in the parent application. The details of the method steps used to form the particular fasteners 40C and the formation of joint J will be presented.

After an incision has been made in the vessel, an anvil 50C is button-holed into the vessel as indicated in FIG. 19. The anvil has a stem 52C which extends out of the patient. A cutter 54C is associated with the anvil to move in directions 56C and 56C' by operation of an appropriate handle located outside the patient. Cutter 54C includes a cutting edge 58C located near anvil pocket 60C. Anvil pocket 60C is concave and a second concave cutout portion 62C is located at the intersection of the anvil body and the anvil stem. The anvil body also includes a flow passage 64C as discussed in the parent application so blood can continue to flow in the vessel during the procedure.

Stent controlling jaws 66C and 68C have ring-shaped stents seats on a distal end thereof to releasably mount ring-shaped stents 12C and 16C thereon.

In FIG. 19, the stents with the fasteners are shown on the jaws. The anvil has been inserted into the lumen of the vessel. The anvil is first pulled up against the fastener legs which causes the legs to penetrate the vessel and the wall and begin to turn in the anvil pockets. This is the first important step in controlling the edges of the tissue. By setting the fastener legs into the vessel wall first, the edges of the tissue are captured so they cannot move out from beneath the cutter during the trimming process.

In FIG. 20, the cutter is progressing downward and is trimming off any excess tissue at the edges. The fastener legs, however, are still penetrating the vessel wall and holding it in place while the cutter is trimming.

In FIG. 21, the anvils and the jaws have completed the forming of the fastener which turns the fastener legs inward toward the incision. This captures the edge of the vessel wall securely and rotates it up toward the inside edge of the malleable ring-shaped stents.

In FIG. 22, the malleable ring-shaped stent is shown as it would appear in the last stage of crimping before being opened to allow the anvil to be removed. As shown in FIG. 22, the malleable stent is on the outside. The fastener legs have penetrated from the outside edges of the ring-shaped stents and have gone through the vessel wall and have come up forward toward the incision thus bringing the vessel wall out toward the opening shown in the center.

FIG. 23 shows the malleable ring-shaped stent being stretched to allow exit of the anvil and to increase the cross sectional flow area. This is the final stage before the two stents are joined to make a complete anastomosis.

It is also noted that the stents can be joined together using a tool such as disclosed in the parent application in FIGS. 38–40. Furthermore, the tool used to operate the anvil will not be discussed, since the tool per se does not form a portion of this invention. It is only noted that such a tool needs only to include some form of handle to move the anvil in the manner discussed above, and to move the cutter in relation to the anvil to perform the cutting function discussed above. Suitable handles are known to those skilled in the art from disclosures such as the parent disclosures.

As discussed above, proper and accurate alignment of the elements associated with the anastomosis is difficult, but necessary. In view of the above, the present invention includes apparatus and methods for properly and accurately guiding and aligning the elements.

In cardiovascular surgery, surgeons are very familiar with the placement of sutures between the annulus of a heart valve and a prosthesis. The *Illustrated Handbook of Cardiac Surgery* by Harlan, Starr and Harwin describes this common method of attachment of valves. The method described includes first placing sutures in the heart tissue, spacing them accordingly, then setting the sutures into the prosthesis at the same spacing. The valve can then be guided into place in the annulus by sliding it down the taut sutures to seat in the aortic root. Therefore, a surgeon may be familiar with a procedure which utilizes guide sutures to align and dock one element to another. The invention herein takes advantage of this and applies it to the anastomosis procedure. Accordingly, as shown in FIGS. 28–30C, guide sutures 400 are anchored at tab 401 to a target stent 402 which can be either the proximal stent on the aorta or the distal stent on the coronary artery. There are pass-through holes 404 in the stent 406 attached to the graft. The pass-through holes 404 allow stent 406 to ride on the suture guides 400 to find its place in perfect alignment when it comes into contact with the target stent 402. This removes the requirement of fine motor control and visual access when joining stents.

The docking portion of the procedure can be very difficult due to the small size of the artery, the graft vessel and the stents. Tool 410 permits remotely controlled proper docking to place the malleable stents together in the correct configuration and a means to join the two malleable stents together assuring a leak-free anastomosis.

Stent docking and guide tool 410 is shown in FIG. 28 and is used to manipulate the vessels in remote, limited access surgery. The tool is used to guide the ends of the graft without unnecessary manipulation of the graft tissue and also facilitates the final attachment of a clamping or locking means between the two stents to permanently hold them together in approximation.

Tool 410 places the malleable stents together and includes a long shafted handle 412 having a hand grip 414 on one end and a nest 416 on the distal end to accept the malleable stent and a mechanism operably connecting a trigger in the hand grip to the nest to release the stent from the nest when the surgeon operates the trigger once it has been attached to the artery or graft. When the surgeon is ready to place the malleable stents together the first step is to load the malleable stent, on the graft vessel, in the distal end of the docking guide tool. The surgeon will place the stent into the distal end of the tool while he is depressing the trigger on the handle at the proximal end of the docking guide tool. This malleable stent will lock into the docking guide tool. The surgeon will now guide the graft down onto the artery stent by using the guide sutures that are attached to the artery malleable stent. The sutures are also run through the graft stent or guided through the docking tool. A parachuting technique will be used to bring the two stents together. It is extremely important that the docking guide tool be small enough at the distal end for the surgeon to see when the stents have been mated. Once the stents are together the surgeon must attach the stents together. On the malleable stents there are four docking legs. These will be used to hold the malleable stents together forming a leak-free anastomosis. While the surgeon is holding the graft stent against the artery stent, a docking tool will be used to attach the stents. The docking tool is a long narrow tool that will join the stent legs. In one embodiment the docking guide tool will deploy a small O-ring that will slide over the docking legs on the malleable stents thereby locking the stents together. Once the surgeon has placed an O-ring on all four docking legs the stents are permanently attached to each other. The legs have anti-backup features to prevent the O-ring from coming off the leg. The surgeon will now depress the trigger on the proximal end of the docking tool and the malleable stent will be released from the docking tool. Once the docking tool is removed the surgeon is free to cut the guide sutures from the anastomosis. This process will be repeated for the other anastomosis.

The process of docking two stents using guide sutures 400 is illustrated in FIGS. 28 and 35B–35E. Target stent 402 has pre-tied sutures 400 anchored thereto by pre-tied knots 420 attached to tabs on the stent, such as eyelets 78 and/or 88 shown in FIG. 4A, with the stent being attached to an artery. Sutures 400 extend away from target stent 402 and extend through holes 404 in tabs 405 of stent 406. Stent 406 with the graft vessel attached thereto is slid down the sutures into contact with target stent 402. The stents automatically align with each other as indicated in FIGS. 35D and 35F due to the guide sutures.

Once the surgeon has placed the malleable stents on the graft vessel and the artery, as mentioned previously, the next step is to attach the two malleable stents together forming a leak-free anastomosis. FIGS. 44, 45 and 28 show malleable stent 406 attached to the graft vessel G$_1$. The surgeon will place docking guide tool 410 over stent 406 while depressing trigger 666 in direction 667 on the proximal end of the docking guide tool. FIG. 45 shows a bottom view of the distal end of docking guide tool 410. By depressing trigger 666 (see FIG. 28) in direction 667, leg retention bars 668 are retracted, allowing docking legs 669 to seat within nest 416 of docking guide tool 410. Once malleable stent 406 is seated within nest 416, the surgeon will release trigger 666 thereby allowing leg retention bars 668 to close and trap malleable stent 406 within docking guide tool 410. FIG. 28 shows malleable stent 406, attached to docking guide tool 410. The surgeon will now slide malleable stent 406 mounted in the graft vessel onto target stent 402 mounted on the coronary artery by applying tension to the guide sutures 400. Once the stents have made contact and are seated together the docking tool will be used to permanently join the stents together.

FIG. 46 shows a docking tool 672 for remotely docking stents together. The proximal end of docking tool 672 has a flexible collar 673 that rides over a flexible core shaft 674. Docking tool 672 is flexible thereby allowing the surgeon to deform the shaft to gain access to the joined docking legs of the malleable stents. The surgeon will load O-ring 675 onto flexible core shaft 674 at the distal end of docking tool 672.

FIG. 47 shows once O-ring 675 is fully seated at the distal end of docking tool collar 673 the surgeon will place countersink tip 676 of flexible core shaft 674 on the joined ends of the docking legs 677. The joined ends of docking legs 677 will be nested into countersink 676 of flexible core shaft 674. At this point, the surgeon will be able feel the docking tool is attached to docking legs 677 and he will slide flexible collar 673 in direction 678 displacing O-ring 675 from flexible core shaft 674 onto the joined ends of docking legs 677. O-ring 675 will ride over retention bumps 679 integral with docking legs 677 and be seated. This process will be repeated until all four legs of the malleable stents are joined. Once the surgeon has validated the anastomosis is leak-free he can now cut guide sutures 400 as shown at suture cut 680 in FIG. 48.

The following will show many different ways to join malleable ring-shaped stents together by deforming one or both docking legs. FIGS. 49 to 50C show another way to attach the docking legs together. The malleable stents attached to the graft vessel have two legs 681 that are perpendicular to the docking legs. Legs 681 will be formed around the docking leg 682 of a mating malleable stent. After the docking guide tool has placed the malleable stents together, a crimping tool 683 is placed at the end of the docking leg. An anvil 684 will hold the docking legs together while a sliding tube 685 will cam jaws 686 together forming legs 681 around the body of docking leg 682 as shown in FIGS. 50A–50C.

Once the two stents are in proper alignment with each other, they are clamped together. While various means can be used to clamp the aligned stents together, the preferred clamp is shown in FIG. 35E as clamp 422 which is slid down each suture 400 into contact with the aligned stents. Clamp 422 is a spring clamp which is biased into a closed configuration and is held open as it is moved by a tool along the suture and into the FIG. 35E position. Clamp 422 has two suture engaging jaws 424 which, when released, securely engage the suture to hold the clamp in position. The combination of clamp 422 and knot 420 maintain the stents 402 and 406 in a locked condition.

While clamp 422 is shown, other elements can be used to hold the two stents together. As shown in FIGS. 38A–42B, various clamp elements can also be used without departing from the teaching and scope of this disclosure. Thus, the clamp can include a corrugated body 426 as shown in FIGS. 38A–38C for clamp 422' which includes opposed cutting edge 428 and shear edge 429 that overlap each other in the manner of a scissor joint adjacent to a top bend 430 that orients the cutting edges in a cutting position to snip suture 400 as indicated in FIG. 38C. Other bends in body 426 serve to adjust the spring tension of the body.

Clamp 422''' is shown in FIG. 39 in an unfolded form as including a body 426' having a suture hole 432 as well as cooperating cross-over cutouts 434 and 436, cutting edge 428' and shear edge 429'. The in place clamp 422'' is shown in FIG. 40. An alternative form of the cutting edge is shown at 428'' for clamp 422'' illustrated in FIG. 41 with a shear edge 429'' cooperating therewith.

Yet another form of the clamp is shown in FIGS. 42A and 42B as cross-leg clamp 422'''. Clamp 422''' is positioned on the outside of stent tabs 401 and 406'. Clamp 422''' is in the nature of an alligator clamp with jaws 440 and 442 engaging tabs 401 and 406' as shown in FIG. 42B to exert pressure on those tabs as indicated in FIG. 42B by arrows 444. Suture 400 extends through clamp 422''' via a suture guide hole 446.

A suture chock 448 can be positioned on the suture adjacent to the clamp to hold the clamp in place as shown in FIGS. 35F and 42B. Chock 448 includes a spring element 449 to enhance the friction fit between chock 448 and the suture.

Other variations of the docking elements are illustrated in FIGS. 43A–43J. Referring to FIG. 43A, tab TC on one stent includes two legs which diverge radially outward from the body of the stent to form a V-notch into which a projection PC on the other stent is received for aligning the two stents to form a lock LC. The lock LC is self-orienting since projection PC will be guided into place by the legs on tab TC. Once projection PC is in place in the V-notch, it can be bent over the tab TC to twist and lock the two stents together.

Yet another means for locking the two stents together is shown in FIG. 43B as including a tab AC on one stent and a tab BC on the other stent. The tabs AC and BC have off-set edges AC1 and BC1 that interengage when the tabs are aligned and brought together.

A snap fit is shown in FIG. 43C in which a tab CC is on a first stent and extends radially outward therefrom. A second tab DC is on the other stent and has a clamping slot defined therein for accommodating tab CC to form a locked joint LC'. When tab CC is properly aligned with tab DC, tab CC will be received in the clamping slot as shown in FIG. 43C to properly align the two stents with regard to each other so the fasteners, indicated by reference indicators F1 and F2 in FIG. 43C, are interdigitated as discussed above to define the sinusoidal joint of the present invention. Tab CC also includes a slot CC1 to enhance the flexibility of the tab so it can move into and out of the slot in tab DC yet will be securely held therein.

Yet another variation of the locked joint between the two aligned stents is shown in FIG. 43D as joint LC''. Joint LC'' also aligns fasteners F1 and F2 to be interdigitated when the two stents are locked together and includes a tab DC' on one stent and a tab EC on the other stent. Tab DC' includes a slot DCS having a lead in area defined by converging edges on legs DCL and a receiving slot DCR adjacent to the edges on legs DCL. A spring leg ECL is located to move through the lead in area of slot DCS as indicated in FIG. 43E and to engage tab DC' when it is accommodated in area DCR to lock tab EC to tab DC' as indicated in FIG. 43F. FIGS. 43L–43M illustrate tab DC'' and DC''' which are secured by twisting extensions DC'''' and tab DC'' around the tab DC''' to join two malleable mounting structures together.

Still another way to join the malleable stents together is shown in FIGS. 43G and 43H. Malleable stent $R_A$ is attached to the artery and has protruding posts PP. The malleable stent $R_A$ is attached to a stent $R_G$ on the graft vessel. Stent $R_G$ has a cutout CF formed with interfering tabs CFT. When the two malleable stents $R_A$ and $R_G$ are brought together cutout CF is forced over protruding posts PP causing interfering tabs CFT to bind thereby holding malleable stents $R_A$ and $R_G$ together. FIG. 43I shows a protruding post P' with directional barbs DB attached thereto. FIG. 43J shows a protruding post P'' with a single detent SD. FIG. 43K shows a protruding post P''' with multiple detents MD. The post P', P'' and P''' may be used in place of the posts PP.

It is also noted that the docking elements, such as tabs 401 and 405 shown in FIGS. 35B and 35C of the malleable mounting structures can be magnetized to ensure proper alignment and docking. Also, rivets, similar to posts PP, can be used to attach to mounting structures together.

Cassette Loaded Firing Tool

A compact cassette loaded firing tool 450 for placing the stents is shown in FIGS. 29A, 29B, 29C, 29D and 30. Tool 450 is used in connection with cassettes 452 and 454 which are respectively associated with artery stent 402 and graft stent 406 (see FIG. 36B). The cassettes 452 and 454 are of the same construction. The following description of cassette 452 applies equally to cassette 454. Each cassette includes an anvil stem 456 having an attaching prong 458 on one end and an anvil 460 on the other end. A housing 461 slidably receives the stem 456 and provides a stent supporting platform 462 between the anvil and attaching prong. An annular cutter assembly ring 463 is slidably received in the housing 461 and has radially extending blades 464 disposed to opposite sides of the stem 456 for extension from the distal end of the housing 461. An annular driver 465 is slidably received within the cutter assembly for extension from the assembly by the stem receiver 471b.

Tool 450 includes an operating handle 470 on one end of a tubular body 472 with the cassettes being releasably mounted on the end 474 of the body. The proximal end of the body is formed with a first transverse finger grip 484a. An attaching groove 471 on prong 458 releasably receives a stem lock 471a (see FIG. 29C) on stem receiver 471b to releasably hold cassettes 452, 454 on tool 450. The stem lock 471a is operably connected to a release button CRB on tool 450. When button CRB is depressed the stem lock 471a is withdrawn from groove 471 thereby releasing cassette 452 from the tool. The cassette can then be removed from the surgical site by hand or the like. The cassette is disposable, and the instrument itself can also be disposable, if desired. Otherwise, the instrument can be re-usable if suitable.

The stem receiver 471b is slidably received in a tubular spreader bar carrier 630 which, in turn, is slidably received in the body 472. The proximal end of the spreader bar carrier 630 terminates in a thumb ring 486a. A second transverse finger grip 484b is fixed to the proximal end of the stem receiver 471b and extends through aligned slots 630a and 472a, respectively, therefore in the carrier 630 and body 472. A first compression spring 471c is received between the stem receiver 471b and the proximal end of the spreader bar carrier 630 to normally urge a second finger grip 484b and thumb ring 486a apart. A second compression spring 484c is received between the first and second finger grips 484a and 484b to normally urge these grips apart. Spreader bars 640 are pivotally received to the spreader bar carrier 630 and extend therefrom through the distal end of the body 472 and to opposite sides of a cassette received thereon. The spreader bars 640 are for purposes of spreading a ring-shaped stent after it has been crimped into place. Their structure and operation will be described in detail with respect to FIGS. 34A and 34B.

The distal end of the spreader bar carrier 630 is proportioned to slidably receive the cutter assembly ring 463 and is formed with a shoulder 631 for abutting engagement with the ring. Upon advancement of the carrier 630, such engagement serves to extend the blades 464. The distal end of the stem receiver 471b is proportion to slidably extend through the ring 463 into abutting contact with the driver 465 to extend the driver.

In operation, the anvil 460 is first button holed into a vessel to which the stent is to be attached. The second finger grip 484b is then pulled toward the thumb ring 486a to retract the stem receiver and cinch the fastener tines of the stent to the vessel. The end of this stroke extends the driver 465 and activates the vessel cutting blades 464 to properly size the arteriotomy and free the edges of the vessel wall for proper tissue eversion. The finger grip 484b is then released and the thumb ring 486a is depressed relative to the first finger grip 484a to advance the spreader bar carrier 630 relative to the body 472 and activate the spreader bars 640 to spread the stent. (This mechanism is seen and described with respect to FIGS. 33, 34 and 35.)

After the stent is spread, the stent and anvil are released from the cassette and the anvil is removed from the cassette and button-holed out of the arteriotomy. The cassette is then removed from the tool and a new cassette is loaded into the tool in its place. Thus, the tool is again conditioned for the placing another stent.

The operation is repeated on the other vessel. The two vessels are brought together using the sutures 400 or the other docking means described above to orient the stents in the proper position relative to each other with the fasteners interdigitated, and then clamped together.

The following is a brief description of the sequence of events necessary to load and fire the compact firing tool.

The cassette 452 is loaded into the compact firing tool.

The groove 471 of the anvil stem is engaged by the stem lock 471a.

A small incision is made in the artery.

The anvil is placed into the small incision in the artery.

The anvil is centered within the small incision.

The tines puncture the artery wall and are formed on the anvil during the initial firing.

The integral knife extends the incision within the perimeter of the stent to the correct size and precisely locates and opens the incision to the correct size based on malleable stent size.

The knife is retracted within the compact firing tool.

The malleable stent is spread open to the correct size.

The malleable stent is released from the compact firing tool.

The anvil is released from the compact firing tool.

The anvil is removed from the incision in the artery.

After the disposable loading cassette has been loaded on the compact firing tool, the surgeon will attach the malleable stent to the bypass graft. The end of the graft will be prepared as the firing tool is positioned to attach the malleable stent. The compact size of the firing tool allows the surgeon the visual access needed to place the stent on the graft or artery. Once the surgeon has determined the location of the malleable stent, the anvil of the firing tool must be placed into the lumen of vessel through a small incision known as an arteriotomy. The anvil must be seated within the arteriotomy without bunching or tearing tissue. It is also important that the vessel wall is not stretched too tight on the anvil or it will cause the vessel wall to tear. Placing the anvil in the vessel will be done in a technique similar to placing a large button through a slit, by placing the button on edge and slipping it through the slit. Now the anvil is on the inside of the lumen and the malleable stent is fixated in the firing tool on the outside of the vessel. The surgeon will now activate the firing tool and the stent will move towards the anvil. Once the tines of the malleable stent penetrate the vessel wall, they will make contact with the pockets located in the anvil. At this moment the tines will start to deform and roll back inside the vessel, towards the firing tool.

The tool should be small enough to be operated with one hand and with some type of feedback on when the stent has begun to fire and when the firing sequence has been completed. The tool should also be versatile enough to be placed on any location on the surface of the heart that is currently accessible today in a traditional procedure.

During this firing series several important steps have occurred. First, the surgeon started the initial firing operation, locking the tissue and the stent. When producing a device as small as required in this application, many design issues are not readily apparent. For instance, the need to make the tines very thin and sharp to prevent leaks. Being so thin it makes them too fragile to drive into tissue in an unsupported manner. Therefore the tines must be shrouded to protect the sharp tips from being damaged and fully supported during firing to prevent unwanted buckling. The tines of the stent must be fully supported throughout the entire firing sequence. If not, they will buckle and form an undesirable non-functional ring. Even when the distal tips of the tines have penetrated the vessel wall and made contact with the anvil, the proximal ends of the tines are fully supported with a tine backing plate. The manner in which the tines are formed is a tightly controlled buckle. Second, the driver 465 has made contact with the tip of the deformed tine bending them back over thereby locking on the tissue. When this occurs the tissue is not crushed due to the nature of the tine deformation on the secondary anvil. When the driver 465 is deployed, the cutter blades 464 are also deployed to make a precise opening within the perimeter of the stent that creates the opening through which the blood will flow. The size of the opening is based on the malleable stent size. It is important to size this correctly to avoid tearing of the tissue upon stretching the stent. If too large, there will not be enough wall area from the edge of the opening to the edge of the tine. This may cause the vessel to tear inducing a leak under the stent.

The next step the tool will perform is to spread the malleable stent to the predetermined opening size. The malleable stent is placed onto the vessel in a smaller configuration and when deployed it is opened up to the correct size. The device opens the malleable stent by pulling open the docking legs that are located on the outside of the ring-shaped body of the stent. The opening must match the adjoining malleable stent on the arterial side, if they are not the same size a leak will develop between the stents. The tool assures that the surgeon the malleable ring of the stent is spread to the correct shape and size. Once the stent has been spread to the correct size, the compact firing tool will release the docking legs thereby releasing the malleable stent. The anvil will be released from the compact firing tool and the surgeon will retrieve the anvil from the arteriotomy thereupon completing the firing operation.

As shown in FIG. 36B, the surgeon would choose the correct disposable cassette to be loaded in the compact firing tool. The proximal set would include aorta cassette 478 and proximal graft cassette 479. Attached to the proximal graft cassette are guide sutures 400' to be used in the docking procedure. The distal set includes artery cassette 452 and distal graft cassette 454 (see FIG. 36A). Attached to distal artery cassette 452 are guide sutures 400". Each cassette will have a receptacle end 480 that will be inserted into cassette port 480*a* (see FIG. 29B) at the distal end of compact firing tool 450. Once the ring-shaped malleable stent is installed onto compact firing tool 450, it is ready to be implanted into the patient. The anvil is placed into the distal end of the compact firing tool. FIG. 29A shows that once cassette 454 and the anvil are attached to the compact firing tool, it is ready to be placed in the graft vessel. The surgeon ties off the end of the graft vessel with a suture 481 and then makes an arteriotomy 482 in the graft vessel. Anvil 460 of firing tool 450 is slid through arteriotomy 482 and positioned centrally within arteriotomy 482. Now the surgeon is ready to fire compact firing tool 450 by placing his fingers 483 around transverse finger grip 484*b* on the proximal end of firing tool 450, and placing his thumb 485 through the thumb ring 486*a* also located on the proximal end of the firing tool.

Directly Loaded Firing Tool

A modified directly loaded compact firing tool 450' and a cartridge 466 for loading this tool are shown in FIGS. 31, 32B, 33A, 33B and 33C. The tool 450' corresponds to the tool 450, except that it is constructed to have the stent loaded directly onto a support platform 462' formed on the distal end of the tool, rather than to support the stent through means of a cassette. Elements of the tool 450' corresponding to those of the tool 450 are designated by like numerals, followed by a prime (') sign, as follows: stem 456'; prong 458'; anvil 460'; platform 462'; cutter assembly ring 463'; blades 464'; operating handle 470'; attaching groove 471'; stem lock 471*a*'; stem receiver 471*b*'; slot 472*a*'; distal end 474'; first transverse finger grip 484*a*'; second transverse finger grip 484*b*'; plunger 486'; thumb ring 486*a*'; spreader bar carrier 630'; slot 630*a*'; shoulder 631'; and spreader bar 640'. All of these elements operate in generally the same way as the corresponding elements of the tool 450; the only difference being that no removable cassette and associated cassette release structure is provided in the tool 450'. Anvil release remains the same.

FIGS. 32A and 32B show a disposable cartridge 466 for loading the ring-shaped stents onto the platform 462' of the compact firing tool 450'. The cartridge holds the stent 476 for mounting onto the platform and shields the very long, sharp and fragile tines of the stent 476 from any contact which would distort the tines from their proper form. It comprises a generally cylindrical body 467 having longitudinal slots 468 which are proportioned for receipt of the spreader bars 640' when the cartridge is used to place a stent on the tool 450'. Release levers 469 are pivotally secured to opposite sides of the body 467 for movement between a closed condition supporting a stent 476 anvil therebetween (see FIG. 32B and FIGS. 33A and 33B) and an open condition (see FIG. 33C) releasing the stent for support on the platform 462'. The opposed interior surfaces of the levers 469 are formed with a annular groove 469*a* to support a stent therebetween when the levers are in the closed condition (see FIG. 32B). In this condition, the levers also support the stem 456' and anvil 460'. Tabs 469*b* on the tops of the levers 469 hold the anvil 460' when the levers are in this closed condition. An elastic band 469*c* extends around the levers 469 to normally bias the levers to the closed condition. Finger grips 469*d* are formed on the distal ends of the levers to enable the levers to be moved to the open condition against the bias of the band.

It should be understood that the disposable cartridge 466 is preloaded with the stent 476 prior to being delivered to the surgeon. Such preloading will be carried out in the course of manufacturing and preparing the cartridge for use. An insertion jig (not illustrated) will be used to place the stent in the cartridge during this process. The cartridge will be delivered to the surgeon in a loaded sterile condition.

FIG. 33A shows the disposable loading cartridge 466 as it is being directed into place over the distal end of the tool 450'. FIG. 33B shows the cartridge fully engaged over the end of the tool with the stem 456' of the anvil engaged in the stem release lock 471*a*'. FIG. 33C illustrates the cartridge in the process of releasing the stent and anvil for support by the tool. In this process the finger grips 469*d* are pinched together. Thereafter, while the levers are held in the pinched together condition, the cartridge is removed from the tool and discarded.

FIG. 37A is cross sectional view through the tip of disposable cassette 452 of the compact firing tool 450. Anvil 460 is located on the inside of vessel wall 489. Once the surgeon activates the compact firing tool by depressing his thumb on the plunger this activates driver 465 which, via stem receiver 471*b*, pushes malleable stent 476 forward in direction 491 against anvil 460. Malleable stent 476 is completely constrained and tines 492 are backed-up against platform 462 and are supported by a shoulder 493 extending around the platform 462 so proper turning of the fasteners is achieved without buckling. FIG. 37B shows an intermediate firing position. As driver 465 continues to move forward, tines 492 of malleable stent 476 are supported by platform 462 and are forced into matching pockets 488A in anvil 460. As tines 492 begin to deform and curl towards stem 494 of anvil 488, shoulder 493 maintains contact with tines 492 thus preventing the tines from buckling outward and folding over flat instead of being formed to curl in the anvil pocket. FIG. 37C shows the tine formation completed. Once tines 492 of the malleable stent have finished curling back through the vessel wall, cutter blades 464 is deployed incising a slit in the vessel wall inside the malleable ring-shaped stent.

The final step in placing the malleable stent is spreading the stent open to a predetermined size. FIGS. 29B and 29C show the spreader bar carrier 630 which is connected to the plunger 486 and thumb ring 486*a*. The surgeon will press plunger 486 with his thumb after the malleable stent is fully crimped. Once fully crimped, cutter blades 464 and the secondary anvil are retracted.

Operation of the stent setting tool will be discussed with reference to FIGS. 31, 34A and 34B. A stent 600 includes a body 602 to which fastener tines 604 are anchored and to which a tab 606 is anchored. Tab 606 corresponds to the tabs discussed above including elements 74, 88, 100, 30C, 401, 405 and the like. Tab 606 includes legs 608 each attached at one end thereof to body 602 and meeting at an apex section 610 at a hole 612 which is defined through apex section 610 and an extension 614 extends from apex section 610. Two side notches 616 are defined in the side edges of extension 614 and a notch 618 is defined in end edge 620 of extension 614. Tabs 606 are used to manipulate the stent 602 for the purpose of adjusting the stent and permitting removal of the anvil as described above.

The tool shown in FIGS. 31, 34A and 34B includes a hollow body 629 through which anvil stem 632 extends with anvil head 634 on one end thereof in position to be inserted through an incision into a vessel $V_x$ as above described with concave guide grooves 636 in position to turn fasteners 604 inwardly toward edge 638 of the vessel adjacent to the incision. A tissue cutter 639 is located adjacent to body 629 in position to trim the vessel adjacent to the incision.

Pivotally attached to body 629 of the spreader bar carrier 630 is a spreader bar 640 for each tab 606. Each spreader bar 640 includes an arm 642 having one end pivotally attached to body 629 and a tab-engaging head 644 on the other end. Arm 642 moves from a first position with head 644 lying adjacent to body 629 to a second position with head 644 spaced from body 629, with the first position being indicated in solid lines in FIG. 35B and the second position being indicated in dotted lines in FIG. 35B.

Head 644 includes two projections 646 which engage notches 616 and is moved from the first position to the second position to spread the stent. A spreader sleeve 650 encircles body 629 and includes a cam surface 652 that slants upwardly and outwardly from body 629 adjacent to head 644. Two spreader cam pins 654 are attached to head 644 and slidably engage cam surface 652 so that distalward movement of sleeve 650 as indicated by arrow 656 forces the cam surface between pins 654 and body 629 causing those pins to ride up surface 652 thereby forcing head 644 outward in direction 658 toward the second position.

A stent retainer 660 is located between sleeve 650 and spreader bar 640 and engages tab 606 at notch 618 to keep the tab attached to head 644 whereby the outward movement of head 644 spreads stent 600. Distalward movement of body 629 in direction 656 forces fastener 604 through the vessel and into the fastener guide of anvil 634 to form the fastener on the vessel as discussed above.

Once the stent is configured in the desired manner, the cutter 639 can be operated and head 644 is disengaged from tab 606 by twisting the tool.

FIGS. 34A and 34B show how the malleable stent is spread. When the surgeon activates stretcher plunger 486, spreader sleeve 650 will move in the forward direction indicated by arrow 656. Spreader cam surface 652 will make contact with spreader cam follower pin 654. Spreader cam follower pin 654 is attached to ring spreader arm 642 which pivots near the proximal end of the firing tool. When spreader cam surface 652 makes contact with spreader cam pin 654, ring spreader arm 642 will move away from the center of the firing tool in direction 658 opening up malleable stent body 602 until the ring spreader bar bottoms out on the inside surface of spreader sleeve 650. Docking tabs 606 will be ejected from the ring spreader bar thereby releasing the malleable stent body. FIG. 29A shows the anvil release button CRB which the surgeon will press to release the anvil. Now the surgeon will complete the procedure by removing the anvil from the arteriotomy.

As discussed above, the fasteners of the stents may be formed by driving them against an anvil head such as anvil head 274 shown in FIG. 15 with a fastener turning section or groove 288 turning the fasteners inwardly from the position shown in FIG. 5 to the position shown in FIG. 3, for example. However, as will be understood by those skilled in the surgery art, the fasteners are very thin and must be correctly handled in order to ensure proper formation. If the fasteners are not properly turned, they may simply crumple or fold instead of smoothly turning into the FIG. 3 configuration.

Therefore, the present invention includes specially formed fastener tines such as shown in FIG. 51 as fastener tine 700. Fastener tine 700 is smoothly tapered from root 702 to tip 704 on both top surface 706 and bottom surface 708, as well as on both side edges 710 and 712. This multiplanar tapering causes the fastener tine to smoothly turn from the FIG. 5 configuration to the FIG. 3 configuration as tip 704 engages smoothly curving surface 714 (see FIG. 15) of anvil head 274. As is also shown in FIG. 51, root 702 is concave and smoothly curves at location 715 from top surface 716 of ring-shaped stent body 718 to top surface 706 and at location 717 to bottom surface 708 of fastener tine 700.

Fastener tine 700 is formed by a multiple etching process in the manner of a computer chip. Thus, a blank is masked and exposed to an etching solution in several steps to form the multiplanar fastener tine 700. For the sake of description, fastener tine 700 is shown extending radially outward from body 718 in FIG. 51. However, in use, the fastener tine will extend as shown in FIGS. 15 or 62 A–B with respect to body 718.

More specifically, the manufacturing method in which the malleable stent will be fabricated is a chemical etch process. The chemical etch process is capable of yielding a malleable stent with different thickness as shown in FIG. 58A. Ring-shaped body 718 itself must be thicker than fastener tines 700. This will keep the body planar after the spreading operation. If the body were too thin, it would distort into an uncontrollable shape. Fastener tines 700 must be thinner than ring-shaped body 718. This allows the tines to pierce the tissue without leaking and to form against the anvil. The process is illustrated in FIGS. 52–59. To begin the process, as shown in FIG. 52, a sheet 720 of stainless steel is coated with a photoresist coating. Stainless steel, titanium or any other acceptable surgically implantable material can be used for the ring-shaped body. The photoresist coating may be applied by laminating, dip coating, spraying or any other means known to one skilled in the art. Since the photoresist coating is light sensitive the coating should be carried out in a safe-light condition. After applying the photoresist to the metal sheet, the sheet is exposed to light with contact negatives 721 on the photoresist. This is done on both sides of the sheet, so the mirror image of the malleable stent on the bottom side is precision aligned to the malleable stent image on the topside of the sheet. This creates the precise resist image required to produce plurality of malleable ring-shaped stents 722 on both sides of the sheet as shown in FIG. 53. Alignment pins 723 or the like are used to ensure precise alignment location between the top and bottom negatives. This is done by first covering the coated sheet with a negative containing an image of the pattern of malleable stents. Next the sheet is placed under a light source rich in ultraviolet radiation to expose the photoresist coating on the sheet. After exposure, the photoresist is rinsed in a developer to remove the unexposed photoresist. Once the unexposed photoresist is fully removed, the sheet is baked to harden the remaining photoresist coating in the form of malleable stents. The sheet is now placed in a chemical bath that will etch away any areas that are not protected by the hardened photoresist. Once the sheet is rinsed removing the chemical etch bath, A single pass chemical etch process yields a chisel point 724 as shown in FIG. 54. This chisel point 724 is not acceptable, since it will tend to cut through the tissue and allow relatively large pathways in which blood leaks through the tine holes. The point that is needed to make a leak-free anastomosis is shown at 725 in FIG. 55A. It must taper in three directions, a sharp point 726 and rounded edges 727. The process of producing an acceptable point will now be described. FIG. 56 shows the body of the malleable stent being re-masked on both sides of the now etched out stents with photoresist coating 728, except for tines 700. The sheet will go through the exposure, baking and rinsing operations as described above and then back into the chemical etch bath. This time the sheet will be exposed to the chemical etch for a much shorter time. The only material that will be removed are the sharp edges on the tines. Once removed from the chemical etch bath for the second time, see FIG. 55A, the new point configuration 726 with rounded edges 727 will be present.

FIG. 57 shows a partial view of finished sheet 720. The ring-shaped stents are held to the sheet with carrier tabs 729 placed at the corners of each malleable stent. Also, registration holes 730 are located at the edges of the sheet. These holes are used to feed the unformed sheet 720 through a forming die in a controlled process to bend the tines in the appropriate formation and remove malleable stents 731 from the sheet. The sheet could be fed into an injection molding die where plastic will be formed around the stent in a configuration to facilitate loading the stent into the compact firing tool or to surround the stent in an absorbable polymer as described below. Now the malleable stents are ready to be loaded into the disposable cartridge or cassette. Keeping the malleable stents in a discrete pattern allows the stents to be formed, sheared and handled in an automated fashion.

In some instances, the desired spacing between tines causes one or more of the tines to spatially coincide with a connection tab. This situation is illustrated in FIGS. 58B and 58C in which tine 700' coincides with a connection tab 732 having a guide hole 733 therein. The etching process or any other process used to form the stent can be modified, as will be understood by those skilled in the art based on the teaching of this disclosure, to physically place a tine, such as tine 700' on a tab such as tab 732.

A variation of the configuration for framework or stent 50 shown in FIG. 4A is shown in FIGS. 60–62 as framework 750. Framework 750 includes a plurality of sections 752 to which fastener tines 753 are attached and sections 754 to which docking tabs are also attached. Bridge sections 756 are formed of absorbable material and connect sections 752 and 754 together. Framework 750 can be used with any of the docking elements discussed above, and will at least partially absorb into the patient's body after healing is complete. Sections 752 and 754 are formed of non-absorbable surgical material, such as Titanium, Stainless Steel, or the like and remain in place. The individual non-absorbable sections can move relative to each other whereby the size and shape of the opening can change based on the needs of the patient's body. The tines 753 are located on the non-absorbable sections.

Malleable framework 750 is formed with an over-molded absorbable polymer. Malleable framework 750 would be manufactured in the same manner as described above except the framework goes through a secondary process of injection molding. The finished sheet is similar to the sheet shown in FIG. 57 except there are connector tabs 755 bridging between tines 753. Unlike the malleable stent described above, the partially absorbable malleable framework 750 is not-continuous. The bridge sections 756 provide discontinuities 758 where absorbable polymer is over-molded. The sheet is placed into an injection molding press using registration holes 730 shown in FIG. 57 to align the sheet. Once the absorbable polymer is molded over the malleable stent connector tabs 755 are sheared off in a die. This results in malleable ring sections 760 held together with the absorbable polymer of the bridge section 756. FIG. 61 shows malleable stent 760 at the anastomosis of a graft 761 to a coronary artery 762 after a period of 6 weeks to 3 months. The absorbable polymer is no longer connected to malleable stent 760. By this time it has been absorbed into the body. This results in voids in the malleable stent 760 at discontinuities 758, which allow the anastomosis to move and expand if there is an increased demand of blood flow. The anastomosis elements can thus move to accommodate the patient's tissue.

As discussed above, if the tines on the malleable ring-shaped stents are too far apart, leak paths may be formed; however, if the tines are too close together, the tissue may be damaged when the two vessels are coupled together. Accordingly, there is an optimum spacing of tines on the malleable mounting structure for a specified tissue. For example, a stent on the aorta will have different tine spacing and number of tines than a stent on a coronary artery. Therefore, the inventors have determined that the best mode of the malleable ring-shaped stents will have tines spaced apart (centerline-to-centerline distance) of approximately 0.040 inches for end located tines, such as tines 800 shown in FIG. 62A and a spacing (centerline-to-centerline distance) of approximately 0.030 inches for side located tines, such as tines 801 of FIG. 62A. A tolerance of approximately ±0.003 inches can be accepted to account for tine misalignment while still providing proper tissue compression and a leak-free joint in the best mode. As shown in FIG. 63, positive peak to negative peak spacing (P1 to P2 spacing in FIG. 27) of 0.015 inches is used in the best mode as is a tine thickness adjacent to the ring body of approximately 0.005 inches. The misalignment illustrated in FIG. 63 is acceptable.

It is understood that while certain forms of the present invention have been illustrated and described herein, it is not to be limited to the specific forms or arrangements of parts described and shown. For example, docking elements other than those disclosed above can be used without departing from the scope of the present disclosure. Examples of such alternative docking elements include Tinnerman fastener type elements, C-clips, clips with VELCRO, elastomeric clips, adhesive and the like. Still other docking methods contemplated by this invention include elastomeric rings, folding or twisting one docking leg over another docking leg, folding both docking legs together, twisting both docking legs together, crimping both docking legs together, having a post on one docking leg penetrate a hole on the mating docking leg, having a post with a retention feature on one docking leg penetrate a hole on the mating docking leg, having a post on one docking leg penetrate a hole with a retention feature on the mating docking leg, a suture loop to hold the docking legs together, a c-shaped clip that is crimped over the docking legs, a spring-loaded c-shaped clip that holds the docking legs together, a spring-loaded c-shaped clip with an integral suture cutter, magnetic docking legs that align and hold the docking legs together, a rubber collar with a steel ring that binds on the guide suture which holds the docking legs together, and the docking legs are bonded together with a rivet. Still further, the inventors have discovered and as will be understood from the above teaching, the method by which the stents are docked or joined, influences joint compression. Since docking is a function of a number of factors, these factors include the joining medium or the spring rate of the joining legs so that by varying these two factors a compliant joint can be constructed which provides a joint that is just tight enough to seal but not tight enough to crush the tissue. Yet another factor that can be varied is the width of the ring-shaped stent so that by increasing or decreasing the length of the docking legs the joint can be made more or less compliant. For example by decreasing the width of a docking leg, the joint can be made more flexible for thicker tissue. Another factor is the shape of the tines. A thicker tine will hold the malleable stent better on tissue that has less tensile strength, such as aorta. A thinner tine will work better on small arteries less than 2 millimeters. FIGS. 64A and 64B illustrate yet another alternative form of the malleable ring-shaped stent with manufacturing dimensions thereon.

We claim:

1. A method for forming an anastomosis comprising:
   A) forming an incision in a first vessel;
   B) installing an anvil into the first vessel through the incision;
   C) mounting a first malleable mounting structure on the first vessel by setting fasteners on the first mounting structure into the first vessel adjacent to the incision;
   D) fully forming the fasteners by driving them against the anvil and gently turning them toward the incision;
   E) manipulating the first mounting structure into a configuration opening the incision in the first vessel;
   F) removing the anvil from the first vessel through the incision therein;
   G) forming an incision in a second vessel;
   H) installing an anvil into the second vessel through the incision in the second vessel;
   I) mounting a second malleable mounting structure on the second vessel by setting fasteners on the second mounting structure into the second vessel adjacent to the incision in the second vessel;
   J) fully forming the fasteners of the second mounting structure by driving them against the anvil in the second vessel and gently turning them toward the incision in the second vessel;
   K) manipulating the second mounting structure into a configuration opening the incision in the second vessel;
   L) removing the anvil from the second vessel through the incision therein;
   M) guiding the first and second mounting structures into contact with each other to bring the first and second vessels in abutting contact with each other; and
   N) connecting the first and second mounting structures together.

2. The method according to claim 1 further comprising trimming the first and second vessel adjacent the incisions formed therein.

3. The method according to claim 1 wherein, upon guiding of the first and second mounting structures into contact, the fasteners on the respective structures interdigitate with each other and the vessels contact to form a generally sinusoidal joint therebetween.

4. A method for preparing a vessel for anastomosis, said method comprising:
   A) forming an incision in the vessel;
   B) installing an anvil into the vessel through the incision;
   C) mounting a malleable mounting structure on the vessel by setting fasteners on the mounting structure into the vessel adjacent the incision;
   D) securing the mounting structure to the vessel by driving the fasteners against the anvil to crimp the fasteners into the vessel;
   E) deforming the mounting structure to change a shape of an opening therethrough, thereby also opening the incision; and
   F) removing the anvil from the vessel through the incision.

* * * * *

UNITED STATES PATENT AND TRADEMARK OFFICE
CERTIFICATE OF CORRECTION

PATENT NO. : 6,884,251 B2  Page 1 of 1
APPLICATION NO. : 10/384250
DATED : April 26, 2005
INVENTOR(S) : Spence et al.

It is certified that error appears in the above-identified patent and that said Letters Patent is hereby corrected as shown below:

Column 23, line 2, please delete the word "extends" and insert therefore --extended--;
Column 27, line 20, please delete the word "materials" and insert therefore --material--;
Column 31, line 19, please delete the word "allegator" and insert therefore --alligator--;
Column 33, line 32, before the word "another" please insert the word --of--;
Column 34, line 59, please delete the words "that the surgeon the" and insert therefore --the surgeon that the--;
Column 35, line 58, please delete the word "a" and insert therefore --an--;
Column 36, line 18, before the word "cross" insert the word --a--;

Signed and Sealed this

Twenty-third Day of September, 2008

JON W. DUDAS
*Director of the United States Patent and Trademark Office*